US006797702B1

(12) United States Patent
Roth et al.

(10) Patent No.: US 6,797,702 B1
(45) Date of Patent: *Sep. 28, 2004

(54) METHODS AND COMPOSITIONS COMPRISING DNA DAMAGING AGENTS AND P53

(75) Inventors: Jack A. Roth, Houston, TX (US); Toshiyoshi Fujiwara, Okayama (JP); Elizabeth A. Grimm, Houston, TX (US); Tapas Mukhopadhyay, Houston, TX (US); Wei-Wei Zhang, Houston, TX (US); Laurie B. Owen-Schaub, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/918,407

(22) Filed: Aug. 26, 1997

Related U.S. Application Data

(63) Continuation of application No. 08/233,002, filed on Apr. 25, 1994, now Pat. No. 5,747,469, which is a continuation-in-part of application No. 08/145,826, filed on Oct. 29, 1993, now Pat. No. 6,410,010, which is a continuation-in-part of application No. 07/960,513, filed on Oct. 13, 1992, now abandoned, which is a continuation-in-part of application No. 07/665,538, filed on Mar. 6, 1991, now abandoned.

(51) Int. Cl.⁷ ............................................. A61K 31/713
(52) U.S. Cl. ..................... 514/44; 435/320.1; 536/23.1; 536/24.1
(58) Field of Search ......................... 435/6, 320.1, 325, 435/446, 443, 448, 455, 456; 514/44; 536/23.1, 24.1

(56) References Cited

U.S. PATENT DOCUMENTS

| 4,740,463 A | 4/1988 | Weinberg et al. ............ 435/456 |
| 4,920,209 A | 4/1990 | Davis et al. |
| 4,980,289 A | 12/1990 | Temin et al. ............. 435/235.1 |
| 5,055,400 A | 10/1991 | Lo et al. ..................... 435/69.1 |
| 5,166,320 A | 11/1992 | Wu et al. ................... 530/395 |
| 5,252,479 A | 10/1993 | Srivastava ............... 435/235.1 |
| 5,328,470 A | 7/1994 | Nabel et al. ................ 604/101 |
| 5,362,623 A | 11/1994 | Vogelstein et al. |
| 5,496,731 A | 3/1996 | Xu et al. |
| 5,527,676 A | 6/1996 | Vogelstein et al. |
| 5,532,220 A | 7/1996 | Lee et al. ...................... 514/44 |
| 5,585,362 A | 12/1996 | Wilson et al. |
| 5,747,469 A | 5/1998 | Roth et al. ..................... 514/44 |
| 5,932,210 A | 8/1999 | Gregory et al. |
| 6,090,566 A | 7/2000 | Vogelstein et al. |

FOREIGN PATENT DOCUMENTS

| EP | 0174608 | 9/1985 |
| EP | 0351585 | 6/1989 |
| EP | 0390323 | 10/1990 |
| EP | 0475623 | 8/1991 |
| FR | 2688514 | 9/1993 |
| JP | 04-009338 | 1/1992 |
| JP | 8-508879 | 9/1996 |
| WO | WO 90/05180 | 5/1990 |
| WO | WO 90/10448 | 9/1990 |
| WO | WO 91/15580 | 10/1991 |
| WO | WO 93/03769 | 3/1993 |
| WO | WO 93/19191 | 9/1993 |
| WO | WO 93/25224 | 12/1993 |
| WO | WO 94/06910 | 3/1994 |
| WO | WO 94/08026 | 4/1994 |
| WO | WO 94/10323 | 5/1994 |
| WO | WO 94/18992 | 9/1994 |
| WO | WO 94/24297 | 10/1994 |
| WO | WO 94/26914 | 11/1994 |
| WO | WO 95/02697 | 1/1995 |
| WO | WO 95/11301 | 4/1995 |
| WO | 95/11984 | 5/1995 |
| WO | WO 95/14101 | 5/1995 |
| WO | WO 95/14102 | 5/1995 |
| WO | WO 95/23867 | 9/1995 |
| WO | WO 95/30002 | 11/1995 |

OTHER PUBLICATIONS

Fritsche et al. INhibition of cell proliferation by an adenovirus vector expressing the human wild tupe p53 protein. Int. J. Oncology. vol. 3:781–785, 1993.*
Lane, p53, guardian of the genome. Nature, vol. 358:15–16, Jul. 1992.*
Levine The p53 tumor suppressor gene and product. Biol. Chem. Hoppe–Seyler, vol. 374:227–235, Apr. 1993.*
Stratagene catalogue, 1988, p. 39.*
Bacchetti et al. Inhibition of cell proliferation by an adenovirus vector expressing the human wild type p53 protein. Int. J. Oncol. vol. 3(5):781–788, 1993.*
Kastan et al. Participation of p53 in the cellular response to DNA damage. Cancer Res. vol. 51:6304–6411, Dec. 1991.*
Kuerbitz et al. Wild–type ;53 is a cell cycle checkpoint determinant following irradiation. PNAS vol. 89:7491–7495, Aug. 1992.*
Verma et al. Gene therapy—promises, problems and prospects. Nature. vol. 389:239–242, Sep. 1997.*

(List continued on next page.)

Primary Examiner—James Ketter
(74) Attorney, Agent, or Firm—Fulbright & Jaworski L.L.P.

(57) ABSTRACT

The present invention relates to the use of tumor suppressor genes in combination with a DNA damaging agent or factor for use in killing cells, and in particular cancerous cells. A tumor suppressor gene, p53, was delivered via a recombinant adenovirus-mediated gene transfer both in vitro and in vivo, in combination with a chemotherapeutic agent. Treated cells underwent apoptosis with specific DNA fragmentation. Direct injection of the p53-adenovirus construct into tumors subcutaneously, followed by intraperitoneal administration of a DNA damaging agent, cisplatin, induced massive apoptotic destruction of the tumors. The invention also provides for the clinical application of a regimen combining gene replacement using replication-deficient wild-type p53 adenovirus and DNA-damaging drugs for treatment of human cancer.

82 Claims, 21 Drawing Sheets

OTHER PUBLICATIONS

Anderson, W. F. Human gene therapy. Nature. vol. 392:25–30, Apr. 1998.*

Orkin et al. Report and recommendations of the panel to assess the NIH investment in research on gene therapy, Dec. 1995.*

Wills et al. Tumor suppressor gene therapy on cancer: Adenonviral mediated gene transfer of p53 and retinoblasoma cDNA into human tumor cell lines. J. Cell. Biochem. Supp. 18C, p. 204, Feb. 19, 1994.*

Gregory et al. Tumor suppressof gene therapy of cancer: Adenoviral mediated gene transfer of p53 into human tumor cell lines. J. Cell. Biochem. Supp. 18A. p. 237, Jan. 29, 1994.*

Tischler et al. Increases in sequence specific DNA binding by p53 following treatment with chemotherapeutic and DNA damaging agents. Cancer Research. vol. 53:2212–2216, May 15, 1994.*

Clarke et al. Thyocyte apoptosis induced by p53–dependent and independant pathways. Nature. vol. 362:849–852, Apr. 29. 1993.*

Scott et al. p53 is required for radiation induced apoptosis in mouse thymocytes. Nature. vol. 362:847–849, Apr. 29, 1993.*

Bandyopadhyay and Temin, "Expression of complete chicken thymidine kinsase gene inserted in a tetrovirus vector," *Mol. Cell. Biol.*, 4(4):749–754, 1984.

Bowtell et al., "Comparison of expression in hemopoietic cells by retroviral vectors carrying two genes," *J. Virol.*, 62(7):2464–2473, 1988.

Casson et al., "p53 gene mutations in Barrett's epithelium and esophageal cancer," *Cancer Res.*, 51:4495–4499, 1991.

Chen et al., "Genetic mechanisms of tumor suppression by the human p53 gene," *Science*, 250:1576–1580, 1990.

Chen et al., "Expression of wild–type p53 in human A673 cells suppresses tumorigenicity but not growth rate," *Oncogene*, 6:1799–1805, 1991.

Goyette et al., "Progression of colorectal cancer is associated with multiple tumor suppressor gene defects but inhibition of tumorigenicity is accomplished by correction of any single defect via chromosome transfer," *Mol. Cell. Biol.*, 12(3):1387–1395, 1992.

Gusterson et al., "Expression of p53 in premalignant and malignant squamous epithelium," *Oncogene*, 6:1785–1798, 1991.

Kumar et al., "Activation of ras oncogenes preceeding the onset of neoplasia," *Science*, 248:1101–1104, 1990.

Maxwell et al., "Inefficiency of expression of Luciferase Reporter from transfected murine leukaemia proviral DNA may be partially overcome by providing a strong polyadenylation signal," *J. Gen. Virol.*, 72:1721–1724, 1991.

Mukhopadhyay et al., "Specific inhibition of K–ras expression and tumorigenicity of lung cancer cells by antisense RNA," *Cancer Res.*, 51:1744–1748, 1991.

Owens and Boyd, "Expressing antisense Po RNA in Schwann cells perturbs myelination," *Development*, 112:639–649, 1991.

Palmer et al., "Efficient retrovirus–medicated transfer and expression of a human adenosine deaminase gene in diploid skin fibroblasts from an adenosine deaminase–deficient human," *Proc. Natl. Acad. Sci. USA*, 84:1055–1059, 1987.

Seyama et al., "In vitro and in vivo regulation of liver epithelial cells carrying a metallothionein–rasT24 fusion gene," *Mol. Carcinogenesis*, 1:89–95, 1988.

Takahashi et al., "Wild–type but not mutant p53 suppresses the growth of human lung cancer cells bearing multiple genetic lesions," *Cancer Res.*, 52:2340–2343, 1992.

Zhou and Duesberg, "myc protooncogene linked to retroviral promoter, but not to enhancer, transforms embryo cells," *Proc. Natl. Acad. Sci. USA*, 85:2924–2928, 1988.

Conroy, "New gene therapy cleared for use against lung cancer," *Biotech Daily*, pp. 3–4, 1992.

Dialog Search Report dated Sep. 22, 1992.

Sundaresan et al., "Somatic genetic changes in pre–invasive lesions in bronchial epithelium," *J. Pathol.*, 167(Suppl):100A, 1992, Abstract only.

Dialog Search Reports dated Aug. 7, 1992 and Feb. 26, 1993.

Debus et al., *J. Cancer Res. Clin. Oncol.*, 116(Suppl Part 1):5–162, Abstract # A2.037.09, 1990.

Delauney et al., "A stable bifunctional antisense transcript inhibiting gene expression in transgenic plants," *Proc. Natl. Acad. Sci. USA*, 85:4300–4304, 1988.

Feig et al., "Somatic activation of $ras^K$ gene in a human ovarian carcinoma", *Science*, 223:698–701, 1984.

Finkel et al., "Activation of ras genes in human tumors does not affect localization, modification, or nucleotide binding properties of p21", *Cell*, 37:151–158, 1984.

Griep and Heiner, "Antisense Myc sequences induce differentiation of F9 cells", *Proc. Natl. Acad. Sci. USA*, 85:6806–6810, 1988.

Gunning et al., "A human 8–actin expression vector system directs high–level accumulation of antisense transcripts", *Proc. Natl. Acad. Sci. USA*, 84:4831–4835, 1987.

Kasid et al., "Effect of antisense c–raf–1 on tumorigenicity and radiation sensitivity of a human squamous carcinoma," *Science*, 243:1354–1356, 1989.

Khokha et al., "Antisense RNA–induced reduction in murine timp levels confers oncogenicity on swiss 3T3 cells," *Science*, 243:947–950, 1989.

Kris et al, "Expression of Ki–ras oncogene in tumor cell variants exhibiting different metstatic capabilities," *Int. J. Cancer*, 35:277–230, 1985.

Izant and Weintraub, "Inhibition of thymidine kinase gene expression by anti–sense RNA: A molecular approach to genetic analysis," *Cell*, 36:1007–1015, 1984.

Johnson et al., "Transfection of a rat cell line with the v–Ki–ras oncogene is associated with enhanced susceptibilityto natural killer cell lysis," *J. Exp. Med.*, 162:1732–1737, 1985.

McGrath et al., "Structure and organization of the human Ki–ras proto–oncogene and a related processed pseudogene," *Nature*, 304:501, 1983.

MaGrath, "Tumor–specificantisense oligonucleotidesfor controlling cancer", *Chemical Abstracts*, 114(7):68, Abstract No. 114:55778n, 1991.

Mercola et al., "Antisense RNA: Eukaryotic controls," *Gene*, 72:253–265, 1988.

Miller and Rosman, Improved retroviral vectors for gene transfer and expression,*BioTechniques*, 7(9):980–990, 1989.

Munroe and Stephen, "Antisense RNA inhibits splicing of pre–mRNA in vitro", *EMBO J.*, 7(8):2523–2532, 1988.

Prochownik et al., "c–myc antisense transcripts accelerate differentiation and inhibit $G_1$ progression in murine erythroleukemiacells," *Mol. Cell. Biol.*, 8(9):3683–3695, 1988.

Santos et al., "Malignant activation of a K–ras oncogene in lung carcinoma but not in normal tissue of the same patient," *Science*, 223:661–664, 1984.

Shimizu et al., "Structure of the Ki–ras gene of the human lung carcinoma cell line Calu–1", *Nature*, 304:497–500, 1983.

Stowers et al., "Activation of the K–ras protooncogene in lung tumors from rats and mice chronically exposed to tetranitromethane," *Cancer Res.*, 47:3212–3219, 1987.

Taya et al., "A novel combination of K–ras and myc amplification accompanied by point mutational activation of K–ras in a human lung cancer," *EMBO J.*, 3(12):2643–2946, 1984.

Toftgard et al., "Proto–oncogene expression during two–stage carcinogenesis in mouse skin," *Carcinogenesis*, 6(4):655–657, 1985.

Vogelstein et al., "Genetic alterations during colorectal–tumor development," *N. Engl. J. Med.*, 319(9):525–532, 1988.

Wahran et al., *Tumour Biol.*, 6:41–56, 1985.

Winter and Perucho, "Oncogene amplification during tumorigenesis of established rat fibroblasts reversibly transformed by activated human ras oncogenes," *Mol. Cell. Biol.*, 6(7):2562–2570, 1986.

InternationalSearch Report, mailed Aug. 20, 1992.

Brown et al., "Increased accumulation of p53 protein in cisplatin–resistantovarian cell lines," *Int. J. Cancer*, 55:678–684, 1993.

Clarke et al., "Thymocyte apoptosis induced by p53–dependent and independent pathways," *Nature*, 362:849–852, 1993.

El–Deiry et al., "WAFI, a potential mediator of p53 tumor suppression," *Cell*, 75:817–825, 1993.

Fritsche et al., "Induction of nuclear accumulation of the tumor–suppressor protein p53 by DNA–damaging agents," *Oncogene*, 8:307–318, 1993.

Fujiwara et al., "A retroviral wild–type p53 expression vector penetrates human lung cancer spheroids and inhibits growth by inducing apoptosis," *Cancer Res.*, 53:4129–4133, 1993.

Harper et al., "The p21 Cdk–interacting protein Cip1 is a potent inhibitor of G1 cyclin–dependent kinases," *Cell*, 75:805–816, 1993.

Lowe et al., "p53–dependent apoptosis modulates the cytotoxicity of anticancer agents," *Cell*, 74:957–967, 1993.

Lowe et al., "p53 is required for radiation–induced apoptosis in mouse thymocytes," *Nature*, 362:847–849, 1993.

Merritt et al., "The role of p53 in spontaneous and radiation–induced apoptosis in the gastrointestinaltract of normal and p53–deficientmice," *Cancer Res.*, 54:614–617, 1994.

Tishler et al., "Increases in sequence specific DNA binding by p53 following treatment with chemotherapeuticand DNA damaging agents," *Cancer Res.*, 53:2212–2216, 1993.

Brown et al., "Mutant p53 confers cisplatin–sensitivity to resistant ovarian tumour cells with elevated wild–type p53," *Proc. Am. Assoc. Cancer Res.*, 34:355, Abstract #2116, 1993.

Donehower, "Tumor suppressor gene p53 and apoptosis," *Cancer Bull.*, 46(2):161–166, 1994.

El Rouby et al., "p53 gene mutation in B–cell chronic lymphocytic leukemia is associated with drug resistance and its independent of MDR1/MDR3 gene expression," *Blood*, 82(11):3452–3459, 1993.

Fan et al., "The role of p53 in cell cycle arrest and apoptosis induced by multiple chemotherapeutic agents in Burkitt's lymphoma cells," *Proc. Am. Assoc. Cancer Res.*, 35:311, Abstract #1851, 1994.

Fornace, Jr. "Induction by radiation of mammalian genes associated with growth–arrest and apoptosis, and the role for the p53 tumor suppressor in their regulation," *Proc. Am. Assoc. Cancer Res.*, 35:681–682, 1994.

Fritsche et al., "Induction of nuclear accumulation of the tumor–suppressor protein p53 by DNA–damaging agents," published erratum, *Oncogene*, 8(9):2605, 1993.

Hecht et al., "Comparison of wildtype and mutated p53 protein expression induced by UV irradiation of cultured cells," *FASEB Journal*, 8:A667, #3870, 1994.

Kaneko et al., "Induction of apoptosis and p53 protein by adriamycin and hyperthermia in a rat mammary adenocarcinomacell line," *Proc. Am. Assoc. Cancer Res.*, 35:314, #1871, 1994.

Kastan et al., "Participation of p53 protein in the cellular response to DNA damage," *Cancer Res.*, 51:6304–6311, 1991.

Kastan, "p53: a determinant of the cell cycle response to DNA damage," *Adv. Exp. Med. Biol.*, 339:295–296, 1993.

Kastan et al., "p53 and other molecular controls of the response to DNA damage," *J. Cell.Biochem.*, 9(18C):164, 1994.

Kemp et al., "p53–deficient mice are extremely susceptible to radiation–induced tumorigenesis," *Nature Genetics*, 8(1):66–69, 1994.

Lane, "A death in the life of p53," *Nature*, 362:786–787, 1993.

Lee and Bernstein, "p53 mutations increase resistance to ionizing radiation," *Proc. Natl. Acad. Sci. USA*, 90(12):5742–5746, 1993.

Levine et al., "The 1993 Walter Hubert Lecture: the role of the p53 tumour–suppressor gene in tumorigenesis," *Br. J. Cancer*, 69(3):409–416, 1994.

Loganzo, Jr. et al., "Stabilization of p53 protein is a critical response to UV radiation in human melanocytes:Implications for melanoma development," *Mol. Cell. Differ.*, 2(1):23–43, 1994.

Lotem and Sachs, "Regulation by bcl–2, c–myc, and p53 of susceptibility to induction of apoptosis by heat shock and cancer chemotherapy compounds in differentiation–competentand–defective myeloid leukemic cells," *Cells Growth Differ.*, 4(1):41–47, 1993.

Lotem and Sachs, "Hematopoietic cells from mice deficient in wild–type p53 are more resistant to induction of apoptosis by some agents," *Blood*, 82(4):1092–1096, 1993.

Maity et al., "The molecular basis for cell cycle delays following ionizing radiation: a review," *Radiother. Oncol.*, 31(1):1–13, 1994.

McIlwrath et al., "Cell cycle arrests and radiosensitivity of human tumor cell lines: Dependence on wild–type p53 for radiosensitivity," *Cancer Res.*, 54(14):3718–3722, 1994.

Nabeya et al., "The mutational status of p53 protein in gastric cancer cell lines predicts sensitivity to chemotherapeuticagents," *Proc. Am. Assoc. Cancer Res.*, 35:602, Abstract #3591, 1994.

O'Connor et al., "Relationship between p53, cyclin E–cdk2 kinase complexes and G1 arrest induced by ionizing radiation in human cells," *Proc. Am. Assoc. Cancer Res.*, 35:635, Abstract #3785, 1994.

Petty et al., "Expression of the p53 tumour suppressor gene product is a determinant of chemosensitivity," *Biochem. Biophys. Res. Commun.*, 199(1):264–270, 1994.

Rau et al., "Response of p53 to treatment with actinomycin D in human mammary carcinoma cell lines," *J. Cancer Res. Clin. Oncol.*, 120:R108, 1994.

Shaw et al., "Induction of apoptosis by wild–type p53 in a human colon tumor–derived cell line," *Proc. Natl. Acad. Sci. USA*, 89(10):4495–4499, 1992.

Slichenmyer et al., "Loss of a p53–associated G1 checkpoint does not decrease cell survival following DNA damage," *Cancer Res.*, 53(18):4164–4168, 1993.

Varghese et al., "The role of p53 and ras genes in radiation–induced transformation of immortalized human epidermal keratinocytes," *Proc. Am. Assoc. Cancer Res.*, 35:91, Abstract #542, 1994.

Yamada and Ohyama, "Radiation and apoptosis," *Gan To Kogaku Ryoho*, 21(5):602–607, 1994, Abstract Only.

Casey et al., "Growth suppression of human breast cancer cells by the introduction of a wild–type p53 gene," *Oncogene*, 6:1791–1797, 1991.

Wills and Menzel, "Adenovirus vectors for gene therapy of cancer," *J. Cell. Biochem.*, Abstract #S216, p 204, 1993.

Zhang et al., "Generation and identification of recombinant adenovirus by liposome–mediated transfection and PCR analysis," *BioTechniques*, 15(5):868–872, 1993.

PCT Search Report dated Jul. 5, 1995.

Su et al., "Transformation and radiosensitivity of human diploid skin fibroblasts transfected with SV40 T–antigen mutants defective in RB and p53 binding domains," *Int. J. Radiat. Biol.*, 62(4):461–468, 1992.

Petty et al., "Expression of the p53 tumour suppressor gene product is a determinant of chemosensitivity," *Biochem. Biophys. Res. Commun.*, 199(1):264–270, 1994.

PCT Search Report dated Apr. 24, 1995.

Baker et al., "Suppression of human colorectal carcinoma cell growth by wild–type p53", *Science*, 249:912–915, 1990.

Bargonetti et al., "Wild–type but not mutant p53 immunopurified proteins bind to sequences adjacent to the SV40 origin of replication," *Cell*, 65:1083–1091, 1991.

Berkner, "Development of adenovirus vectors for the expression of heterologous genes", *BioTechniques*, 6(7):616–629, 1988.

Blenis, "Signal transduction via the MAP kinases: Proceed at your own RISK", *Proc. Natl. Acad. Sci. USA*, 90:5889–5892, 1993.

Brachman et al., "p53 mutation does not correlate with radiosensitivity in 24 head and neck cancer cell lines", *Cancer Res.*, 53:3667–3669, 1993.

Capecchi, "Altering the genome by homologous recombination", *Science*, 244:1288–1292, 1989.

Cheng et al., "Suppression of acute lymphoblastic leukemia by the human wild–type p53 gene," *Cancer Res.*, 52:222–226, 1992.

Coleman et al., "Radiation and chemotherapy sensitizers and protectors", *Critical Reviews In Oncology/Hematology*, 10(Issue 3):225–252, 1990.

Comings, "A general theory of carcinogenesis," *Proc. Natl. Acad. Sci. USA*, 70(12–Part I):3324–3328, 1973.

Friedman, "Gene therapy of cancer through restoration of tumor–suppressor functions?" *Cancer*, 70(6–Suppl):1810–1817, 1992.

Gudkov et al., "Isolation of genetic suppressor elements, inducing resistance to topoismerase II–interaction cytotoxic drugs, from human topoiosmerase II cDNA", *Proc. Natl. Acad. Sci. USA*, 90:3231–3235, 1993.

Houghten and Richard, "Peptide libraries: criteria and trends," *Technical Focus*, 9(7):235–239, 1993.

Itoh et al., "The polypeptide encoded by the cDNA for human cell surface antigen Fas can mediate apoptosis," *Cell*, 66:233–243, 1991.

Jayawickreme et al., "Creation and functional screening of a multi–use peptide library," *Proc. Natl. Acad. Sci. USA*, 91:1614–1618, 1994.

Kamb et al., "A cell cycle regulator potentially involved in genesis of many tumor types," *Science*, 264:436–440, 1994.

Kern et al., "Identification of p53 as a sequence–specific DNA–binding protein," *Science*, 252:1708–1711, 1991.

Knudson, Jr., "Mutation and cancer: Statistical study of retinoblastoma," *Proc. Natl. Acad. Sci. USA*, 68(4):820–823, 1971.

Kuerbitz et al., "Wild–type p53 is a cell cycle checkpoint determinant following irradiation," *Proc. Natl. Acad. Sci. USA*, 89:7491–7495, 1992.

Li et al., "A cancer family syndrome in twenty–four kindreds," *Cancer Res.*, 48:5358–5362, 1988.

Malkin et al., "Germ line p53 mutations in a familial syndrome of breast cancer, sarcomas, and other neoplasms," *Science*, 250:1233–1238, 1990.

Mansour et al., "Introduction of a lacZ reporter gene into the mouse int–2 locus by homologous recombination," *Proc. Natl. Acad. Sci. USA*, 87:7688–7692, 1990.

Marshall, "Hot lips and phosphorylation of protein kinases," *Nature*, 367:686, 1994.

Mercer et al., "Negative growth regulation in a glioblastoma tumor cell line that conditionally expresses human wild–type p53," *Proc. Natl. Acad. Sci. USA*, 87:6166–6170, 1990.

Michalovitz et al. "Conditional inhibition of transformation and of cell proliferation by temperature–sensitivemutant of p53," *Cell*, 62:671–680, 1990.

Nigro et al., "Mutations in the p53 gene occur in diverse human tumour types," *Nature*, 342:705–708, 1989.

O'Connor et al., "Role of the p53 tumor suppressor gene in cell cycle arrest and radiosensitivity of Burkitt's lymphoma cell lines," *Cancer Res.*, 53:4776–4780, 1993.

Paull et al., "The synthesis of XTT: a new tetrazolium reagent that is bioreducible to a water–soluble formazan," *J. Heterocyclic Chem.*, 25:911–914, 1988.

Petty et al., "Expression of the p53 tumour suppressor gene product is a determinant of chemosensitivity," *Biochem. and Biophys. Res. Comm.*, 199(1):264–270, 1994.

Phillips et al., "Transition–state characterization: a new approach combining inhibitor analogues and variation in enzyme structure," *Biochem.*, 31:959–963, 1992.

Revet et al., "Homologous DNA targeting with RecA protein–coated short DNA probes and electron microscope mapping on linear duplex molecules," *J. Mol. Biol.*, 232:779–791, 1993.

Saris et al., "Treatment of murine primary brain tumors with systemic interleukin–2 and tumor–infiltrating lyphocytes," *J. Neurosurg.*, 76:513–519, 1992.

Shaulsky et al., "Involvement of wild–type p53 in pre–B–cell differentiation in vitro," *Proc. Natl. Acad. Sci. USA*, 88:8982–8986, 1991.

Shay et al., "A role for both RB and p53 in the regulation of human cellular senescence," *Experimental Cell Res.*, 196:33–39, 1991.

Muzyczka "Use of adeno-associated virus as a general transduction vector for mammalian cells," *Microbiol. Immunol.*, 158:98–129, 1992.

Srivastava et al., "Germ-line transmission of a mutated p53 gene in a cancer-prone family with Li-Fraumeni syndrome," *Nature*, 348:747–749, 1990.

Takahashi et al., "p53: A frequent target for genetic abnormalities in lung cancer," *Science*, 246:491–494, 1989.

Thomas et al., "High-fidelity gene targeting in embryonic stem cells by using sequence replacement vectors," *Molec. Cell. Biol.*, 12(7):2919–2923, 1992.

Ullrich et al., "Human wild-type p53 adopts a unique conformational and phosphorylation state in vivo during growth arrest of glioblastoma cells," *Oncogene*, 7:1635–1643, 1992.

Unger et al., "Functional domains of wild-type and mutant p53 proteins involved in transcriptional regulation, transdominant inhibition, and transformation suppression," *Molec. Cell. Biol.*, 13(9):5186–5194, 1993.

Vogelstein and Kinzler, "p53 function and dysfunction," *Cell*, 70:523–526, 1992.

Wagner et al., "Coupling of adenovirus to transferrin-polylysine/DNA complexes greatly enhances receptor-mediated gene delivery and expression of transfected genes," *Proc. Natl. Acad. Sci. USA*, 89:6099–6103, 1992.

Weislow et al., "New soluble-formazan assay for HIV-1 cytopathic effects: application to high-flux screening of synthetic and natural products for AIDS-antiviral activity," *J. Natl. Cancer Inst.*, 81(8):577–586, 1989.

Wu et al., "Receptor-mediatedgene delivery in vivo," *J. Biol. Chem.*, 266(22):14338–14342,1991.

Yonish-Rouach et al., "Wild-type p53 induces apoptosis of myeloid leukemic cells that is inhibited by interleukin-6," *Nature*, 352:345–347, 1991.

Yoshimura et al., "Expression of the human cystic fibrosis transmembrane conductance regulator gene in the mouse lung after in vivo intratracheal plasmid-mediated gene transfer," *Natl. Acid Res.*, 20(12):3233–3240, 1992.

Zhu et al., "Systemic gene expression after intravenous DNA delivery into adult mice," *Science*, 261:209–211, 1993.

Singleton and Sainsbury, Dictionary of Microbiology and Molecular Biology, 2nd Ed., John Wiley & Sons, Publ., pp. 591 and 920. (1987).

Stedman's Medical Dictionary, 25th Ed., Williams & Wilkins, Publ., p. 245, (1990).

*In: Comprehensive Textbook of Oncology*, vol. 1, 2nd. Ed., Williams & Wilkins, Publ., pp. 477, 527–536, 565–568, 590–594, 607–612. (1986).

*In: Comprehensive Textbook of Oncology*, vol. 2, 2nd. Ed., Williams & Wilkins, Publ., pp. 1098, 1138–1140, 1170, 1329, 1168, 1569–1572. (1986).

Federal Register, 47(56):pp. Title—VI and i–iv, Mar. 23, 1982.

Steel, "Cyclins and cancer: wheels within wheels," *Lancet*, 343:931–932, 1994.

*Proceedings of the American Associationfor Cancer Research*, 36:21, Mar. 1995.

Fujiwara et al., "Induction of chemosensitivity in human lung cancer cells in vivo by adenovirus-mediated transfer of the wild-type p53 gene," *Cancer Res.*, 54:2287–2291, 1994.

Diller et al., "p53 functions as a cell cycle control protein in osteosarcomas," *Molec. Cell. Biol.*, 10(11):5772–5781, 1990.

Cureil et al., "High-efficiency gene transfer mediated by adenovirus coupled to DNA-polylysine complexes," *Human Gene Therapy*, 3:147–154, 1992.

Foreman et al., *Bone Marrow Transport.*, 4(3), 1990.

Graham et al., *Methods in Molec. Biol. Gene Transfer and Expres. Protocols*, 7(11):109–128, 1991.

Hinds et al., *Cell Growth and Differentiation*, 571–580, 1990.

Huston et al., "Medical application of single-chain antibodies," *Internatl. Rev. Immun.*, 10(2–3):195–217, 1993.

Jolly, "Viral vector systems for gene therapy," *Cancer Gene Therapy*, 1(1):51–64, 1994.

Kriegler et al., *In: Gene Transfer and Expression: A Laboratory Manual*.

Romer and Friedman, *In: Annals of the New York Academy of Science, Gene Therapy for Neoplastic Diseases*, 716:265–282 (1994).

Van de Waterbeemd, "Recent progress in QSAR-technology," *Drug Design and Discovery*, 9:277–285, 1993.

Copies of slides from presentation by Jack A. Roth on Sep. 19, 1996.

Bacchett et al., *Int. J. Oncol.*, 3(5):781–788, 1993.

Culver et al., "In vivo gene transfer with retroviral vector-producer cells for treatment of experimental brain tumors", *Science*, 256:1550–1552, 1992.

Marshall, "Gene therapy's growing pains", *Science*, 269:1050–1055, 1995.

Neve, "Adenovirus vectors enter the brain", *Trends Neurosci*, 16(7):251–253, 1993.

Tishler et al., "Increases in sequence specific DNA binding by p53 following treatment with chemotherapeutic and DNA damaging agents", *Cancer Res.*, 53:2212–2216, 1993.

U.S. patent application Ser. No. 08/236,221 filed Apr. 29, 1994.

U.S. patent application Ser. No. 08/248,814 filed May 24, 1994.

U.S. patent application Ser. No. 08/335,461 filed Nov. 7, 1994.

Santhanam et al., "Repression of the interleukin 6 gene promoter by p53 and the retinoblastoma susceptibility gene product," *Proc. Natl. Acad. Sci. USA*, 88:7605–7609, 1991.

Eaves et al., "The biology of normal and neoplastic cells in CMI," Chronic Myeloid Leukemia, $2^{nd}$ Int'l Conference, Bologna, Italy, Oct. 4–7, 1992. From *Leukemia and Lymphoma*, 11:245–253 (1993).

Felgner et al., "Lipfection: a highly efficient, lipid-mediated DNA-transfection procedure," *Proc. Natl. Acad. Sci. USA*, 84:7413–7417, 1987.

Gjerset et al., "Dominant effect of transduced wild-type p53 over endogenous mutant p53 in sensitizing tumor cells to therapy," *Proceedings of the Am. Assoc. Can. Res.*, 36:21, 1995. (Abstract 123).

Gomez-Navarro et al., "Gene Therapy for Cancer," *European Journal of Cancer*, 35:867–885, 1999.

Green, "When the Products of Oncogenes and Anti-Oncogenes Meet," *Cell*, 56:1–3, 1989.

Harper et al. "the p21 cdk-interacting protien cip1 is a potent inhibitor of g1 cyclin-dependent kinases," *Cell*, 75:805–816, 1993.

Harper et al., "Enhancement of antitumor effects of p53 gene therapy by combination with DNA-damaging agents," *Cancer Gene Therapy*, vol. 3, 6, Conf. Suppl., S41–42, 1996.

*Hematology/Oncology Clinics of North America*, v. 4, n. 3, *Bone Marrow Transpantation*, edited by Stephen J. Foreman, M.D., 1990.

Hinds, "Biological Consequences of mutation of the p53 proto–oncogene," *UMI Dissertation Services*, Oct. 1989.

Huber et al., "Retroviral–Mediated Gene Therapy for the Treatment of Hepatocellular Carcinoma: An Innovative Approach for Cancer Therapy," *Proc. Natl. Acad. Sci. USA*, 88:8039–8043, 1991.

Kastan "p53 and other molecular controls of the response to DNA damage," *Adv. Exp. Med. Biol.*, 339:295–296, 1993.

Kastan, "Discussion of Dr. Kastan's presentation," *Adv. Exp. Med. Biol.*, 339:295–296, 1993.

Klinken et al., "Transcriptional and Post–Transcriptional Regulation of C–MYC C–MYB and p53 During Proliferation and Differentiation of Muring Erythroleukemia Cells Treated with DFMO and DMSO," *Exp. Cell Res.*, 178:185–198, 1988.

Kriegler et al., In: Gene Transfer and Expression: a laboratory manual, 1990.

Lord et al., "Macrophage Inflammatory Protein: Its Characteristics, Biological Properties and Role in the Regulation of Haemopoiesis," *International J. of Hematology*, 57:197–206, 1993.

Marx, "Cell Death Studies Yield Cancer Clues," *Science*, 259:760–761 (1993).

Orazi et al., "Frequent p53 overexpression in therapy related myelodysplastic syndromes and acute myeloid leukemias: an immunohistochemical study of bone marrow biopsies," *Mod. Path.*, 6:521–525, 1993.

Ryan et al., "Cell Cycle Analysis of p53–Induced Cell Death in Murine Erythroleukemia Cells," *Mol. Cell. Biol.*, 13:711–719, 1993.

Weinberg, "Tumor Suppressor Genes," *Science*, 254:1138–1146, 1991.

Fan et al., "p53 gene mutations are associated with decreased sensitivity of human lymphoma cells to DNA damaging agents," *Cancer Res.*, 54(22):5824–5830, 1994.

Fujiwara et al., "Induction of chemosensitivity in human lung cancer cells in vivo by adenovirus–mediated transfer of the wild–type p53 gene," *Surgical Forum*, 45:524–526, 1994.

Gobe et al., "Cell death by apoptosis following X–irradiation of the foetal and neonatal rat kidney," *Int. J. Radiat. Biol.*, 54:567–576, 1988.

Ijiri, "Apoptosis (cell death) induced in mouse bowel by 1,2–dimethylhydrazine, methylazoxymethanol acetate and y–rays," *Cancer Research*, 49:6342–6346, 1989.

Zhang et al., "High–efficiency gene transfer and high–level expression of wild–type p53 in human lung cancer cells mediated by recombinant adenovirus," *Cancer Gene Therapy*, 1:5–13, 1994.

Baker et al., "p53 Gene Mutations Occur in Combination with 17p Allelic Deletions as Late Events in Colorectal Tumorigenesis," *Cancer Research*, 50:7717–7722, Dec. 1990.

Chang et al., "Inhibition of intratracheal lung cancer development by systemic delivery of EIA," *Oncogene*, 13:1405–1412, 1996.

Carter et al., "Adenovirus Containing a Deletion of the Early Region 2A Gene Allows Growth of Adeno–Associated Virus with Decreased Efficiency," *Virology*, 191:473–476, 1992.

Chang et al., "Restoration of the G1 Checkpoint and the Apoptotic Pathway Mediated by Wild–type p53 Sensitizes Squamous Cell Carcinoma of the Head and Neck to Radiotherapy," *Arch Otolaryngol Head Neck Surg.*, 123:507–512, 1997.

Colicos et al., Construction of a recombinant adenovirus containing the denV gene from bacteriophase T4 which can partially restore the DNA repair deficiency in xeroderma pigmentosum fibroblasts, *Carcinogenesis*, 12(2):249–255, 1991.

Cai et al., "Stable expression of the wild–type p53 gene in human being lung cancer cells after retrovirus–mediated gene transfer," *Hum. Gene Ther.*, 4:617–24, 1993.

Davidson et al., "A model system for in vivo gene transfer into the central nervous system using adenoviral vector," *Nature Genetics*, 3:219–223, 1993.

Delauney et al., "A Stable Bifunctional Antisense Transcript Inhibiting Gene Expression in Transgenic Plants," *Proc. Natl. Acad. Sci. USA*, 85:4300–4304, 1988.

Dorigo et al., "Sensitization of rat glioblastoma multiforme to cisplatin in vivo following restoration of wild–type p53 function," *J. Neurosurg.*, 88:535–540, 1998.

Eliyahu et al., "p53—A potential suppressor gene?" *J. Cell. Biochem.*, UCLA Symposia on Mollecular and Cellular Biology, Abstracts, 19$^{th}$ Annual Meeting, Supplement 14C:264, #I 030, 1990.

Eliyahu et al., "Meth A Fibrosarcoma Cells Express Two Transforming Mutant p53 Species," *Oncogene*, 3:313–321, 1988.

Eliyahu et al., "Wild–type p53 Can Inhibit Oncogene–Mediated Focus Formation," *Proc. Nat. Acad. Sci. USA*, 85:8763–8767, Nov. 1989.

Finlay et al., "The p53 Proto–Oncogene Can Act as a Suppressor of Transformation," *Cell*, 57:1083–1093, Jun. 1989.

Fox; "Investigation of gene therapy begins," *Nature Biotechnology*, 18:143–144, 2000.

Fujiwara et al., "Therapeutic effect of a retroviral wild–type p53 expression vector in an orthotopic lung cancer model," *J. Natl. Cancer Inst.*, 86(19):1458–1462, 1994.

Gebhardt et al., "A Tumor Suppressor Proto–Oncogene p53 Can Block Progression Through the Cell Cycle," Association of American Physicians, American Society for Clinical Investigation, American Federation for Clinical Research, Subspecialty Meetings, Sheraton Washington Hotel, Washington, DC, May 6, 1990, p. 447A, Abstract.

Georges, et al, "Prevention of Orthotopic Human Lung Cancer Growth by Intratracheal Instillation of a Retroviral Antisense K–ras Construct," *Cancer Research*, 53:1743–1746, 1993.

Gomez–Foix, et al., "Adenovirus–Mediated Transfer of the Muscle Glycogen Phosphorylase Gene into Hepatocytes Confers Altered Regulation of Glycogen Metabolism," *The Journal of Biological Chemistry*, 267(35):25129–25134, 1992.

Gridley et al., "Evaluation of radiation effects against C6 glioma in combination with vaccinia virus–p53 gene therapy," *International J. Oncology*, 13:1093–1098, 1998.

Gutierrez et al., "Gene Therapy for Cancer," *The Lancet*, 339:715–721, 1992.

Hanania et al., "Genetic chemoprotection of hematopoietic cells and genetic chemosensitization of breast cancer cells in a mouse cancer gene therapy model," *Proc. Amer. Assoc. Cancer Res.*, vol. 37, #2362, Mar. 1996.

Hinds et al., "Mutation is Required to Activate the p53 Gene for Cooperation with the ras Oncogene and Transformation," *Journal of Virology*, 63(2):739–746, Feb. 1989.

Hinds et al., "The p53 Proto–Oncogene Can Suppress Transformation by Other Oncogenes, and Mutations in the Proto–Oncogene Can Activate the Gene for Transformation," *In: Common Mechanisms of Transformation by Small DNA Tumor Viruses*, Luis P. Villarreal (ed.), Chapter 7, pp. 83–101, 1989.

Hitt et al., "Adenovirus E1A under the Control of Heterologous Promoters: Wide Variation in E1A Expression Levels Has Little Effecton Virus Replication," *Virology*, 179:667–678, 1990.

Hodgson, "Advances in Vector Systems for Gene Therapy," *Exp. Opin. Ther. Patents*, 5(5):459–468, 1995.

Hollstein et al., "p53 Mutations in Human Cancers," *Science*, 253:49–53, 1991.

Huang et al., "Suppression of the Neoplastic Phenotype by Replacement of the RB Gene in Human Cancer Cells," *Science*, 242:1563–1566, Dec. 1988.

Jaffe et al., "Adenovirus–Mediated In Vivo Gene Transfer and Expression in Normal Rat Liver," *Nature Genetics*, 1:372–378, 1992.

Klessig et al., "Introduction, Stable Integration, and Controlled Expression of a Chimeric Adenovirus Gene Whose Product is Toxic to the Recipient Human Cell," *Molecular and Cellular Biology*, 4(7): 1354–1362, Jul. 1984.

Kmiec, "Investigators have been searching for ways to add corrective genes to cells harboring defective genes. A better strategy might be to correct the defects." *American Scientist*, 87:240–247, 1999.

Lamb and Crawford, "Characterization of the Human p53 Gene," *Molecular and Cellular Biology*, 6(5):1379–1385, May 1986.

Le Gal La Salle et al., "An Adenovirus Vector for Gene Transfer into Neurons and Glia in the Brain," *Science*, 259:988–990, 1993.

Lee et al., "Molecular basis of tumor suppression by the human retinoblastoma gene," UCLA Symposia on Mollecular and Cellular Biology, Abstracts, 19$^{th}$ Annual Meeting, Supplement 14C, #I 001, 1990.

Lesoon–Wood et al., "Systemic gene therapy with a liposome–p53 complex reduces the growth and metastases of a malignant human breast cancer in nude mice," *Proc. Annu. Meet. Am. Assoc. Cancer Res.*, vol. 36, pp. A2509, 1995.

Levine et al., "The p53 growth suppressor gene," UCLA Symposia on Mollecular and Cellular Biology, Abstracts, 19$^{th}$ Annual Meeting, Supplement 14C:264, #I 030, 1990.

Levine et al., "The p53 Growth Suppressing Gene Can Inhibit Transformation by Other Oncogenes," *The Journal of Cell Biology*, The American Society for Cell Biology, Twenty–ninth Annual Meeting, Houston, Texas, Nov. 5–9, 1989, Abstract 502.

Malkin et al., "Mutant p53 Confers Tumorigenicity to a Cell Line Lacking p53: Evidence for a Second p53 Function in Tumor Formation," *Blood*, 76(10, Suppl. 1):238a, Abstract 944, 1990.

Mercer et al., "Antiproliferative effects of wild type human p53," UCLA Symposia on Mollecular and Cellular Biology, Abstracts, 19$^{th}$ Annual Meeting, Supplement 14C:264, #I 029, 1990.

Mercer, "Cell Cycle Regulation and the p53 Tumor Suppressor Protein," *Critical Reviews in Eukaryotic Gene Expression*, 2(3):251–263, 1992.

Miller and Vile, "Targeted Vectors for Gene Therapy," *FASEB Journal*, 9:190–199, 1995.

Minna et al., "The molecular pathogenesis of lung cancer involves the accumulation of a large number of mutations in docminant oncogenes and multiple tumor suppressor genes (recessive oncogenes)," UCLA Symposia on Mollecular and Cellular Biology, Abstracts, 19$^{th}$ Annual Meeting, Supplement 14C:264, #I 003, 1990.

Miyake et al., "Enhancement of Chemosensitivity in Human Bladder Cancer Cells by Adenoviral–Mediated p53 Gene Transfer," *Anticancer Res.*, 18:3087–92, 1998.

Montenarh, "Biochemical, Immunological, and Functional Aspects of the Growth–Suppressor/Oncoprotein p53," *Critical Reviews in Oncogenesis*, (3):233–256, 1992.

Nguyen et al., "Delivery of the p53 tumor suppressor gene into lung cancer cells by an adenovirus/DNA complex," *Cancer Gene Therapy.*, 4(3):191–198, 1997.

Nielsen et al., "Efficacy of p53 adenovirus–mediated gene therapy against human breast cancer xenografts," *Pro. Annu. Meet. Am. Assoc. Cancer Res.*, vol. 37, pp. A2317, 1996.

Ogawa et al., "Novel Combination Therapy For Human Colon Cancer With Adenovirus–Mediated Wild–Type p53 Gene Transfer and DNA–Damaging Chemotherapeutic Agent," *Int. J. Cancer*, 73:367–370, 1997.

Pfarr et al., "Differential Effects of Polyadenylation Regions on Gene Expression in Mammalian Cells," *DNA*, 5(2):115–122, 1986.

Pirollo et al., "p53 mediated sensitization of squamous cell carcinoma of the head and neck to radiotherapy," *Oncogene*, 14:1735–46, 1997.

Prevec et al., "Use of Human Adenovirus–Based Vectors for Antigen Expression in Animals," *J. Gen. Virol.*, 70:429–434, 1989.

Rajan et al., "Simian Virus 40 Small–t Does Not Transactivate RNA Polymerase II Promoters in Virus Infections," *J. Viorology*, 65(12):6553–6561, 1991.

Romer and Friedman, "Mechanisms of action of the p53 tumor suppressor and prospects for cancer gene therapy by reconstitution of p53 function," *In: Annals of the New York Academy of Science, Gene Therapy for Neoplastic Disease*, 716:265–282 (1994).

Rosenfeld et al., "Adenovirus–Mediated Transfer of a Recombinant ál–Antitrypsin Gene to the Lung Epithelium In Vivo," *Science*, 252:431–434, 1991.

Rosenfeld et al., "In Vivo Transfer of the Human Cystic Fibrosis Transmembrane Conductance Regulator Gene to the Airway Epithelium," *Cell*, 68:143–155, 1992.

Ross et al., "Gene Therapy in the United States: A Five–Year Status Report," *Human Gene Therapy*, 7:1781–1790, 1996.

Roth, "Gene Replacement Strategies for Therapy and Prevention of Lung Cancer," *Proceedings Annual Meeting of American Assoc. Cancer Res.*, 35:692–3, 1994.

Roth, et al., "Retrovirus–Mediated Wild–Type p53 Gene Transfer to Tumors of Patients with Lung Cancer," *Nature Medicine*, 2:985–991, 1996.

Sager, "Tumor Suppressor Genes: The Puzzle and the Promise," *Science*, 246:1406–1412, Dec. 1989.

Santhanam et al., "Repression of the interleukin 6 gene promoter by p53 and the retinoblastoma susceptibility gene product," *Proc. Natl. Acad. Sci. USA*, 88:7605–7609, 1991.

Schuler et al., "A phase I study of adenovirus–mediated wild–type p53 gene transfer in patients with advanced non–small cell lung cancer,", *Human Gene Therapy*, 9:2075–2082, 1998.

Shenk, "Group C Adenoviruses as Vectors for Gene Therapy," in *Viral Vectors*, 1995, Academic Press.

Spitz et al., "Adenoviral mediated p53 gene therapy enhances radiation sensitivity of colorectal cancer cell lines," *Proc. Amer. Assoc. Cancer Res.*, vol. 37, #2366, Mar. 1996.

Stein et al, "Antisense oligonucleotides as therapeutic agents—is the bullet really magical?" *Science*, 261:1004–1012, 1993.

Stratford–Perricaudet, "Evaluation of the Transfer and Expression in Mice of an Enzyme–Encoding Gene Using a Human Adenovirus Vector," *Human Gene Therapy*, 1:241–256, 1990.

Stratford–Perricaudet, "Feasibility of Adenovirus–Mediated Gene Transfer In Vivo," *Bone Marrow Transplantation*, 9(Suppl. 1):151–152, 1992.

Stratford–Perricaudet, "Gene Transfer into Animals: the Promise of Adenovirus," *Human Gene Transfer*, 219:51–61, 1991.

Stratford–Perricaudet, "Widespread Long–Term Gene Transfer to Mouse Skeletal Muscles and Heart," *J. Clin. Invest.*, 90;626–630, 1992.

Takayama et al., "Growth suppression of lung cancer by recombinant adenovirus–mediated human p53 and p21 cDNA transfer," *Proceedings Annual Meeting, American Society of Clinical Oncology*, 16: A1597, 1997.

Tang et al., "Potential Application of Gene Therapy to Lung Cancer," *Seminars in Oncology*, 20(4):368–373, 1993.

Tseng and Brown, "Antisense oligonucleotide technology in the development of cancer therapeutics," *Cancer Gene Therapy*, 1(1):65–71, 1994.

Vogelstein et al., "Genetic alterations accumulate during colorectal tumorigenesis," UCLA Symposia on Molecular and Cellular Biology, Feb. 3–Mar. 11, 1990, Abstracts, 19$^{th}$ Annual Meeting, *J. Cell. Biochem.*, Supplement 14C:264, #I 004, 1990.

Wang and Finer, "Second–generation adenovirus vectors," *Nature Medicine*, 2:714–716, Jun. 6, 1996.

Wilkinson et al., "Constitutive and enhanced expression from the CMV major IE promoter in a defective adenovirus vector," *Nucleic Acids Research*, 20(9):2233–2239, 1992.

Xu et al., "Parental Gene Therapy with p53 Inhibits Human Breast Tumors In Vivo Through a Bystander Mechanism Without Evidence of Toxicity," *Human Gene Therapy*, 8:177–185, 1997.

Zhang and Roth, "Propagation of Recombinant p53 Adenovirus and Evaluation of its Effect on Human Lung Cancer Cell Lines," *The Fourth Meeting o the Molecular Basis of Cancer*, Jun. 1993.

Crown et al., "High–intensity chemotherapy with hematopoietic support in breast cancer," *Annals of the New York Academy of Sciences*, 698–378–388, 1993.

Rubin, "Cancer Principles and Practice of Oncology," (ed. 4) Lippincott–Raven NY, 258–261, 1993.

Rubin, "Cancer Principles and Practice of Oncology," (ed. 4) Lippincott–Raven NY, Ch. 16, 276–286, 1993.

* cited by examiner

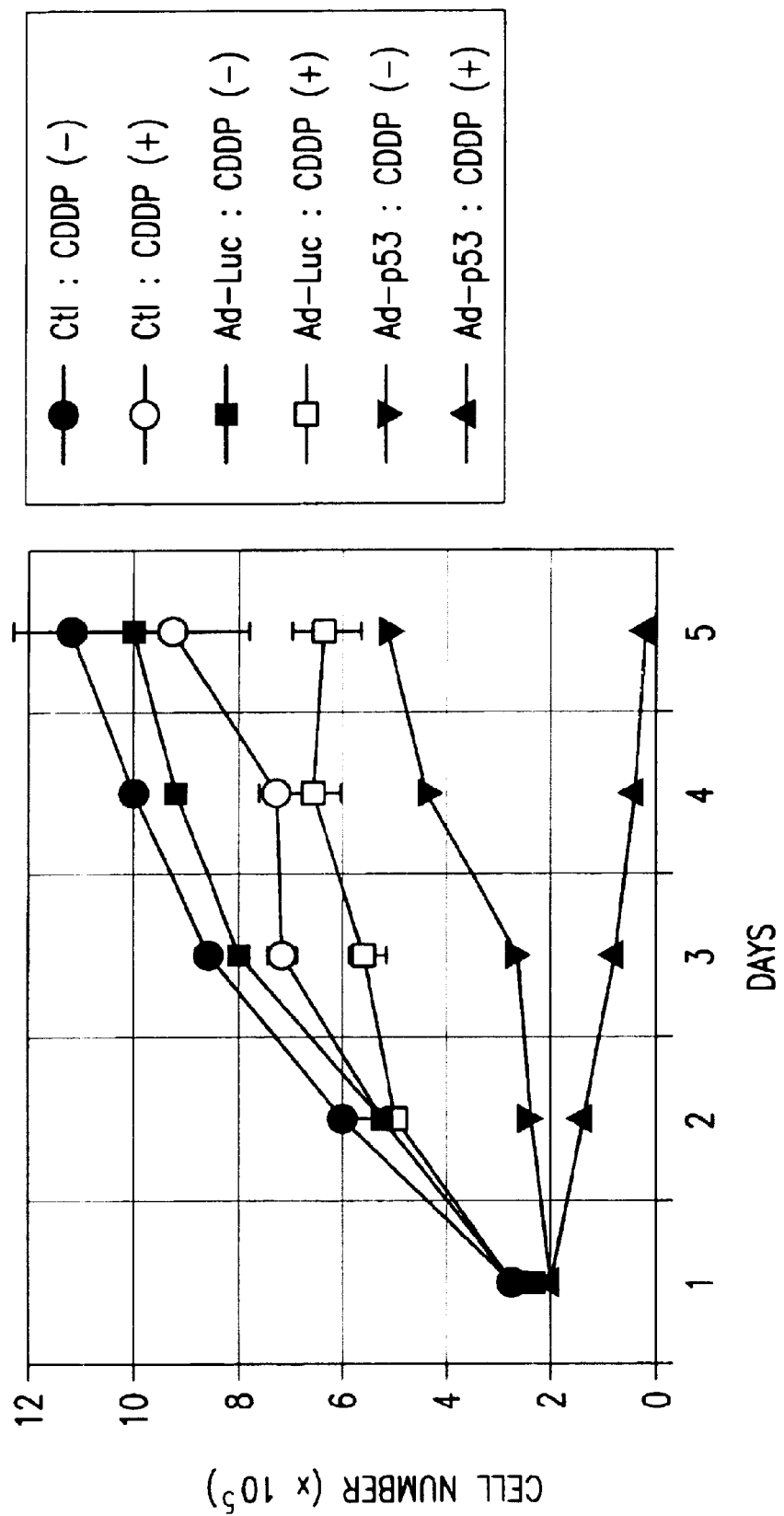

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

GGCCCACCCC CTTGGCTTC                                                      19

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

TTGTAACCAT TATAAGCTGC                                                     20

(2) INFORMATION FOR SEQ ID NO: 3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 3:

TCGTTTCTCA GCAGCTGTTG                                                     20

(2) INFORMATION FOR SEQ ID NO: 4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 4:

CATCTGAACT CAAAGCGTGG                                                     20

METHODS AND COMPOSITIONS COMPRISING DNA DAMAGING AGENTS AND P53

This is a continuation of co-pending application Ser. No. 08/233,002, filed Apr. 25, 1994, now U.S. Pat. No. 5,747,469, which is a continuation-in-part of co-pending U.S. patent application Ser. No. 08/145,826, filed Oct. 29, 1993 now U.S. Pat. No. 6,410,010; which is a continuation-in-part of U.S. patent application Ser. No. 07/960,513, filed Oct. 13, 1992; now abandoned which is a continuation-in-part of U.S. Ser. No. 07/665,538, filed Mar. 6, 1991 now abandoned; the entire text and figures of which disclosures are incorporated herein by reference without disclaimer.

The government owns rights in the present invention pursuant to NIH grants RO1 CA 45187 and CA 16672, and Training Grants CA 09611 and CA 45225.

BACKGROUND OF THE INVENTION

1. Field of the Invention

The present invention relates generally to the area of novel strategies for the improvement of chemotherapeutic intervention. In other aspects, the present invention provides novel methods and compositions that combine the potency of DNA damaging agents with the combined delivery of a tumor suppressor. The combination of DNA damaging factors with the heterologous expression of a tumor suppressor gene lead to a pronounced synergy over and above the actions of the individual components.

2. Description of Related Art

Current treatment methods for cancer, including radiation therapy, surgery, and chemotherapy, are known to have limited effectiveness. Lung cancer alone kills more than 140,000 people annually in the United States. Recently, age-adjusted mortality from lung cancer has surpassed that from breast cancer in women. Although implementation of smoking-reduction programs has decreased the prevalence of smoking, lung cancer mortality rates will remain high well into the 21st century. The rational development of new therapies for lung cancer will depend on an understanding of the biology of lung cancer at the molecular level.

It is now well established that a variety of cancers are caused, at least in part, by genetic abnormalities that result in either the over expression of one or more genes, or the expression of an abnormal or mutant gene or genes. For example, in many cases, the expression of oncogenes is known to result in the development of cancer. "Oncogenes" are genetically altered genes whose mutated expression product somehow disrupts normal cellular function or control (Spandidos et al., 1989).

Most oncogenes studied to date have been found to be "activated" as the result of a mutation, often a point mutation, in the coding region of a normal cellular gene, i.e., a "proto-oncogene", that results in amino acid substitutions in the expressed protein product. This altered expression product exhibits an abnormal biological function that takes part in the neoplastic process (Travali et al., 1990). The underlying mutations can arise by various means, such as by chemical mutagenesis or ionizing radiation. A number of oncogenes and oncogene families, including ras, myc, neu, raf, erb, src, fms, jun and abl, have now been identified and characterized to varying degrees (Travali et al., 1990; Bishop, 1987).

During normal cell growth, it is thought that growth-promoting proto-oncogenes are counterbalanced by growth-constraining tumor suppressor genes. Several factors may contribute to an imbalance in these two forces, leading to the neoplastic state. One such factor is mutations in tumor suppressor genes (Weinberg, 1991).

An important tumor suppressor gene is the gene encoding the cellular protein, p53, which is a 53 kD nuclear phosphoprotein that controls cell proliferation. Mutations to the p53 gene and allele loss on chromosome 17p, where this gene is located, are among the most frequent alterations identified in human malignancies. The p53 protein is highly conserved through evolution and is expressed in most normal tissues. Wild-type p53 has been shown to be involved in control of the cell cycle (Mercer, 1992), transcriptional regulation (Fields et al., 1990, and Mietz et al., 1992), DNA replication (Wilcock and Lane, 1991, and Bargonetti et al., 1991), and induction of apoptosis (Yonish-Rouach et al., 1991, and, Shaw et al., 1992).

Various mutant p53 alleles are known in which a single base substitution results in the synthesis of proteins that have quite different growth regulatory properties and, ultimately, lead to malignancies (Hollstein et al., 1991). In fact, the p53 gene has been found to be the most frequently mutated gene in common human cancers (Hollstein et al., 1991; Weinberg, 1991), and is particularly associated with those cancers linked to cigarettes smoke (Hollstein et al., 1991; Zakut-Houri et al., 1985). The overexpression of p53 in breast tumors has also been documented (Casey et al., 1991).

One of the most challenging aspects of gene therapy for cancer relates to utilization of tumor suppressor genes, such as p53. It has been reported that transfection of wild-type p53 into certain types of breast and lung cancer cells can restore growth suppression control in cell lines (Casey et al., 1991; Takahasi et al., 1992). Although DNA transfection is not a viable means for introducing DNA into patients' cells, these results serve to demonstrate that supplying wild type p53 to cancer cells having a mutated p53 gene may be an effective treatment method if an improved means for delivering the p53 gene could be developed.

Gene delivery systems applicable to gene therapy for tumor suppression are currently being investigated and developed. Virus-based gene transfer vehicles are of particular interest because of the efficiency of viruses in infecting actual living cells, a process in which the viral genetic material itself is transferred. Some progress has been made in this regard as, for example, in the generation of retroviral vectors engineered to deliver a variety of genes. However, major problems are associated with using retroviral vectors for gene therapy since their infectivity depends on the availability of retroviral receptors on the target cells, they are difficult to concentrate and purify, and they only integrate efficiently into replicating cells.

Tumor cell resistance to chemotherapeutic drugs represents a major problem in clinical oncology. NSCLC accounts for at least 80% of the cases of lung cancer; patients with NSCLC are, however, generally unresponsive to chemotherapy (Doyle, 1993). One goal of current cancer research is to find ways to improve the efficacy of gene replacement therapy for cancer by investigating interaction between the gene product and chemotherapeutic drugs. The herpes simplex-thymidine kinase (HS-tK) gene, when delivered to brain tumors by a retroviral vector system, successfully induced susceptibility to the antiviral agent ganciclovir (Culver, et al., 1992). The HS-tK gene product is an exogenous viral enzyme, whereas the wt-p53 protein is expressed in normal tissues, suggesting that the modulation of chemoresistance by alterations in wt-p53 expression might be an alternative approach using a pathway mediated by an endogenous genetic program.

An adenovirus system has potential advantages for gene delivery in vivo, such as ease of producing high titer virus, high infection efficiency, and infectivity for many types of cells. The stability and duration of expression of the introduced gene are still controversial, however. The increase in p53 levels in cells that are sensitive to chemotherapeutic drugs can occur within 6 hours after DNA-damaging stimuli (Fritsche, et al., 1993, Zhan, et al., 1993), although increased p53 DNA binding activity can be reversed over the course of 4 hours if the stimulus is removed (Tishler, et al., 1993) Therefore, a high level of p53 expression can be maintained even after cessation of drug exposure. The expression of wt-p53 protein by Ad-p53 peaks at postinfection day 3 (14-fold greater than endogenous wild type) and decreases to a low level by day 9 (Zhang, et al., 1993). This suggests that a transiently high level of wt-p53 expression is sufficient to initiate the cytotoxic program in the cancer cell.

p53 has an important role as a determinant of chemosensitivity in human lung cancer cells. A variety of treatment protocols, including surgery, chemotherapy, and radiotherapy, have been tried for human NSCLC, but the long-term survival rate remains unsatisfactory. What is needed is a combination therapy that is used alone or as an effective adjuvant treatment to prevent local recurrence following primary tumor resection or as a treatment that could be given by intralesional injections in drug-resistant primary, metastatic, or locally recurrent lung cancer. Compositions and methods are also needed to developed, explore and improve clinical applicability of novel compositions for the treatment of cancer. Furthermore these methods and compositions must prove their value in an in vivo setting.

SUMMARY OF THE INVENTION

The present invention addresses the need for improved therapeutic preparations for use in killing cells by combining the effects of a tumor suppressor gene or protein and a DNA damaging agent or factor. The present invention also provides compositions and methods, including those that use viral mediated gene transfer, to promote expression of a wild-type tumor suppressor gene, such as p53, in target cells and to deliver an agent or factor that induces DNA damage. The inventors surprisingly found that using the compositions disclosed herein, they were able to induce programmed cell death, also known as apoptosis, in a very significant number of target cells.

Using the present invention the inventors have demonstrated a remarkable effect in controlling cell growth and in particular, tumor cell growth. Tumor cell formation and growth, also known as "transformation", describes the formation and proliferation of cells that have lost their ability to control cellular division, that is, they are cancerous. It is envisioned that a number of different types of transformed cells are potential targets for the methods and compositions of the present invention, such as: sarcomas, melanomas, lymphomas, and a wide variety of solid tumors and the like. Although any tissue having malignant cell growth may be a target, lung and breast tissue are preferred targets. The present inventors disclose herein that a p53-expressing recombinant delivery vector was able to markedly reduce the growth rate of cells when used in conjunction with a DNA damaging agent.

The invention provides, in certain embodiments, methods and compositions for killing a cell or cells, such as a malignant cell or cells, by contacting or exposing a cell or population of cells with a p53 protein or gene and one or more DNA damaging agents in a combined amount effective to kill the cell(s). Cells that may be killed using the invention include, e.g., undesirable but benign cells, such as benign prostate hyperplasia cells or over-active thyroid cells; cells relating to autoimmune diseases, such as B cells that produce antibodies involved in arthritis, lupus, myasthenia gravis, squamous metaplasia, dysplasia and the like. Although generally applicable to killing all undesirable cells, the invention has a particular utility in killing malignant cells. "Malignant cells" are defined as cells that have lost the ability to control the cell division cycle, as leads to a "transformed" or "cancerous" phenotype.

To kill cells, such as malignant or metastatic cells, using the methods and compositions of the present invention, one would generally contact a "target" cell with a p53 protein or gene and at least one DNA damaging agent in a combined amount effective to kill the cell. This process may involve contacting the cells with the p53 protein or gene and the DNA damaging agent(s) or factor(s) at the same time. This may be achieved by contacting the cell with a single composition or pharmacological formulation that includes both agents, or by contacting the cell with two distinct compositions or formulations, at the same time, wherein one composition includes the p53 protein or gene and the other includes the DNA damaging agent.

Naturally, it is also envisioned that the target cell may be first exposed to the DNA damaging agent(s) and then contacted with a p53 protein or gene, or vice versa. However, in embodiments where the DNA damaging factor and p53 are applied separately to the cell, one would generally ensure that a significant period of time did not expire between the time of each delivery, such that the DNA damaging agent and p53 would still be able to exert an advantageously combined effect on the cell. In such instances, it is contemplated that one would contact the cell with both agents within about 12–24 hours of each other, and more preferably within about 6–12 hours of each other, with a delay time of only about 12 hours being most preferred.

The terms "contacted" and "exposed", when applied to a cell, are used herein to describe the process by which a tumor suppressor gene or protein, such as p53, and a DNA damaging agent or factor are delivered to a target cell or are placed in direct juxtaposition with the target cell. TO achieve cell killing, both agents are delivered to a cell in a combined amount effective to kill the cell, i.e., to induce programmed cell death or apoptosis. The terms, "killing", "programmed cell death" and "apoptosis" are used interchangeably in the present text to describe a series of intracellular events that lead to target cell death. The process of cell death involves the activation of intracellular proteases and nucleases that lead to, for example, cell nucleus involution and nuclear DNA fragmentation. An understanding of the precise mechanisms by which various intracellular molecules interact to achieve cell death is not necessary for practicing the present invention.

DNA damaging agents or factors are defined herein as any chemical compound or treatment method that induces DNA damage when applied to a cell. Such agents and factors include radiation and waves that induce DNA damage, such as, γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP), and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a p53 protein or gene is particularly preferred as this compound.

Any method may also be used to contact a cell with a p53 protein, so long as the method results in increased levels of functional p53 protein within the cell. This includes both the direct delivery of a p53 protein to the cell and the delivery of a gene or DNA segment that encodes p53, which gene will direct the expression and production of p53 within the cell. In that protein delivery is subject to such drawbacks as protein degradation and low cellular uptake, it is contemplated that the use of a recombinant vector that expresses a p53 protein will provide particular advantages.

A wide variety of recombinant plasmids and vectors may be engineered to expresses a p53 protein and so used to deliver p53 to a cell. These include, for example, the use of naked DNA and p53 plasmids to directly transfer genetic material into a cell (Wolfe et al., 1990); formulations of p53-encoding DNA trapped in liposomes (Ledley et al., 1987) or in proteoliposomes that contain viral envelope receptor proteins (Nicolau et al., 1983); and p53-encoding DNA coupled to a polylysine-glycoprotein carrier complex.

The use of recombinant viruses engineered to express p53 is also envisioned. A variety of viral vectors, such as retroviral vectors, herpes simplex virus (U.S. Pat. No. 5,288, 641, incorporated herein by reference), cytomegalovirus, and the like may be employed, as described by Miller (Miller, 1992); as may recombinant adeno-associated virus (AAV vectors), such as those described by U.S. Pat. No. 5,139,941, incorporated herein by reference; and, particularly, recombinant adenoviral vectors. Techniques for preparing replication-defective infective viruses are well known in the art, as exemplified by Ghosh-Choudhury & Graham (1987); McGrory et al. (1988); and Gluzman et al. (1982), each incorporated herein by reference.

To kill a cell in accordance with the present invention, one would generally contact the cell with a p53 protein or gene and a DNA damaging agent in a combined amount effective to kill the cell. The term "in a combined amount effective to kill the cell" means that the amount of p53 and DNA damaging agents are sufficient so that, when combined within the cell, the cell is induced to undergo apoptosis. Although not required in all embodiments, the combined effective amount of p53 and DNA damaging agent will preferably be an amount that induces significantly more cell death than the use of either element alone, and most preferably, the combined effective amount will be an amount that induces synergistic cell death in comparison to the effects observed using either element alone.

A number of in vitro parameters may be used to determine the effect produced by the compositions and methods of the present invention. These parameters include, for example, the observation of net cell numbers before and after exposure to the compositions described herein, as well as the size of multicellular tumor spheroids formed, such as those colonies formed in tissue culture. In vitro cell killing is particularly shown in Example 7 of the present disclosure. Alternatively, one may measure parameters that are indicative of a cell that is undergoing programmed cell death, such as, the fragmentation of cellular genomic DNA into nucleosome size fragments, generally identified by separating the fragments by agarose gel electrophoresis, staining the DNA, and comparing the DNA to a DNA size ladder. Nucleosome size fragments are identified as a progressive steps or ladders of monomers and multimers having a base unit of about 200 basepairs.

Similarly, a "therapeutically effective amount" is an amount of a p53 protein or gene and DNA damaging agent that, when administered to an animal in combination, is effective to kill cells within the animal. This is particularly evidenced by the killing of cancer cells, such as lung, breast or colon cancer cell, within an animal or human subject that has a tumor. "Therapeutically effective combinations" are thus generally combined amounts of p53 and DNA damaging agents that function to kill more cells than either element alone, and preferably, combined amounts that bring about a synergistic reduction in tumor burden.

Studying certain in vivo and ex vivo parameters of cell death are therefore also effective means by which to assess the effectiveness of the composition and methods of the invention. For example, observing effects on the inhibition of tumorigenicity, as measured by TdT expression of frozen tissue sections or by using other staining methods and target antigens, as known to skilled pathologists. Naturally, other means of determining tumor mass, growth, and viability may also be used to assess the killing of target cells. In particular, one may assess the effects in various animal model systems of cancer, including those in which human cancer cells are localized within the animal. Animal models of cancer, unlike those of AIDS, are known to be highly predictive of human treatment regimens (Roth et al., editors (1989)). One exemplary embodiment of a predictive animal model is that in which human small-cell lung cancer cells (H358 cells) are grown subcutaneously. Using this system, the inventors have shown that p53-bearing adenovirus instilled intratumorally, along with the co-administration of a chemotherapeutic agent, gives rise to a surprisingly effective tumor reduction.

A particularly preferred method of delivering a p53 protein to a cell is to contact the cell with a recombinant adenovirus virion or particle that includes a recombinant adenoviral vector comprising a p53 expression region positioned under the control of a promoter capable of directing the expression of p53 in the given cell type.

The p53 expression region in the vector may comprise a genomic sequence, but for simplicity, it is contemplated that one will generally prefer to employ a p53 cDNA sequence as these are readily available in the art and more easily manipulated. In addition to comprising a p53 expression unit and a promoter region, the vector will also generally comprise a polyadenylation signal, such as an SV40 early gene, or protamine gene, polyadenylation signal, or the like.

In preferred embodiments, it is contemplated that one will desire to position the p53 expression region under the control of a strong constitutive promoter such as a CMV promoter, viral LTR, RSV, or SV40 promoter, or a promoter associated with genes that are expressed at high levels in mammalian cells such as elongation factor-1 or actin promoters. All such variants are envisioned to be useful with the present invention. Currently, a particularly preferred promoter is the cytomegalovirus (CMV) IE promoter.

The p53 gene or cDNA may be introduced into a recombinant adenovirus in accordance with the invention simply by inserting or adding the p53 coding sequence into a viral genome. However, the preferred adenoviruses will be replication defective viruses in which a viral gene essential for replication and/or packaging has been deleted from the adenoviral vector construct, allowing the p53 expression region to be introduced in its place. Any gene, whether essential (e.g., E1A, E1B, E2 and E4) or non-essential (e.g., E3) for replication, may be deleted and replaced with p53. Particularly preferred are those vectors and virions in which the E1A and E1B regions of the adenovirus vector have been deleted and the p53 expression region introduced in their place, as exemplified by the genome structure of FIG. 1.

Techniques for preparing replication defective adenoviruses are well known in the art, as exemplified by Ghosh-Choudhury and Graham (1987); McGrory et al. (1988), and Gluzman et al., each incorporated herein by reference. It is also well known that various cell lines may be used to propagate recombinant adenoviruses, so long as they complement any replication defect which may be present. A preferred cell line is the human 293 cell line, but any other cell line that is permissive for replication, i.e., in the preferred case, which expresses E1A and E1B may be employed. Further, the cells can be propagated either on plastic dishes or in suspension culture, in order to obtain virus stocks thereof.

The invention is not limited to E1-lacking virus and E1-expressing cells alone. Indeed, other complementary combinations of viruses and host cells may be employed in connection with the present invention. Virus lacking functional E2 and E2-expressing cells may be used, as may virus lacking functional E4 and E4-expressing cells, and the like. Where a gene which is not essential for replication is deleted and replaced, such as, for example, the E3 gene, this defect will not need to be specifically complemented by the host cell.

Other than the requirement that the adenovirus vectors be engineered to express p53, the nature of the initial adenovirus is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which there is significant amount of biochemical and genetic information known, and which has historically been used for most constructions employing adenovirus as a vector.

The methods and compositions of the present invention are equally suitable for killing a cell or cells both in vitro and in vivo. When the cells to be killed are located within an animal, e.g., lung, breast or colon cancer cells or other cells bearing a p53 mutation, both the p53 protein or gene and the DNA damaging agent will be administered to the animal in a pharmacologically acceptable form. The term "a pharmacologically acceptable form", as used herein, refers to both the form of any composition that may be administered to an animal, and also the form of contacting an animal with radiation, i.e., the manner in which an area of the animals body is irradiated, e.g., with irradiation, X-rays, let UV-irradiation, microwaves, electronic emissions, and the like. The use of DNA damaging radiation and waves is known to those skilled in the art of irradiation therapy.

The present invention also provides advantageous methods for treating cancer that, generally, comprise administering to an animal or human patient with cancer a therapeutically effective combination of a p53 protein or gene and a DNA damaging agent. This may be achieved using a recombinant virus, particularly an adenovirus, that carries a vector capable of expressing p53 in the cells of the tumor. The p53 gene delivering composition would generally be administered to the animal, often in close contact to the tumor, in the form of a pharmaceutically acceptable composition. Direct intralesional injection of a therapeutically effective amount of a p53 gene, such as housed within a recombinant virus, into a tumor site is one preferred method. However, other parenteral routes of administration, such as intravenous, percutaneous, endoscopic, or subcutaneous injection are also contemplated.

In treating cancer according to the invention one would contact the tumor cells with a DNA damaging agent in addition to the p53 protein or gene. This may be achieved by irradiating the localized tumor site with DNA damaging radiation such as X-rays, UV-light, γ-rays or even microwaves. Alternatively, the tumor cells may be contacted with the DNA damaging agent by administering to the animal a therapeutically effective amount of a pharmaceutical composition comprising a DNA damaging compound, such as, adriamycin, 5-fluorouracil, etoposide, camptothecin, actinomycin-D, mitomycin C, or more preferably, cisplatin. The DNA damaging agent may be prepared and used as a combined therapeutic composition, or kit, by combining it with a p53 protein, gene or gene delivery system, as described above.

The surprising success of the present invention is evidenced by the finding that using Ad5CMV-p53 virus in combination with cisplatin yielded profound results in studies using a nude mouse model. The combined virus-DNA damage therapy regimen significantly inhibited the tumorigenicity of H358 cells, a cell that normally produces a significant tumor mass. The tumorigenicity of the lung cancer cells was inhibited through the treatment by Ad5CMV-p53, but not by the control virus expressing luciferase, indicating that the p53 protein in combination with a DNA-damaging agent has great therapeutic efficacy.

A number of methods for delivering chemotherapeutic formulations, including DNA expression constructs, into eukaryotic cells are known to those of skill in the art. In light of the present disclosure, the skilled artisan will be able to deliver both DNA damaging agents and p53 proteins or genes to cells in many different effective ways.

For in vivo delivery of DNA, the inventors envision the use of any gene delivery system, such as viral- and liposome-mediated transfection. As used herein, the term "transfection", is used to describe the targeted delivery of DNA to eukaryotic cells using delivery systems, such as, adenoviral, AAV, retroviral, or plasmid delivery gene transfer methods. The specificity of viral gene delivery may be selected to preferentially direct the gene to a particular target cell, such as by using viruses that are able to infect particular cell types. Naturally, different viral host ranges will dictate the virus chosen for gene transfer, as well as the likely tumor suppressor gene to be expressed for killing a given malignant cell type.

It is also envisioned that one may provide the DNA damaging chemotherapeutic agent through a variety of means, such as by using parenteral delivery methods such as intravenous and subcutaneous injection, and the like. Such methods are known to those of skill in the art of drug delivery, and are further described herein in the sections regarding pharmaceutical preparations and treatment.

For in vitro gene delivery, a variety of methods may be employed, such as, e.g., calcium phosphate- or dextran sulfate-mediated transfection; electroporation; glass projectile targeting; and the like. These methods are known to those of skill in the art, with the exact compositions and execution being apparent in light of the present disclosure.

Other embodiments concern compositions, including pharmaceutical formulations, comprising a p53 protein or gene in combination with a DNA damaging agent, such as cisplatin. In such compositions, the p53 may be in the form a DNA segment, recombinant vector or recombinant virus that is capable of expressing a p53 protein in an animal cell. These compositions, including those comprising a recombinant viral gene delivery system, such as an adenovirus particle, may be formulated for in vivo administration by dispersion in a pharmacologically acceptable solution or buffer. Preferred pharmacologically acceptable solutions include neutral saline solutions buffered with phosphate, lactate, Tris, and the like.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

Preferred pharmaceutical compositions of the invention are those that include, within a pharmacologically acceptable solution or buffer, a p53 protein, or more preferably a p53 gene, in combination with a chemotherapeutic DNA damaging agent. Exemplary chemotherapeutic agents are adriamycin, 5-fluorouracil, camptothecin, actinomycin-D, hydrogen peroxide, mitomycin C, cisplatin (CDDP), and etoposide (VP-16), with the use of cisplatin being particularly preferred.

Still further embodiments of the present invention are kits for use in killing cells, such as malignant cells, as may be formulated into therapeutic kits for use in cancer treatment. The kits of the invention will generally comprise, in suitable container means, a pharmaceutical formulation of a recombinant vector that is capable of expressing a p53 protein in an animal cell, and a pharmaceutical formulation of a DNA damaging agent. The recombinant vectors and DNA damaging agents may be present within a single container, or these components may be provided in distinct or separate container means. In a preferred embodiment, the recombinant vector will be a recombinant p53-expressing adenoviral vector present within an adenovirus particle and the DNA damaging agent will be cisplatin.

The components of the kit are preferably provided as a liquid solution, or as a dried powder. When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A, 3B, 3C and 3D are a series of phase contrast images (×400) of 293 cells. FIGS. 3A, 3B, 3C and 3D are four panels of a single page figure. FIG. 2A, before transfection; FIG. 3B, negative control on day 12 posttransfection; FIG. 3C, onset of CPE on day 12 posttransfection; FIG. 3D, completion of CPE on day 14 post-transfection.

FIGS. 4A, 4B, 4C and 4D are a series of immunohistological images of H358 cells. FIGS. 4A, 4B, 4C and 4D are four panels of a single page figure. Infectivity of Ad5CMV-p53 in H358 cells. H358 cells were infected with Ad5CMV-p53 or Ad5/RSV/GL2 at 50 PFU/cell for 24 h. Medium alone was used as a mock infection. The infected cells were analyzed by immunostainings. FIG. 4A is a mock infection probed with anti-p53 antibody. FIG. 4B are cells infected with the Ad5/RSV/GL2 control and probed with anti-p53 antibody. FIG. 4C are Ad5CMV-p53 infected cells probed with an unrelated antibody (MOPC-21). FIG. 4D are cells Ad5CMV-p53 infection probed with anti-p53 antibody. The anti-p53 antibody used was Pab 1801, and the avidin-biotin method was used for staining.

FIGS. 9A, 9B, 9C, and 9D are four panels of a single figure. The mice were sacrificed at the end of the 6-week posttreatment period. The lung and mediastinum tissues were dissected for evaluation of tumor formation. FIG. 9A is a sample of mediastinal block from a normal nude mice; FIG. 9B is the mediastinal block sample from the vehicle (PBS)-treated mice; FIG. 9C is the mediastinal block sample from the Ad5CMV-p53-treated mice; FIG. 9D is the mediastinal block sample from the Ad5/RSV/GL2-treated mice. Arrows indicate the tumor masses.

FIG. 10B. 24-hour exposure to CDDP on the growth rates of parental, Ad-Luc-infected, and Ad-p53-infected H358 cells. Cells were exposed to CDDP (FIG. 10A) continuously or (FIG. 10B) for 24 hours followed by recovery in drug-free medium. Cells that remained as an attached monolayer were assessed for viability over 5 days by measuring trypan blue uptake. The mean +/- SE is shown. The day 5 cell number for the Ad-p53:CDDP group differs significantly from all other groups for both A and B ($p<0.05$ by Student's t-test)

DETAILED DESCRIPTION OF THE PREFERRED EMBODIMENTS

Figure 1:
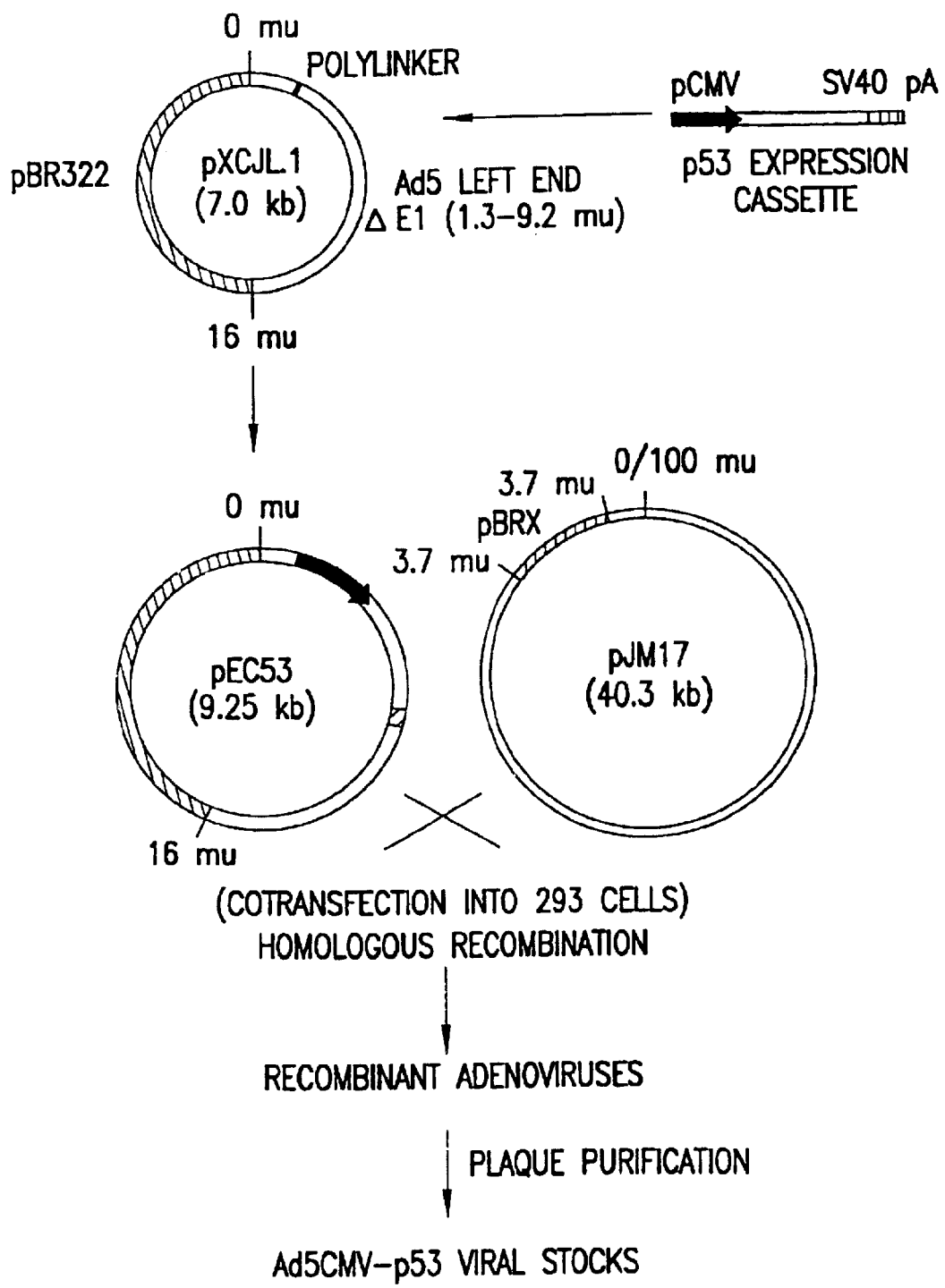
FIG. 1. Scheme for generation of recombinant p53 adenovirus. The p53 expression cassette was inserted between the Xba I and Cla I sites of pXCJL.1. The p53 expression vector (pEC53) and the recombinant plasmid pJM17 were cotransfected into 293 cells. The transfected cells were maintained in medium until the onset of the cytopathic effect. Identification of newly generated p53 recombinant adenoviruses (Ad5CMV-p53) by PCR analysis of the DNA using DNA templates prepared from the CPE supernatants treated with Proteinase K and phenol extraction.

A. Molecular Events in Lung Cancer Development

Studies carried out by the present inventors has identified critical molecular events leading to the development and progression of cancer. This enabled the inventors to develop new methods for restoring certain normal protein functions so that the malignant phenotype can be suppressed in vivo.

The most common lung cancer histologies (80%) are grouped under the term non-small-cell lung cancer (NSCLC) and include squamous, adenocarcinoma, and large-cell undifferentiated. Many of the current data on the molecular biology of lung cancer come from the study of the more uncommon small-cell lung cancer (SCLC). SCLC can be distinguished from NSCLC by the neuroendocrine features of the cells; SCLC is very responsive to chemotherapy but recurs rapidly after treatment. NSCLC also may serve as a model for other carcinogen-induced epithelial cancers. The approaches and observations developed in this study may be applicable to other types of epithelial cancers.

Abundant evidence has accumulated that the process of malignant transformation is mediated by a genetic paradigm. The major lesions detected in cancer cells occur in dominant oncogenes and tumor suppressor genes. Dominant oncogenes have alterations in a class of genes called proto-oncogenes, which participate in critical normal cell functions, including signal transduction and transcription. Primary modifications in the dominant oncogenes that confer the ability to transform include point mutations, translocations, rearrangements, and amplification. Tumor suppressor genes appear to require a homozygous loss of function, by mutation, deletion, or a combination of these for transformation to occur. Some tumor suppressor genes appear to play a role in the governance of proliferation by regulation of transcription. Modification of the expression of dominant and tumor suppressor oncogenes is likely to influence certain characteristics of cells that contribute to the malignant phenotype.

Despite increasing knowledge of the mechanisms involved in oncogene-mediated transformation, little progress has occurred in developing therapeutic strategies that specifically target oncogenes and their products. Initially, research in this area was focused on dominant oncogenes, as these were the first to be characterized. DNA-mediated gene transfer studies showed acquisition of the malignant phenotype by normal cells following the transfer of DNA from malignant human tumors.

B. p53 and p53 Mutations in Cancer

P53 is currently recognized as a tumor suppressor gene (Montenarh, 1992). High levels have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers. (Mercer, 1992). It is mutated in over 50% of human NSCLC (Hollestein et al., 1991) and in a wide spectrum of other tumors.

The p53 gene encodes a 375-amino-acid phosphoprotein that can form complexes with host proteins such as large-T antigen and E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus p53 can act as a negative regulator of cell growth (Weinberg, 1991) and may directly suppress uncontrolled cell growth or indirectly activate genes that suppress this growth. Thus, absence or inactivation of wild type p53 may contribute to transformation. However, some studies indicate that the presence of mutant p53 may be necessary for full expression of the transforming potential of the gene.

Although wild-type p53 is recognized as a centrally important growth regulator in many cell types, its genetic and biochemical traits appear to have a role as well. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not-mutant, p53 into human lung cancer cell lines (Takahasi et al., 1992). The p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects.

It is thus possible that the treatment of p53-associated cancers with wild type p53 may reduce the number of malignant cells. However, studies such as those described above are far from achieving such a goal, not least because DNA transfection cannot be employed to introduce DNA into cancer cells within a patients' body.

C. Gene Therapy Techniques

There have been several experimental approaches to gene therapy proposed to date, but each suffer from their particular drawbacks (Mulligan, 1993). As mentioned above, basic transfection methods exist in which DNA containing the gene of interest is introduced into cells non-biologically, for example, by permeabilizing the cell membrane physically or chemically. Naturally, this approach is limited to cells that can be temporarily removed from the body and can tolerate the cytotoxicity of the treatment, i.e. lymphocytes. Liposomes or protein conjugates formed with certain lipids and amphophilic peptides can be used for transfection, but the efficiency of gene integration is still very low, on the order of one integration event per 1,000 to 100,000 cells, and expression of transfected genes is often limited to days in proliferating cells or weeks in non proliferating cells. DNA transfection is clearly, therefore, not a suitable method for cancer treatment.

A second approach capitalizes on the natural ability of viruses to enter cells, bringing their own genetic material with them. Retroviruses have promise as gene delivery vectors due to their ability to integrate their genes into the host genome, transferring a large amount of foreign genetic material, infecting a broad spectrum of species and cell types and of being packaged in special cell-lines. However, three major problems hamper the practical use of retrovirus vectors. First, retroviral infectivity depends on the availability of the viral receptors on the target surface. Second, retroviruses only integrate efficiently into replicating cells. And finally, retroviruses are difficult to concentrate and purify.

D. Adenovirus Constructs for Use in Gene Therapy

Human adenoviruses are double-stranded DNA tumor viruses with genome sizes of approximate 36 kb (Tooza, 1981). As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991a).

As only a small portion of the viral genome appears to be required in cis (Tooza, 1981), adenovirus-derived vectors offer excellent potential for the substitution of large DNA fragments when used in connection with cell lines such as 293 cells. Ad5-transformed human embryonic kidney cell line (Graham, et al., 1977) have been developed to provide the essential viral proteins in trans. The inventors thus reasoned that the characteristics of adenoviruses rendered them good candidates for use in targeting cancer cells in vivo (Grunhaus & Horwitz, 1992).

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of Adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, 1992).

In general adenovirus gene transfer systems are based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells (Stratford-Perricaudet and Perricaudet, 1991a). Surprisingly persistent expression of transgenes following adenoviral infection has also been reported.

Adenovirus-mediated gene transfer has recently been investigated as a means of mediating gene transfer into eukaryotic cells and into whole animals. For example, in treating mice with the rare recessive genetic disorder ornithine transcarbamylase (OTC) deficiency, it was found that adenoviral constructs could be employed to supply the normal OTC enzyme. Unfortunately, the expression of normal levels of OTC was only achieved in 4 out of 17 instances (Stratford-Perricaudet et al., 1991b). Therefore, the defect was only partially corrected in most of the mice and led to no physiological or phenotypic change. These type of results therefore offer little encouragement for the use of adenoviral vectors in cancer therapy.

Attempts to use adenovirus to transfer the gene for cystic fibrosis transmembrane conductance regulator (CFTR) into the pulmonary epithelium of cotton rats have also been partially successful, although it has not been possible to assess the biological activity of the transferred gene in the epithelium of the animals (Rosenfeld et al., 1992). Again, these studies demonstrated gene transfer and expression of the CFTR protein in lung airway cells but showed no physiologic effect. In the 1991 Science article, Rosenfeld et al. showed lung expression of $\alpha$1-antitrypsin protein but again showed no physiologic effect. In fact, they estimated that the levels of expression that they observed were only about 2% of the level required for protection of the lung in humans, i.e., far below that necessary for a physiologic effect.

The gene for human $\alpha_1$-antitrypsin has been introduced into the liver of normal rats by intraportal injection, where it was expressed and resulted in the secretion of the introduced human protein into the plasma of these rats (Jaffe et al., 1992). However, and disappointingly, the levels that were obtained were not high enough to be of therapeutic value.

These type of results do not demonstrate that adenovirus is able to direct the expression of sufficient protein in recombinant cells to achieve a physiologically relevant effect, and they do not, therefore, suggest a usefulness of the adenovirus system for use in connection with cancer therapy. Furthermore, prior to the present invention, it was thought that p53 could not be incorporated into a packaging cell, such as those used to prepare adenovirus, as it would be toxic. As E1B of adenovirus binds to p53, this was thought to be a further reason why adenovirus and p53 technology could not be combined.

E. p53-Adenovirus Constructs and Tumor Suppression

The present invention provides cancer gene therapy with a new and more effective tumor suppressor vector. This recombinant virus exploits the advantages of adenoviral vectors, such as high titer, broad target range, efficient transduction, and non-integration in target cells. In one embodiment of the invention, a replication-defective, helper-independent adenovirus is created that expresses wild type p53 (Ad5CMV-p53) under the control of the human cytomegalovirus promoter.

Control functions on expression vectors are often provided from viruses when expression is desired in mammalian cells. For example, commonly used promoters are derived from polyoma, adenovirus 2 and simian virus 40 (SV40). The early and late promoters of SV40 virus are particularly useful because both are obtained easily from the virus as a fragment which also contains the SV40 viral origin of replication. Smaller or larger SV40 fragments may also be used provided there is included the approximately 250 bp sequence extending from the HindIII site toward the BglI site located in the viral origin of replication. Further, it is also possible, and often desirable, to utilize promoter or control sequences normally associated with the included gene sequence, provided such control sequences are compatible with the host cell systems.

An origin of replication may be provided by construction of the vector to include an exogenous origin, such as may be derived from SV40 or other viral (e.g., polyoma, adeno, VSV, BPV) source, or may be provided by the host cell chromosomal replication mechanism. If the vector is integrated into the host cell chromosome, the latter is often sufficient.

Figure 2A:
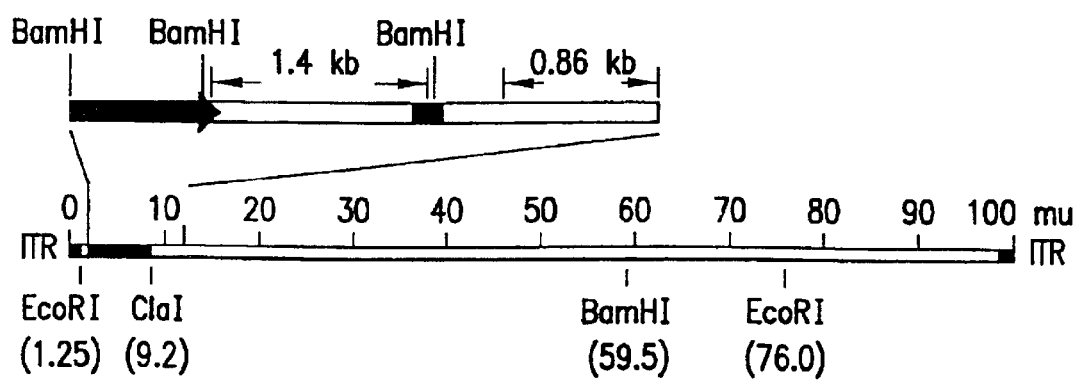
FIG. 2A. Map used for the structural analysis of Ad5CMV-p53 DNA. A map of Ad5CMV-p53 genomic DNA, with the locations of the p53 expression cassette, the PCR primers, and the restriction sites. The genome size is about 35.4 kb, divided into 100 maps units (1 m.u.=0.35 kb). The p53 expression cassette replaced the E1 region (1.3–9.2 m.u.) of the Ad5 genome. Primer 1 is located in the first intron downstream of the human CMV major IE gene promoter. Primer 2 is located in SV40 early polyadenylation signal. Both of the primers, 15–20 bp away from the p53 cDNA insert at both ends, define a 1.40 kb PCR product. Primers 3 and 4 are located at 11 m.u. and 13.4 m.u. of Ad5 genome, respectively, which define a 0.86 kb viral-genome specific PCR product.
Figure 2C:
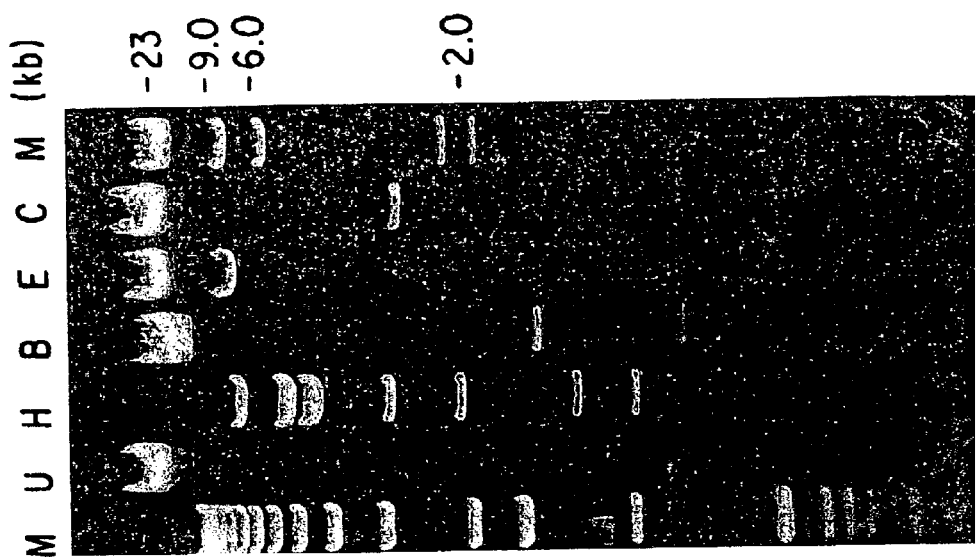
FIG. 2C. Restriction mapping of Ad5CMV-p53 DNA. CsCl-gradient purified Ad5CMV-p53 DNA samples were digested with no enzyme (U), Hind III (H), Bam HI (B), Eco RI (E), and Cla I (C), respectively, and analyzed on 1% agarose gel. The lanes labeled (M) are molecular weight markers.

The design and propagation of the preferred p53 adenovirus is diagramed in FIG. 1. In connection with this, an improved protocol has been developed for propagating and identifying recombinant adenovirus (discussed below). After identification, the p53 recombinant adenovirus was structurally confirmed by the PCR analysis, as indicated in FIG. 2. After isolation and confirmation of its structure, the p53 adenovirus was used to infect human lung cancer cell line H358, which has a homozygous p53 gene deletion. Western blots showed that the exogenous p53 protein was expressed at a high level (FIG. 4 and FIG. 5) and peaked at day 3 after infection (FIG. 6).

Figure 7A:
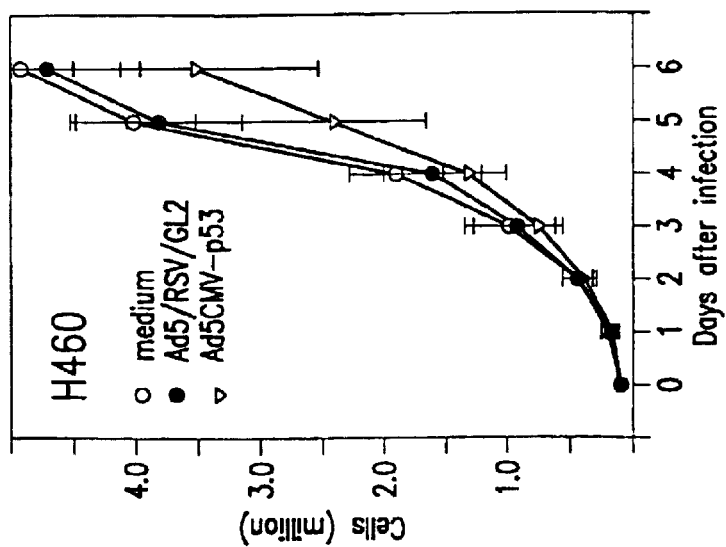
FIG. 7A. Growth curve of virally-infected human lung cancer cells of cell lines H358. Cells were inoculated at $10^5$ cells per dish (60 mm) and 6 dishes per cell line. After 24 hours, the cells were infected with Ad5CMV-p53 or Ad5/RSV/GL2 at 10 m.o.i. (Multiplicity of infection, i.e., PFU/cell). After infection cells were counted daily for 6 days. The growth curves represent data obtained from 4 separate studies.
Figure 7B:
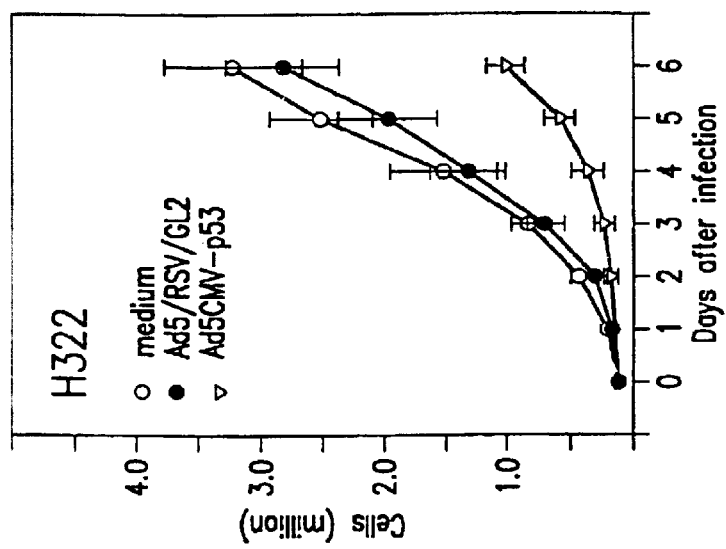
FIG. 7B. Growth curve of virally-infected human lung cancer cells of cell line H322. Cells were inoculated at $10^5$ cells per dish (60 mm) and 6 dishes per cell line. After 24 hours, the cells were infected with Ad5CMV-p53 or Ad5/RSV/GL2 at 10 m.o.i. (Multiplicity of infection, i.e., PFU/cell). After infection cells were counted daily for 6 days. The growth curves represent data obtained from 4 separate studies.
Figure 7C:
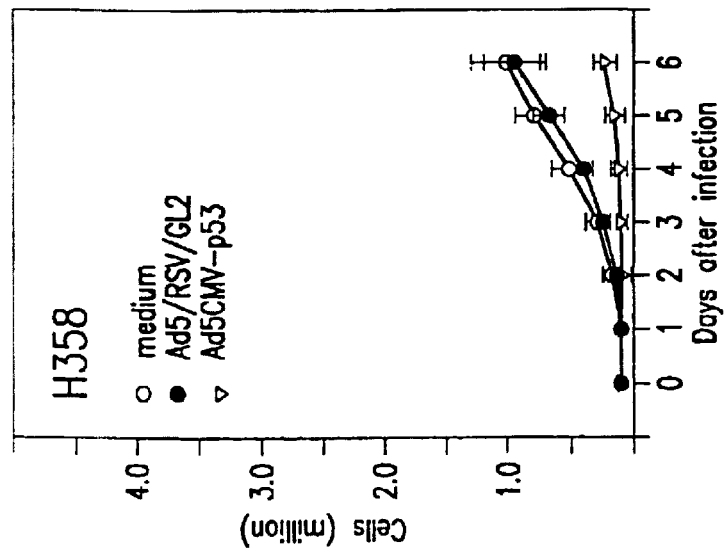
FIG. 7C. Growth curve of virally-infected human lung cancer cells of cell line H460. Cells were inoculated at $10^5$ cells per dish (60 mm) and 6 dishes per cell line. After 24 hours, the cells were infected with Ad5CMV-p53 or Ad5/RSV/GL2 at 10 m.o.i. (Multiplicity of infection, i.e. PFU/cell). After infection cells were counted daily for 6 days. The growth curves represent data obtained from 4 separate studies.

It was also shown in a p53 point mutation cell line H322 that the mutant p53 was down regulated by the expression of the exogenous p53. As an experimental control, a virion (Ad5/RSV/GL2) that had a structural similarity to that of Ad5CMV-p53 was used. This virion contained a luciferase cDNA driven by Rous sarcoma virus LTR promoter in the expression cassette of the virion. Neither p53 expression nor change in actin expression was detected in cells infected by the virion Ad5/RSV/GL2. Growth of the H358 cells infected with Ad5CMV-p53 was greatly inhibited in contrast to that of noninfected cells or the cells infected with the control virion (FIG. 7A). Growth of H322 cells was also greatly inhibited by the p53 virion (FIG. 7B), while that of human lung cancer H460 cells containing wild-type p53 was less affected (FIG. 7C).

Ad5CMV-p53 mediated a strong inhibitory effect on lung cancer cell growth in vitro. Growth inhibition was not as evident when the cells were infected with Ad5CMV-p53 at MOI lower than 1 PFU/cell, whereas, at MOI higher than 100 PFU/cell, cytotoxicity could be observed even with control virus Ad5/RSV/GL2. In our studies, the optimal dose for growth rate studies was 10–50 PFU/cell. Within this dose range, cell growth inhibition was attributable to the expressed p53 protein.

Tests in nude mice demonstrated that tumorigenicity of the Ad5CMV-p53-treated H358 cells was greatly inhibited. In a mouse model of orthotopic human lung cancer, the tumorigenic H226Br cells, with a point mutation in p53, were inoculated intratracheally 3 days prior to the virus treatment. Intratracheal instillation of Ad5CMV-p53 prevented tumor formation in this model system suggesting that the modified adenovirus is an efficient vector for mediating transfer and expression of tumor suppressor genes in human cancer cells and that the Ad5CMV-p53 virus may be further developed into a therapeutic agent for use in cancer gene therapy.

Ad5CMV-p53 mediated a high level of expression of the p53 gene in human lung cancer cells as demonstrated by Western blot analysis. Exogenous p53 protein was approximately 14 times more abundant than the endogenous wild-type p53 in H460 cells and about two to four times more abundant than the β-actin internal control in H358 cells. The high level of expression may be attributed to (1) highly efficient gene transfer, (2) strong CMV promoter driving the p53 cDNA, and (3) adenoviral E1 enhancer enhancing the p53 cDNA transcription. The duration of p53 expression after infection was more than 15 days in H358 cells. However, there was a rapid decrease in expression after postinfection day 5. PCR analysis of the DNA samples from the infected H358 cells showed a decrease of the viral DNA level with the decreased protein level, indicating the loss of viral DNA during the continuous growth of cancer cells in Vitro.

The decrease in p53 expression may also have resulted from cellular attenuation of the CMV promoter that controls p53 expression, since the phenomenon of host cell-mediated CMV promoter shut off has been reported previously (Dai, et al., 1992). Adenoviral vectors are nonintegrative gene transfer vectors and therefore the duration of gene expression depends upon a number of factors, including the host cells, the genes transferred, and the relevant promoter. Crystal and co-workers showed low level expression of the cystic fibrosis transmembrane conductance regulator gene in cotton rat epithelial cells was detectable 6 weeks after infection (Rosenfeld, et al., 1992). Perricaudet's laboratory demonstrated minimal expression of minidystrophin gene in mdx mouse muscle lasted for more than 3 months after infection. The short-term high level expression of the wild-type p53 protein observed in the present study may have the beneficial effect of reducing possible side effects on normal cells following in vivo treatment with Ad5CMV-p53.

The studies disclosed herein indicate that the p53 recombinant adenovirus possesses properties of tumor suppression, which appear to operate by restoring p53 protein function in tumor cells. These results provide support for the use of the Ad5CMV-p53 virion as a therapeutic agent for cancer treatment.

F. DNA Damaging Agents

A wide variety of DNA damaging agents may be used with the present invention, such as, agents that directly crosslink DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis, and chromosomal segregation. Examples of these compounds include adriamycin, also known as doxorubicin, etoposide, verapamil, podophyllotoxin, and the like. Widely used in clinical setting for the treatment of neoplasms these compounds are administered through bolus injections intravenously at doses ranging from 25–75 mg/m2 at 21 day intervals for adriamycin, to 35–50 mg/m2 for etoposide intravenously or double the intravenous dose orally.

Agents that disrupt the synthesis and fidelity of nucleic acid precursors, and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that these all of these factors effect a broad range of damage on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan in directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

G. p53 and Cisplatin Treatment

Figure 13A:
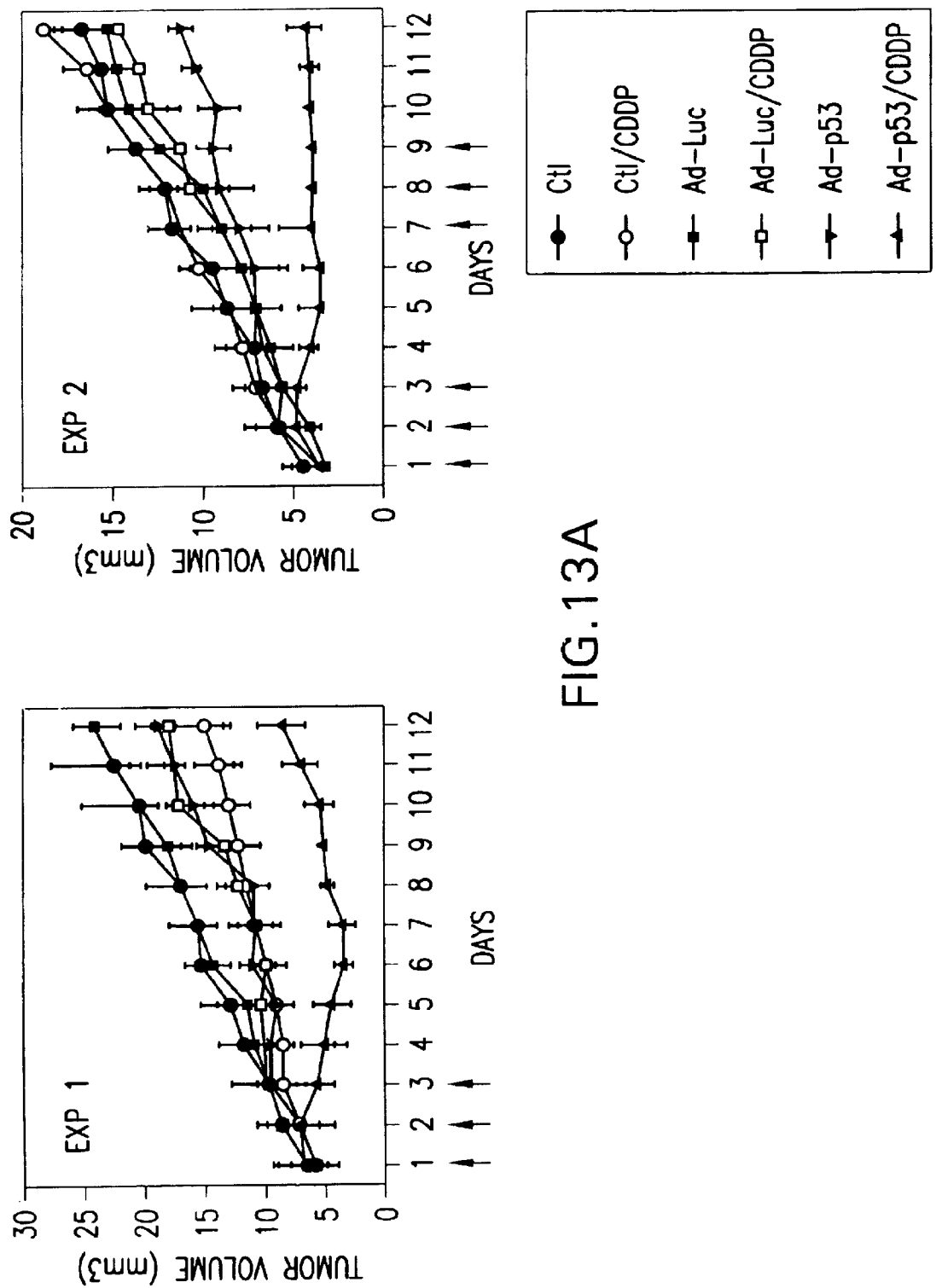
FIG. 13A. Induction of apoptosis by CDDP after in vivo infection with Ad-p53 as measured by tumor volume changes. H358 cells ($5 \times 10^6$) in 0.1 ml Hank's balanced salt solution were injected subcutaneously into the right flank of BALB/c female nu/nu mice. Thirty days later, 200 μl of medium alone or medium containing Ad-Luc ($10^8$ PFU/ml) or Ad-p53 ($10^8$ PFU/ml) was injected into tumors with a diameter of 5 to 6 mm. Intratumoral injection (100 μl) and peritumoral injection in two opposite sites (50 μl each) were performed. CDDP (3 mg/kg) or control physiological saline was given intraperitoneally. The tumors were measured with calipers in two perpendicular diameters without the knowledge of the treatment groups, and a tumor volume was calculated by assuming a spherical shape with the average tumor diameter calculated as the square root of the product of cross-sectional diameters. Five mice were used for each treatment group and the mean +/− SE is shown. The data was analyzed using the Student's t-test. The arrow shows the day of treatment. Two independent determinations are shown. p<0.05 from day 5 in test 1; p<0.05 from day 7 in test 2. (B–E)
Figure 13C:
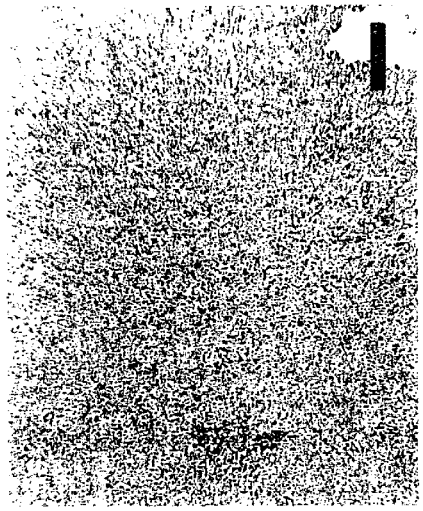
FIGS. 13B, 13C, 13D, and 13E. Histologic study using the TdT-mediated biotin-dUTP labeling technique. Tumors were harvested 5 days after the beginning of treatment and immediately embedded into O. C. T. compound. Frozen tissues were cut in a cryostat at 5-μm thicknesses. The sections were treated with 1 μg/ml proteinase K and stained as described in the legend to FIG. 12. Pictured are H358 tumors treated with (B) CDDP alone, (C) Ad-p53 alone, or (D, E) Ad-p53 in the combination with CDDP. Bars=0.5 mm. All animal care was in accordance with the UT M.D. Anderson Institutional Animal Care and Use Committee.
Figure 13E:
Figure 13B:
Figure 13D:

In an effort to determine the efficacy of a combination of gene replacement therapy and chemotherapy in human cancer, the inventors examined whether sequential administration of Ad-p53 and CDDP could induce apoptosis in vivo. Following 3 days of direct intratumoral injection of Ad-p53 or intraperitoneal administration of CDDP, H358 tumors implanted subcutaneously in nu/nu mice showed a modest slowing of growth. However, if Ad-p53 and CDDP were simultaneously administered, tumors partially regressed and the tumor size remained statistically significantly smaller than those in any of the other treatment groups. The growth inhibitory effect was even more pronounced after two treatment cycles (FIG. 13A). Histologic examination revealed a massive destruction of tumor cells in the area where Ad-p53 was injected in mice treated with CDDP. In situ staining demonstrated many apoptotic cells around acellular spaces (FIGS. 13B–E). In contrast, tumors treated with CDDP alone or Ad-p53 alone showed neither acellularity nor apoptotic areas.

The present invention describes a novel strategy for human gene therapy combined with conventional chemotherapy using a DNA crosslinking agent. Tumor cell resistance to chemotherapeutic drugs represents a major problem in clinical oncology. NSCLC accounts for at least 80% of the cases of lung cancer; patients with NSCLC are, however, generally unresponsive to chemotherapy (Doyle, 1993). One goal of current cancer research is to find ways to improve the efficacy of gene replacement therapy for cancer by investigating interaction between the gene product and chemotherapeutic drugs. The herpes simplex-thymidine kinase (HS-tK) gene, when delivered to brain tumors by a retroviral vector system, successfully induced susceptibility to the antiviral agent ganciclovir (Culver, et al., 1992). The HS-tK gene product is an exogenous viral enzyme, whereas the wt-p53 protein is expressed in normal tissues, suggesting that the modulation of chemoresistance by alterations in wt-p53 expression might be an alternative approach using a pathway mediated by an endogenous genetic program.

An adenovirus system has potential advantages for gene delivery in vivo, such as ease of producing high titer virus, high infection efficiency, and infectivity for many types of cells. The stability and duration of expression of the introduced gene are still controversial, however. For chemo-gene therapy, the levels of expression and the high infectivity may be are more significant than the duration of expression, because drugs can kill infected cells within several days. The increase in p53 levels in cells that are sensitive to chemotherapeutic drugs can occur within 6 hours after DNA-damaging stimuli (Fritsche, et al., 1993, Zhan, et al., 1993), although increased p53 DNA binding activity can be reversed over the course of 4 hours if the stimulus is removed (Tishler, et al., 1993). In the present model, the expression of the wt-p53 gene is driven independently by the cytomegalovirus promoter contained in an Ad-p53 vector. Therefore, a high level of p53 expression can be maintained even after cessation of drug exposure. The expression of wt-p53 protein by Ad-p53 peaks at postinfection day 3 (14-fold greater than endogenous wild type) and decreases to a low level by day 9 (Zhang, et al., 1993). This suggests that a transiently high level of wt-p53 expression is sufficient to initiate the cytotoxic program in the cancer cell.

H. Patients and Treatment Protocols

The inventors propose that the regional delivery of adenoviral-p53 gene constructs to lung cancer cells in patients with p53-linked cancers, such as unresectable obstructing endobronchial cancers, will be a very efficient method for delivering a therapeutically effective gene to counteract the clinical disease. The deliver of the p53 gene is to occur in combination with agents or factors that lead to DNA damage. This combined approach is a significant improvement on current cancer therapies, for example the loss of sensitivity to cisplatin alone, which rely on attempts to kill or remove the last cancer cell by effecting DNA damage. As tumor cell dormancy is an established phenomenon, this makes effective killing highly unlikely.

It is anticipated that the uptake of the adenovirus constructs by NSCLC cells will decrease the rate of proliferation of these cells, however, the present examples demonstrate that the combined use of a DNA damaging agent or factor with the p63 adenovirus leads to a profound diminution of cell growth and tumor size, not shown with either factor alone. The compositions and methods disclosed herein, strongly portend an increase in the length of time the affected lung would remain expanded, prevent regrowth of the tumor and division of tumor cells, and prolong the patient's survival.

Patients with unresectable endobronchial tumor recurrence that is partially or completely obstructing the airway and that have failed or are unable to receive external beam radiotherapy will be considered for this combined protocol. Existing therapies for this condition offer only short-term palliation. Most patients have recurred despite external beam radiotherapy. It may be possible to insert a brachytherapy catheter and administer additional radiotherapy, intravenous administration of DNA damaging agents. Patients receiving current treatments have a median survival of 6 months. Patients failing brachytherapy would also be eligible to receive gene therapy. Tumor can be removed from the airway with the laser or biopsy forceps. This can be done in conjunction with injection of the adenoviral constructs thus decreasing the volume that must be injected. The administration of the viral constructs would not preclude the patient from receiving other palliative therapy if the tumor progresses.

I. Other Gene Transfer Techniques

Successful gene therapy generally requires the integration of a gene able to correct the genetic disorder into the host genome, where it would co-exist and replicate with the host DNA and be expressed at a level to compensate for the defective gene. Ideally, the disease would be cured by one or a few treatments, with no serious side effects. There have been several approaches to gene therapy proposed to date, which may be used with the present invention.

A first approach is to transfect DNA containing the gene of interest into cells, e.g., by permeabilizing the cell membrane either chemically or physically. This approach is generally limited to cells that can be temporarily removed from the body and can tolerate the cytotoxicity of the treatment (i.e. lymphocytes). Liposomes or protein conjugates formed with certain lipids and amphophilic peptides can be used for in vivo transfection (Stewart et al., 1992; Torchilin et al., 1992; Zhu et al., 1993), however present efficiency of gene integration is very low. It is estimated that the gene of interest integrates into the genome of only one cell in 1,000 to 100,000. In the absence of integration, expression of the transfected gene is limited to several days in proliferating cells or several weeks in non proliferating cells due to the degradation of the un-integrated DNAs.

A second approach capitalizes on the natural ability of viruses to enter cells, bringing their own genetic material with them. Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

A third method uses other viruses, such as adenovirus, herpes simplex virues (HSV), cytomegalovirus (CMV), and adeno-associated virus (AAV), which are engineered to serve as vectors for gene transfer. Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Construction of P53 Expression Vector

This example describes the construction of a p53 expression vector. This vector is constructed as indicated and is used to replace the E1 region (1.3–9.2 m.u.) of the Adenovirus strain Ad5 genome and employed to construct the Adenovirus virion described in Example 2.

The p53 expression cassette shown in FIG. 1, which contains human cytomegalovirus (CMV) promoter (Boshart, et al., 1985), p53 cDNA, and SV40 early polyadenylation signal, was inserted between the Xba I and Cla I sites of pXCJL1 (provided by Dr. Frank L. Graham, McMaster University, Canada).

The genome size is about 35.4 kb, divided into 100 map units (1 m.u.=0.35 kb). The p53 expression cassette replaced the E1 region (1.3–9.2 m.u.) of the Ad5 genome.

Primer 1 has the sequence 5'-GGCCCACCCCCT-TGGCTTC-3' (SEQ ID NO:1) and is located in the first intron downstream of the human CMV major IE gene promoter (Boshart, et al., 1985). Primer 2 has the sequence 5'-TTGTAACCATTATAAGCTGC-3' (SEQ ID NO:2) and is located in SV40 early polyadenylation signal. Both of the primers, 15–20 bp away from the p53 cDNA insert at both ends, define a 1.40 kb PCR product. Primer 3 has the sequence 5'-TCGTTTCTCAGCAGCTGTTG-3' (SEQ ID NO:3) and primer 4 has the sequence 5'-CATCTGAACTCAAAGCGTGG-3' (SEQ ID NO:4) and are located at 11 m.u. and 13.4 m.u. of the Ad5 genome, respectively, which define a 0.86 kb viral-genome specific PCR product.

EXAMPLE 2

Generation and Propagation of Recombinant D53 Adenovirus

This example describes one method suitable for generating helper-independent recombinant adenoviruses expressing p53. The molecular strategy employed to produce recombinant adenovirus is based upon the fact that, due to the packaging limit of adenovirus, pJM17 cannot form virus on its own. Therefore, homologous recombination between the p53 expression vector plasmid and pJM17 within a transfected cell results in a viable virus that can be packaged only in cells which express the necessary adenoviral proteins.

The method of this example utilizes 293 cells as host cells to propagate viruses that contain substitutions of heterologous DNA expression cassettes at the E1 or E3 regions. This process requires cotransfection of DNA into 293 cells. The transfection largely determines efficiency of viral propagation. The method used for transfection of DNA into 293 cells prior to the present invention was usually calcium-phosphate/DNA coprecipitation (Graham and van der Eb, 1973). However, this method together with the plaque assay is relatively difficult and typically results in low efficiency of viral propagation. As illustrated in this example, transfection and subsequent identification of infected cells were significantly improved by using liposome-mediated transfection, when identifying the transfected cells by cytopathic effect (CPE).

The 293 cell line was maintained in Dulbecco's modified, minimal essential medium supplemented with 10% heat-inactivated horse serum. The p53 expression vector and the plasmid pJM17 (McGrory, et al., 1988) for homologous recombination were cotransfected into 293 cells by DOTAP-mediated transfection according to the manufacture's protocol (Boehringer Mannheim Biochemicals, 1992). This is schematically shown in FIG. 1.

The 293 cells (passage 35, 60% confluency) were inoculated 24 hours prior to the transfection in either 60 mm dishes or 24-well plates. The cells in each well were transfected with: 30 µl DOTAP, 2 µg of p53 expression vector, and 3 µg of plasmid pJM17. After transfection cells were fed with the MEM medium every 2–3 days until the onset of CPE.

EXAMPLE 3

Confirming the Identity of Recombinant Adenovirus

This example illustrates a new polymerase chain reaction (PCR) assay for confirming the identity of recombinant virions following cotransfection of the appropriate cell line.

Aliquots of cell culture supernatants (50 to 370 µl) were collected from the test plates, treated with proteinase K (50 µg/ml with 0.5%. SDS and 20 mM EDTA) at 56° C. for 1 hour, extracted with phenol-chloroform, and the nucleic acids were ethanol precipitated. The DNA pellets were resuspended in 20 µl dH$_2$O and used as template for PCR amplification. The relative locations of the PCR primers and their sequences are depicted in FIG. 1 and are SEQ ID NOS:1, 2, 3 and 4, respectively. The cDNA insert-specific primers define a 1.4 kb PCR product and the viral genome-specific primers define a 0.86 kb PCR product. The PCR reactions were carried out in a 50 µl volume containing 4 mM MgCl$_2$, 50 mM KCl, 0.1% Triton X-100™, 200 µM each of dNTPs, 10 mM Tris-Cl (pH 9.0), 2 µM of each primer, and 1.0 unit of Taq polymerase (Promega). The reactions were carried out at 94° C., 0.5 min, 56° C., 0.5 min, and 72° C., 1 min for 30 cycles.

In order to simplify the procedure of identification of newly propagated recombinant virus, a direct PCR assay on DNA samples from cell culture supernatant was developed. Aliquots (50 or 370 µl) of the cell medium supernatant with CPE were treated with proteinase K and phenol/chloroform extraction. After ethanol precipitation, the DNA samples were analyzed using PCR employing two pairs of primers to amplify insert-specific and viral-genome-specific sequences. The PCR primer targets and their sequences are depicted in FIG. 1. Primers 1, 2, 3 and 4 are represented by SEQ ID NOS:1, 2, 3 and 4, respectively.

Figure 2B:
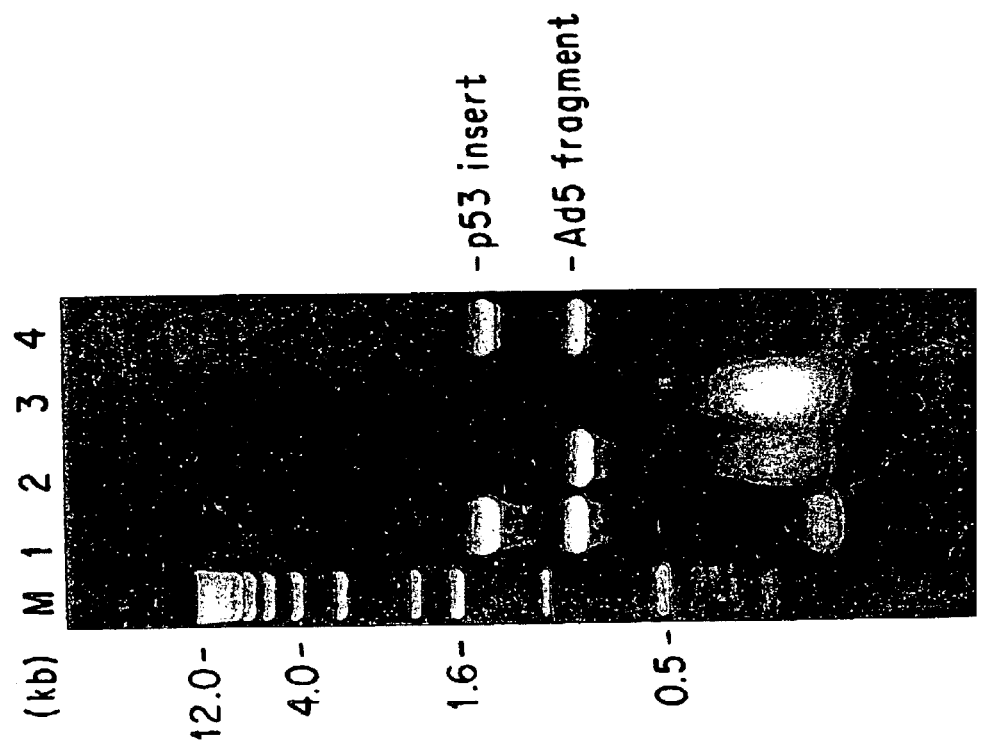
FIG. 2B. Agarose gel analysis of PCR products. Two pairs of primers that define 1.4-kb (p53) and 0.86-kb (Ad5) DNA fragments were used in each reaction. DNA templates used in each reaction were pEC53 plasmid (lane 1), Ad5/RSV/GL2 DNA (lane 2), no DNA (lane 3), and Ad5CMV-p53 DNA (lane 4). The lane labeled (M) corresponds to molecular weight markers.
Figure 3B:
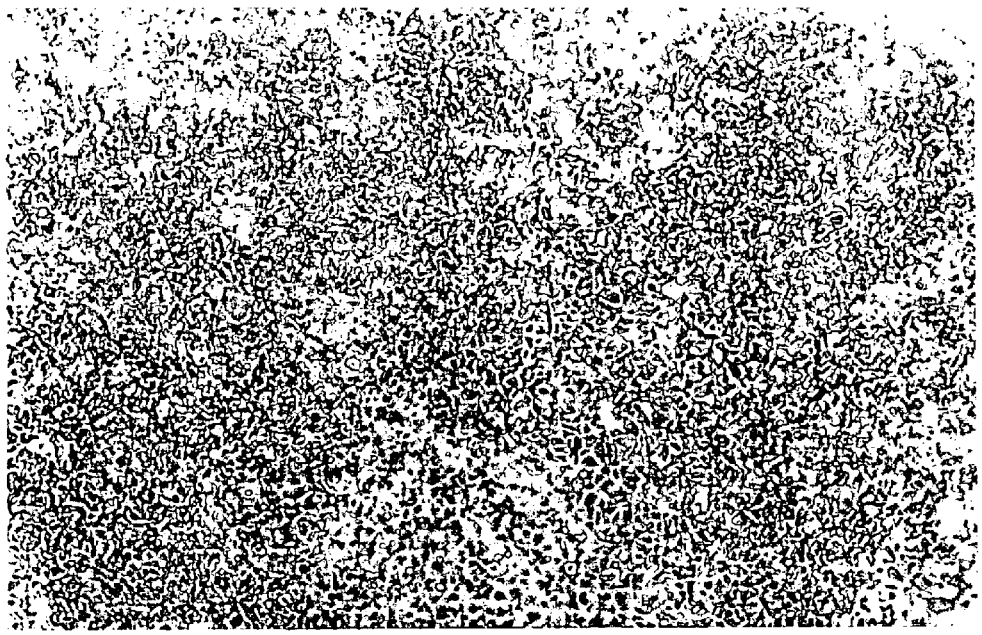
FIG. 3A, 3B, 3C and 3D. Observation of cytopathic effects on 293 by recombinant adenovirus.
Figure 3A:
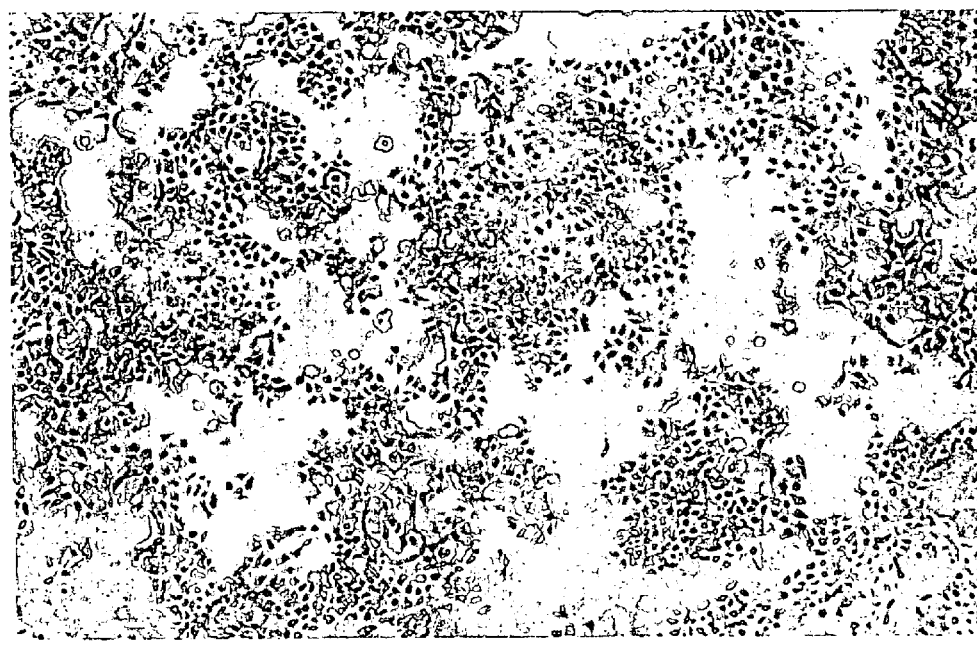
Figure 3D:
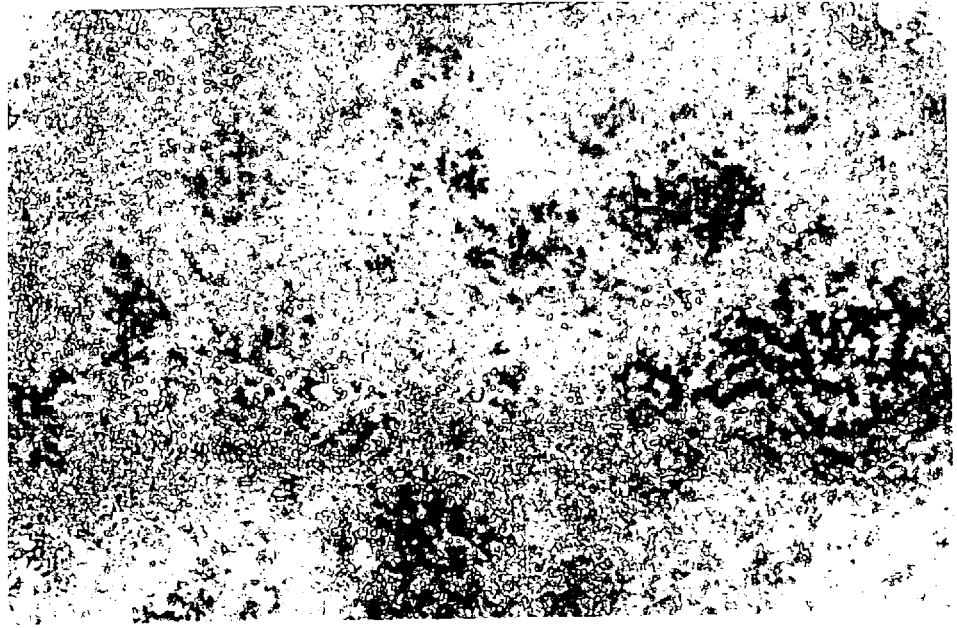
Figure 3C:
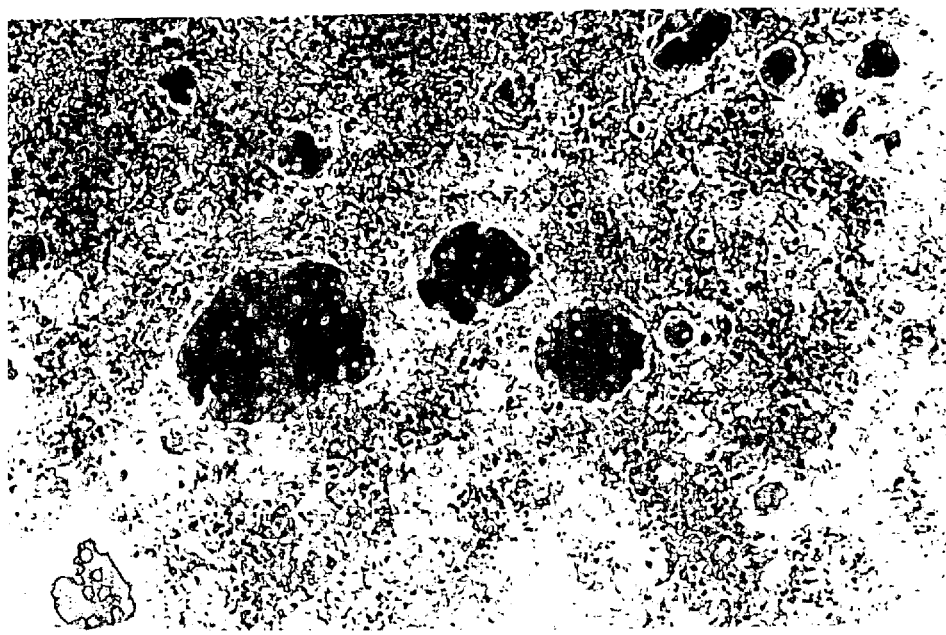
Figure 4B:
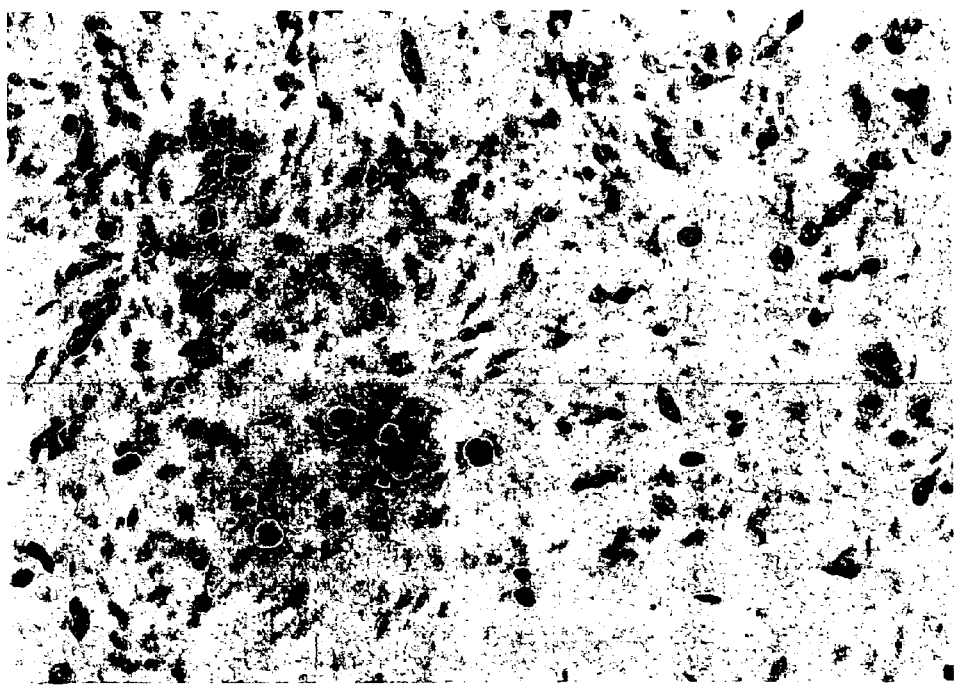
FIGS. 4A, 4B, 4C, and 4D. Immunohistology of cells infected with recombinant adenoviruses.
Figure 4A:
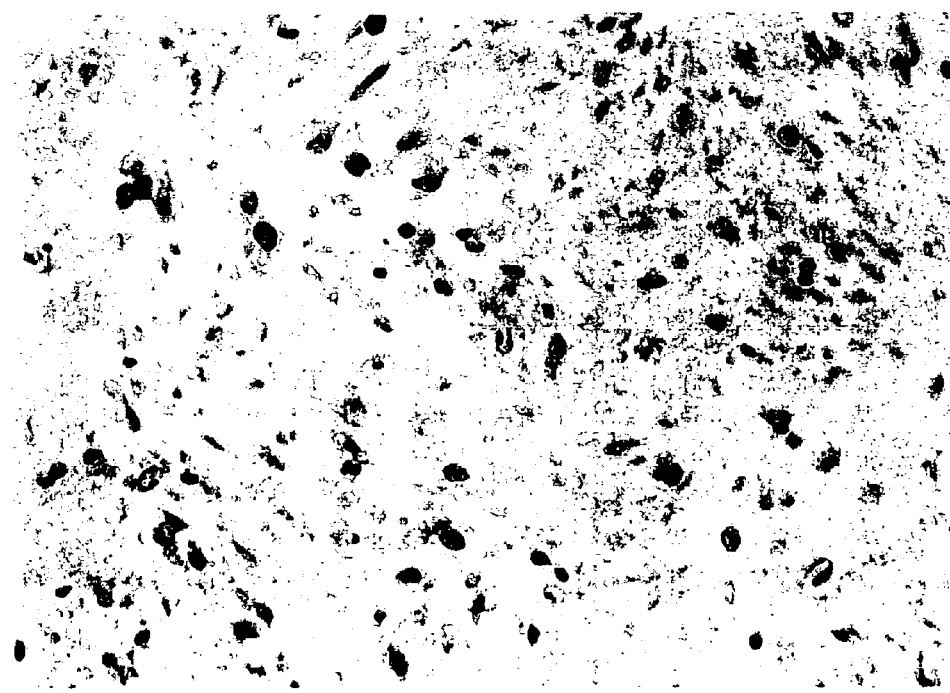
Figure 4D:
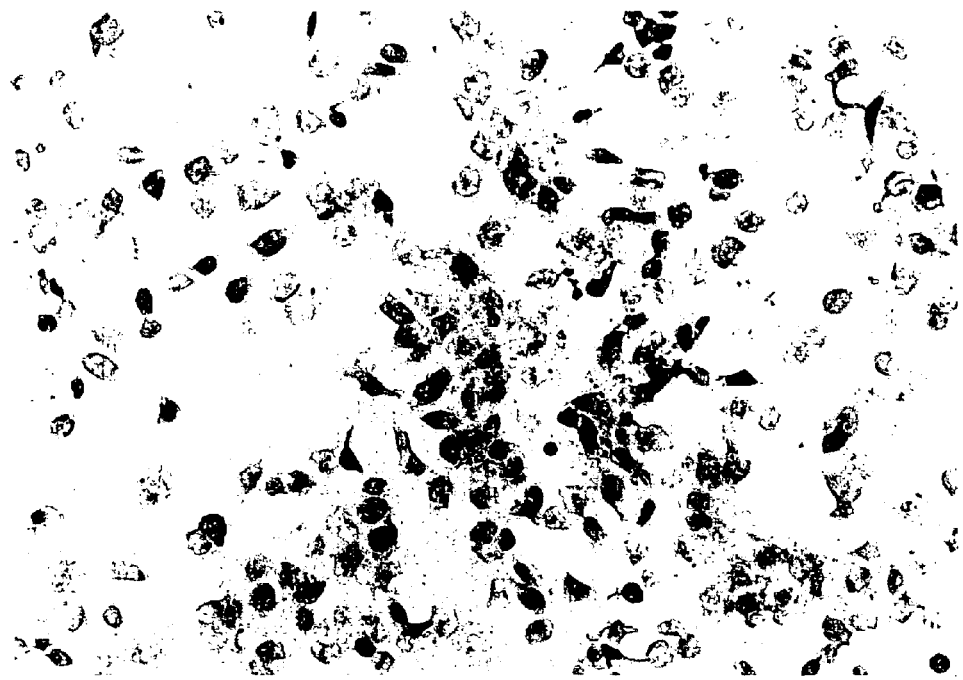
Figure 4C:
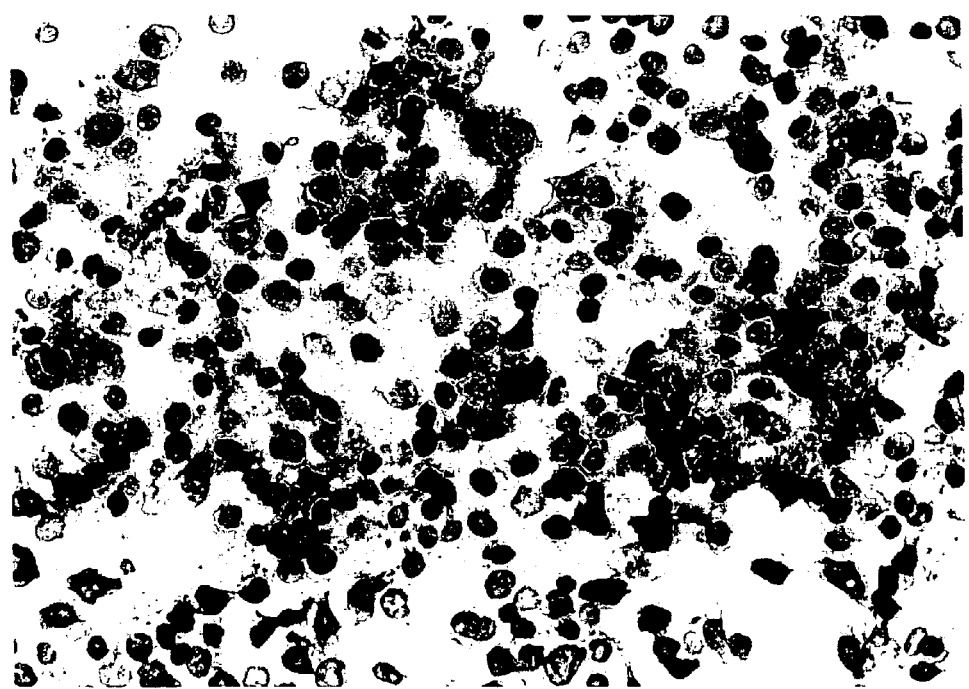

As a result, a 1.4 kb cDNA insert and a 0.86 kb viral genome fragment were amplified from the expression vector (positive control) and the DNA samples of the positive cell culture (FIG. 2B, lane 1 and 4, respectively). Only the 0.86 kb fragment was amplified from the DNA sample of Ad5/RSV/GL2 virus (negative control, lane 2). No amplified bands appeared from PCR at reactions that used either untreated positive cell culture medium supernatant (lane 3).

These results indicated that adenoviruses released into cell culture medium are detectable by PCR, using as little as 50 µL of the cell culture medium supernatant for preparing DNA templates. These results will allow development of a quantitative method for using this technique to determine adenovirus titers, traditionally done by plaque assays.

The wild-type sequence of the p53 cDNA in the Ad5CMV-p53 virus was confirmed by dideoxy DNA sequencing on the CsCl-gradient-purified viral DNA. The control virus Ad5/RSV/GL2, generated in a similar manner, has a structure similar to that of Ad5CMV-p53 except a Rous sarcoma viral promoter and luciferase cDNA were used in its expression cassette. The recombinant adenovirus that carries a E. coli β-galactosidase gene (LacZ), Ad5CMV-LacZ, also has a structure similar to that of Ad5CMV-p53, and is obtainable as disclosed in Zhang et al. and from Dr. Frank L. Graham (please see Graham, et al., 1991).

Viral stock, titer, and infection. Individual clones of the Ad5CMV-p53, Ad5/RSV/GL2, and Ad5CMV-LacZ viruses were obtained by plaque-purification according to the method of Graham and Prevec (1991). Single viral clones were propagated in 293 cells. The culture medium of the 293 cells showing the completed cytopathic effect was collected and centrifuged at 1000×g for 10 min. The pooled supernatants were aliquoted and stored at −20° C. as viral stocks. The viral titers were determined by plaque assays (Graham and Prevec, 1991). Infections of the cell lines were carried out by addition of the viral solutions (0.5 ml per 60-mm dish) to cell monolayers and incubation at room temperature for 30 min with brief agitation every 5 min. This was followed by the addition of culture medium and the return of the infected cells to the 37° C. incubator.

The gene transfer efficiency of the recombinant adenoviruses was also evaluated using Ad5CMV-LacZ in a variety of cell lines such as H226Br, H322, H460, HeLa, Hep G2, LM2, and Vero. By X-gal staining, all of the cell lines were stained 97–100% blue after infection with Ad5CMV-LacZ at an MOI of 30 PFU/cell.

EXAMPLE 4

Ad5CMV-p53-Directed p53 Gene Expression in Human Lung Cancer Cells

This example describes the use of recombinant p53 adenovirus to infect human lung cancer cells with a homozygous p53 gene deletion. The results show that growth of these cells and expression of mutant p53 was suppressed, indicating the potential of the Ad5CMV-p53 virion as a useful agent for control of metastatic cells.

Immunohistochemistry was performed on infected cell monolayers that were fixed with 3.8% formalin and treated with 3% H$_2$O$_2$ in methanol or 5 min. Immunohistochemical analysis was performed using Vectastain ELITE™ kit (Vector, Burlingame, Calif.). The primary antibody used was anti-p53 antibody PAb 1801 (Oncogene Science, Manhasset, N.Y.); MOPC-21 (Organon Teknika Corp., West Chester, Pa.) was used as a negative control. The second antibody was an avidin-labeled anti-mouse IgG (Vector). The biotinylated horseradish peroxidase ABC complex reagent was used to detect the antigen-antibody complex. Finally the cells were counterstained with Harris hematoxylin (Sigma) and mounted with Cytoseal™ 60 (Stephens Scientific, Riverdale, N.J.).

Immunohistochemical analysis of the infected cell lines was performed to examine the in situ expression of p53 expression driven by the CMV promoter of the Ad5CMV-53 virus. In the H358 cell line, which has a homozygous deletion of p53, the p53 gene was transferred with 97–100% efficiency, as detected by immunohistochemical analysis, when the cells were infected with Ad5CMV-p53 at a multiplicity of infection of 30–50 plaque-forming units (PFU)/ cell (FIG. 4).

The high transfer efficiency of recombinant adenovirus was confirmed by Ad5CMV-LacZ, a virus which carries the LacZ gene transcribed by the human CMV IE promoter. At an MOI of 30–50 PFU/cell, all of the cells examined, including HeLa, Hep G2, LM2, and the human NSCLC cancer cell lines were 97–100% positive for b-galactosidase activity by X-gal staining. These results indicate that adenoviral vectors are an efficient vehicle for gene transfer into human cancer cells.

Western blotting analysis was performed on total cell lysates prepared by lysing monolayer cells in dishes with SDS-PAGE sample buffer (0.5 ml per 60-mm dish) after rinsing the cells with phosphate-buffered saline (PBS). For SDS-PAGE analysis lanes were loaded with cell lysates equivalent to $5 \times 10^4$ cells (10–15 ml). The proteins in the gel were transferred to Hybond™-ECL membrane (Amersham, Arlington Heights, Ill.). The membranes were blocked with 0.5% dry milk in PBS and probed with the primary antibodies: mouse anti-human p53 monoclonal antibody PAb 1801 and mouse anti-human β-actin monoclonal antibody (Amersham), washed and probed with the secondary antibody: horseradish peroxidase-conjugated rabbit anti-mouse IgG (Pierce chemical Co., Rockford, Ill.). The membranes were developed according to the Amersham's enhanced chemiluminescence protocol. Relative quantities of the exogenous p53 expressed were determined by densitometer (Molecular Dynamics Inc., Sunnyvale, Calif.).

Figure 5A:
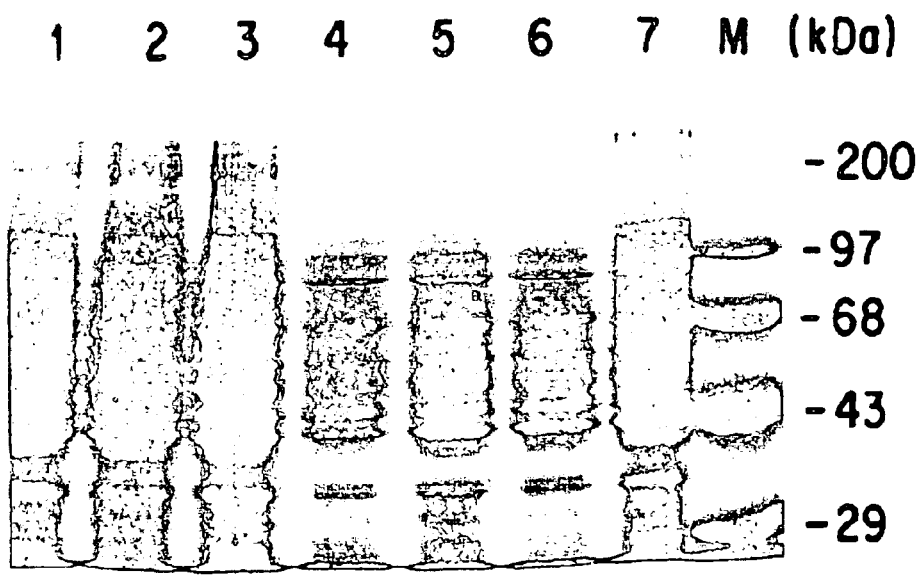
FIG. 5A. Coomassie-blue stained SDS-PAGE gel comparing the relative level of expression of exogenous p53 in H358 cells. H358 cell samples that were infected with Ad5CMV-p53 or Ad5/RSV/GL2 at 30 PFU/cell were prepared 24 and 72 h after infection. Coomassie blue staining of an SDS-PAGE analysis, showing relative quantities of protein samples loaded. Lanes 1 and 4 contain the samples of the Ad5/RSV/GL2-infected cells. Lanes 2 and 3 contain the samples of the cells infected with two individual stocks of Ad5CMV-p53 at 24 h after infection. Lanes s and 6 are the Ad5CMV-p53-infected cell samples collected at 72 h after infection. Lane 7 is mock-infected H358 sample 72 h after infection. Lane M, prestained molecular weight markers in kDa (GIBCO-BRL).
Figure 5B:
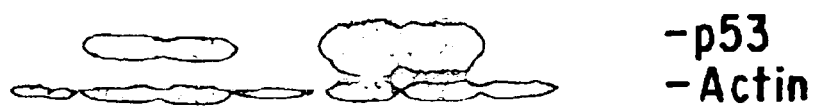
FIG. 5B. Western blot analysis of the identical lane setting gel as that of the SDS-PAGE in FIG. 5A. The relative levels of expression of p53 were analyzed by Western blotting-using anti-p53. Primary antibodies used were monoclonal antibodies against p53 protein (PAb 1801, Oncogene Science Inc.) and β-actin (Amersham Inc.). The HRP-conjugated second antibody and ECL developer were from Amershem Inc.viral-infected H358 cells by Western Blotting. Western blot of FIG. 5B have an equivalent setup and order to those in FIG. 5A.
Figure 6:
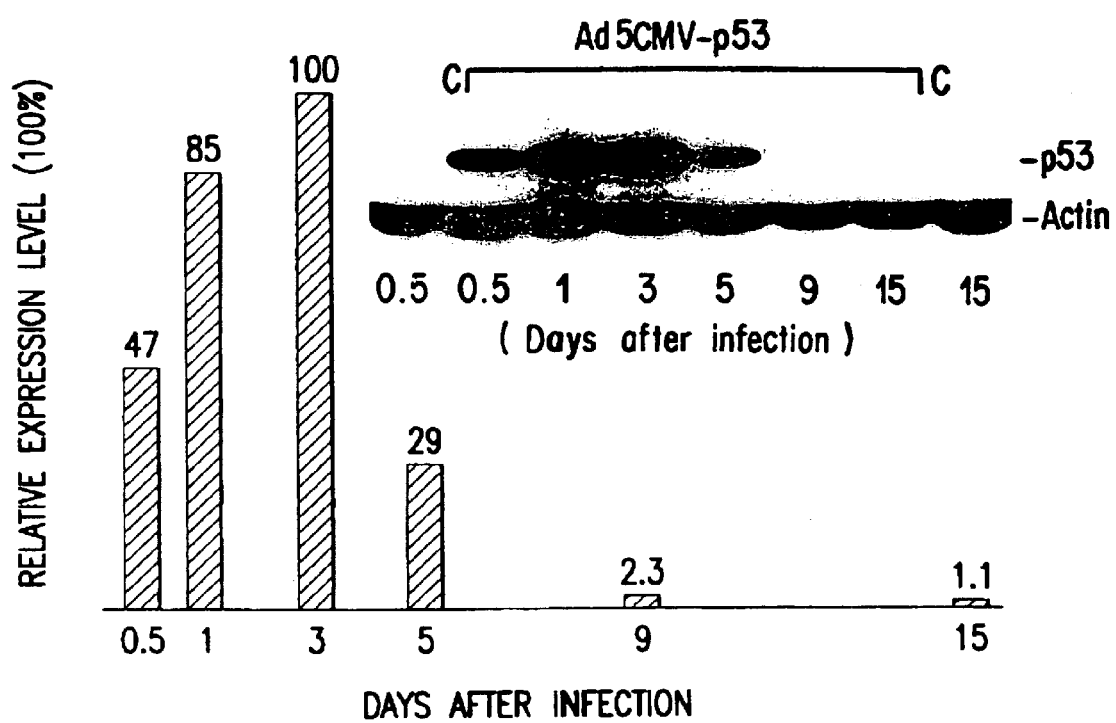
FIG. 6. Time course of the p53 expression, determined by Western blotting. Multiple dishes of H358 cells were infected with Ad5CMV-p53 at 10 PFU/cell. Cell lysates were prepared at indicated time points after infection. Western blotting was probed with anti-p53 and anti-actin antibodies simultaneously. The lanes designated 'C' represent negative controls. The histogram represents the relative quantities of p53 as determined by a densitometer.

Western blots showed the exogenous p53 protein was expressed at a high level (FIG. 5A lanes 2,3 and 5,6). The protein peaked at day 3 after infection (FIG. 6, insert, 0.5 days to 3 days). As a control, a virion with a structure similar to the recombinant Ad5CMV-p53 of Example 1 was constructed. This virion contains a luciferase cDNA driven by Rous Sarcoma Virus LTR promoter in the expression cassette of the virion. Neither p53 expression nor change in actin expression was detected in the cells infected by the virion Ad5/RSV/GL2.

The recombinant p53 adenovirus was used to infect three human lungs NSCLC cell lines: cell line H358, which has a homozygous deletion of the p53 gene, cell line H322, which has a point mutation of the p53 gene at codon 248 (G to T), and cell line H460, which has a wild-type p53 gene. The growth rate of human NSCLC cells was determined following the inoculation of H322 and H460 ($1 \times 10^5$) or H358 ($2 \times 10^5$) in 60-mm culture dishes 24 h before viral infection. The cells were infected with the viruses at a multiplicity of infection (MOI) of 10 PFU/cell. Culture medium was used for the mock infection control. Triplet cultures of each cell line with different treatments were counted daily for days 1–6 after infection.

Growth of the H358 cells infected with Ad5CMV-p53 was greatly inhibited in contrast to that of noninfected cells or the cells infected with the control virion (FIG. 7A). Growth of H322 cells was also greatly inhibited by the p53 virion (FIG. 7B), while that of human lung cancer H460 cells containing wild type p53 was affected to a lesser degree (FIG. 7C). Growth of the Ad5CMV-p53 virus-infected H358 cells was inhibited 79%, whereas that of noninfected cells or the cells infected with the control virus were not inhibited. Growth of cell line H322, which has a point mutation in p53, was inhibited 72% by Ad5CMV-p53, while that of cell line H460 containing wild-type p53 was less affected (28% inhibition).

The results indicate that the p53 recombinant adenovirus possesses properties of tumor suppression, working through restoration of the p53 protein function in tumor cells.

EXAMPLE 5

Ad5CMV-p53 in the Treatment of p53 Deficient Cells

The present example concerns the use of recombinant p53 adenovirus to restore growth suppression of tumor cells in vitro and thus to treat the malignant or metastatic growth of cells. It describes some of the ways in which the present invention is envisioned to be of use in the treatment of cancer via adenovirus-mediated gene therapy.

H358 cells were infected with Ad5CMV-p53 and Ad5/RSV/GL2 at a MOI of 10 PFU/cell. An equal amount of cells were treated with medium as a mock infection. Twenty-four hours after infection, the treated cells were harvested and rinsed twice with PBS. For each treatment, three million ($3 \times 10^6$) cells in a volume of 0.1 ml were injected s.c. to each nude mouse (Harlan Co., Houston, Tex.). Five mice were used for each treatment. Mice were irradiated (300 cGy, $^{60}$Co) before injection and examined weekly after injection. Tumor formation was evaluated at the end of a 6-week period and tumor volume was calculated by assuming a spherical shape with the average tumor diameter calculated as the square root of the product of cross-sectional diameters.

To determine the inhibitory effect on tumorigenicity mediated by Ad5CMV-p53 nude mice were injected s.c. with H358 cells (a human NSCLC-type cell) to induce neoplastic growth. Each mouse received one injection of cells that had been infected with Ad5CMV-p53 or Ad5/RSV/GL2 at 10 PFU/cell for 24 h. H358 cells treated with medium alone were used as mock-infected controls. Tumors, first palpable at postinjection day 14, were induced only by the mock- or control virus-infected cells as demonstrated in Table I:

TABLE I

Effect of Ad5CMV-p53 on tumorigenicity of H358 in nude mice[a]

| Treatment | No. of Tumors/ No. of Mice (%) | Mean Volume (mm³ ± SD) |
| --- | --- | --- |
| Medium | 4/5 (80) | 37 ± 12 |
| Ad5/RSV/GL2 | 3/4 (75) | 30 ± 14 |
| Ad5CMV-p53 | 0/4 (0) | — |

[a]The treated H358 cells were injected s.c. at $2 \times 10^6$ cells/mouse. Tumor sizes were determined at the end of a 6-week period.

As shown in Table 1 mice that received Ad5CMV-p53-treated cells did not develop tumors. The tumors at the end of a 6-week period were 4–10 mm in diameter. This study was initiated with five mice per group; one mouse each in the Ad5CMV-p53 or Ad5/RSV/GL2 group failed to complete the study. The early deaths were presumably due to nosocomial infection.

EXAMPLE 6

Ad5CMV-p53 in the Treatment of Lung Cancer

The present example concerns the use of recombinant p53 adenovirus to restore growth suppression of tumor cells in vivo and thus to treat cancers in animals. It describes some of the ways in which the present invention is envisioned to be of use in the treatment of cancer via adenovirus-mediated gene therapy.

The efficacy of Ad5CMV-p53 in inhibiting tumorigenicity was further evaluated in the mouse model of orthotopic human lung cancer. Since H358 and H322 cells did not produce tumors in this model, cell line H226Br was used. This cell line has a squamous lung cancer origin and metastasized from lung to brain. H226br has a point mutation (ATC to GTC) at exon 7, codon 254, of the p53 gene and is tumorigenic in mice.

The procedure for tests in the mouse model of orthotopic human lung cancer has been previously described (Georges, et al., 1993). Briefly, nude mice treated with radiation (300 cGy, $^{60}$Co) were inoculated with H226Br cells by intratracheal instillation. Each mouse received $2\times10^6$ cells in a volume of 0.1 ml PBS. Three days after inoculation, 10 mice per group were treated with 0.1 ml of viruses or vehicle (PBS) by intratracheal instillation once a day for two days. The virus dosage used was $5\times10^7$ Ad5CMV-p53 or Ad5/RSV/GL2 per mouse. The mice were euthanized at the end of a 6-week period. Tumor formation was evaluated by dissecting the lung and mediastinum tissues and measuring the tumor size. The tumors were confirmed by histologic analysis of the sections of the tumor mass.

Figure 8:
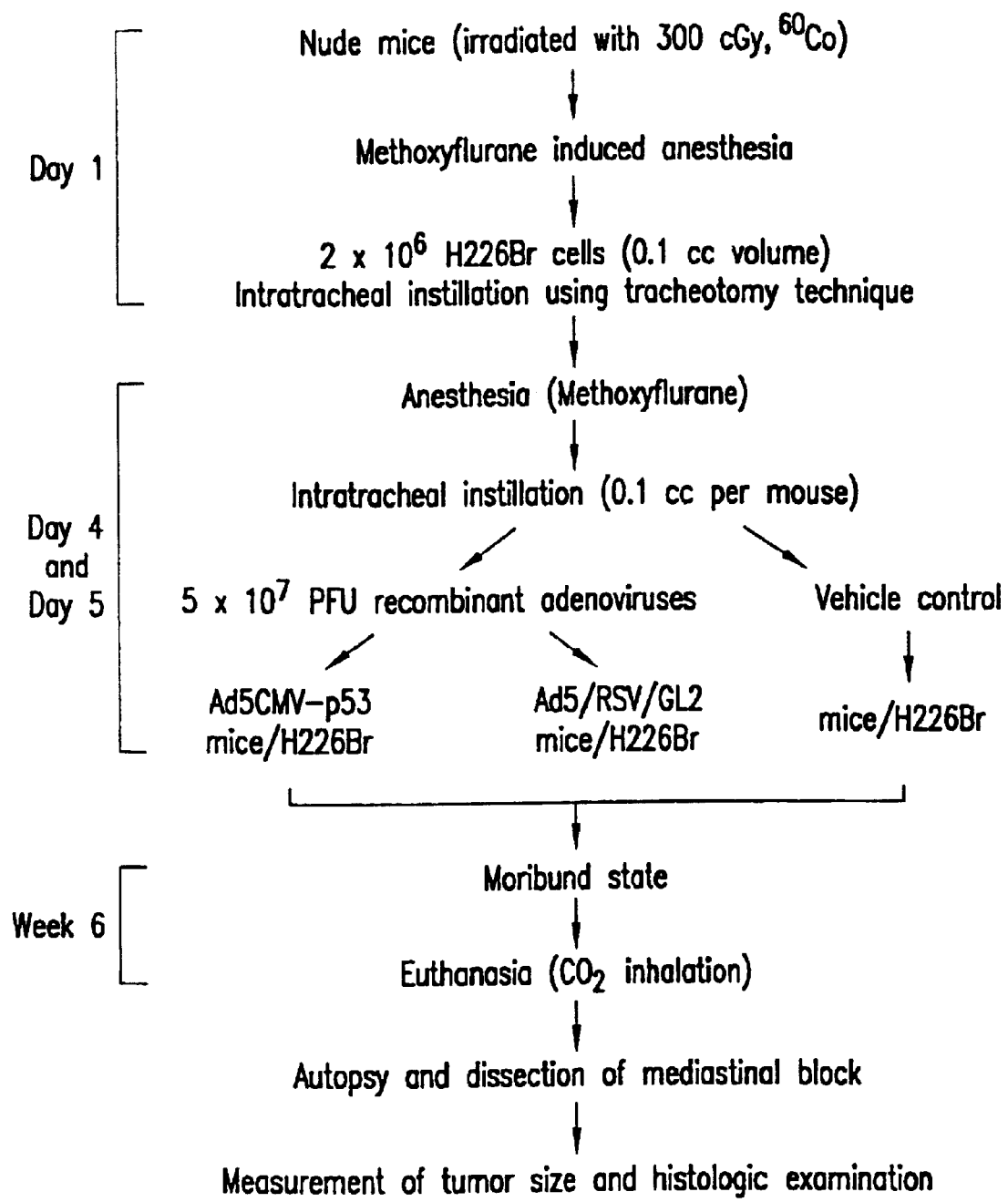
FIG. 8. Flow chart of tests of Ad5CMV-p53 in orthotopic lung cancer model. The dosages and schedule of treatment of nude mice inoculated with H226Br cells and viruses are summarized in the flow chart.
Figure 9A:
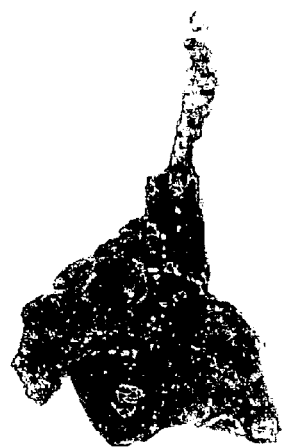
FIGS. 9A, 9B, 9C, and 9D. Samples of the lung and mediastinum dissection from treated and control mice.
Figure 9B:
Figure 9C:
Figure 9D:
Figure 9D:

The irradiated nude mice were inoculated with $2\times10^6$ H226Br cells/mouse by intratracheal instillation. Three days after inoculation, each of the mice (8–10 mice per group) were treated with 0.1 ml of either Ad5CMV-p53 or Ad5/RSV/GL2 or vehicle (PBS) by intratracheal instillation once a day for two days. The virus dosage used was $5\times10^7$ PFU/mouse. Tumor formation was evaluated at the end of a 6-week period by dissecting the lung and mediastinum tissues and measuring the tumor size. A flow chart of the procedure is depicted in FIG. 7, with representative samples of dissection demonstrated in FIG. 8. The detected tumors were confirmed by histologic analysis. The data of tumor measurements are summarized in Table II:

TABLE II

Effect of Ad5CMV-p53 on tumorigenicity of H226Br in mouse model of orthotopic human lung cancer[a]

| Treatment | No. mice with Tumors/ Total Mice (%) | Mean Volume (mm$^3$ ± SD) |
|---|---|---|
| Vehicle | 7/10 (70) | 30 ± 8.4 |
| Ad5/RSV/GL2 | 8/10 (80) | 25 ± 6.9 |
| Ad5CMV-p53 | 2/8 (25) | 8 ± 3.3[b] |

[a]Mice were inoculated with $2 \times 10^6$ H226Br cells/mouse intratracheally. On the 3rd day postinoculation, the mice were given either vehicle or viruses ($5 \times 10^7$ each in 0.1 ml) intratracheally once a day for 2 days. Tumor formation was evaluated at the end of a 6-week period.
[b]$p < 0.05$ by two-way analysis of variance when compared to the groups receiving vehicle (PBS) or virus control.

Only 25% of the Ad5CMV-p53-treated mice formed tumors, whereas in the vehicle or Ad5/RSV/GL2 control group, 70–80% of the treated mice formed tumors. The average tumor size of the Ad5CMV-p53 group was significantly smaller than those of the control groups. These results indicate that Ad5CMV-p53 can prevent H226Br from forming tumors in the mouse model of orthotopic human lung cancer.

EXAMPLE 7

Synergism Between p53 and DNA Damage

The biochemical features of programmed cell death (apoptosis) show a characteristic pattern of DNA fragmentation resulting from cleavage of nuclear DNA. Recent studies have demonstrated that induction of apoptosis by chemotherapeutic drugs or ionizing radiation may be related to the status of the p53 gene and that DNA-damaging stimuli are able to elevate intracellular p53 protein levels in cells that are in the process of apoptosis (Lowe, et al., 1993, Clarke, et al., 1993, Fritsche, et al., 1993, Harper, et al., 1993, El-Deiry, et al., 1993). Inhibition of the cell cycle at the $G_1$ phase by increased levels of the wild-type p53 (wt-p53) protein allows more time for DNA repair; if optimal repair is impossible, p53 may trigger programmed cell death. Thus, p53 may contribute to the induction of apoptotic tumor cell death by chemotherapeutic agents.

Inactivation of the p53 gene by missense mutation or deletion is the most common genetic alteration in human cancers (Levine, et al., 1991, Hollstein, et al., 1991). The loss of p53 function has been reported to enhance cellular resistance to a variety of chemotherapeutic agents (Lowe, et al., 1993). The inventors studies showed that human non-small cell lung cancer (NSCLC) H358 cells, in which both alleles of p53 are deleted, were resistant to chemotherapeutic drugs, whereas cell line WTH226b, which has endogenous wt-p53, readily showed apoptotic cell death 16 hours after treatment with cisplatin (CDDP) and etoposide (VP-16) (T. Fujiwara, E. A. Grimm, T. Mukhcpadhyay, J. A. Roth, unpublished data). Therefore, the inventors sought to determine whether the introduction of the wt-p53 gene into H358 cells by an adenoviral vector could increase the cell's sensitivity to the DNA crosslinking agent CDDP in vitro and in vivo.

Materials and Methods

H358 cells were kindly provided by A. Gazdar and J. Minna (Takahashi, et al., 1989)

Adenovirus Vectors

The construction and identification of a recombinant adenovirus vector that contains the cDNA that encodes human wt-p53 (Ad-p53) or luciferase (Ad-Luc) were previously reported (Zhang, et al., 1993). Briefly, the p53 expression cassette that contains human cytomegalovirus promoter, wt-p53 cDNA, and SV40 early polyadenylation signal, was inserted between the XbaI and ClaI sites of pXCJL.1. The p53 shuttle vector and the recombinant plasmid pJM17 were cotransfected into 293 cells (Ad5-transformed human embryonic kidney cell line) by a liposome-mediated technique. The culture supernatant of 293 cells showing the complete cytopathic effect was collected and used for subsequent infections. The control Ad-Luc virus was generated in a similar manner. Ad-p53 and Ad-Luc viruses were propagated in 293 cells. The presence of replication competent virus was excluded by HeLa cell assays. The viral titers were determined by plaque assays (Graham, et al., 1991).

Detection of Nucleosomal DNA Fragmentation

DNA was isolated from parental, Ad-Luc-infected, and Ad-p53-infected cells that did or did not receive CDDP treatment, by incubating cells at 55° C. for 6 hours in lysis buffer (50 mM Tris-HCl, pH 8.0, 100 mM EDTA, 100 mM NaCl, 1% SDS, and 50 µg/ml proteinase K). DNA was extracted twice with equal volumes of phenol and once with chloroform-isoamylalcohol (24:1) and then precipitated in ethanol. Samples were subjected to electrophoresis on a 1.5% agarose gel, and visualized by ethidium bromide staining.

TdT-mediated dUTP nick end labeling was performed according to a procedure previously reported (Gavrieli, et al., 1992). Monolayer cells were treated with 0.01% NP-40. The slides were immersed in TdT buffer (30 mM Tris-HCl, pH 7.2; 140 mM sodium cacodylate; 1 mM cobalt chloride) and incubated with biotinylated dUTP (Boehringer Mannheim, Indianapolis, Ind.) and TdT at 37° C. for 45 min. The slides were covered with 2% bovine serum albumin for 10 min and incubated with avidin-biotin complex (Vectastain Elite Kit; vector Laboratories, Burlingame, Calif.) for 30 min. The calorimetric detection was performed by using diamino-benzidine.

Results

H358 cells were transduced vitro with the human wt-p53 cDNA by exposure to Ad-p53. Western blot analysis showed a high level of wt-p53 protein expression as early as 24 hours after infection with Ad-p53, but no wt-p53 was detected in parental (uninfected) cells or control cells infected with Ad-Luc (data not shown). Concurrent immunohistochemical evaluation demonstrated detectable wt-p53 protein in more than 80% of infected cells, suggesting that the transfer and expression of p53 by AD-p53 was highly efficient (data not shown).

Figure 10A:
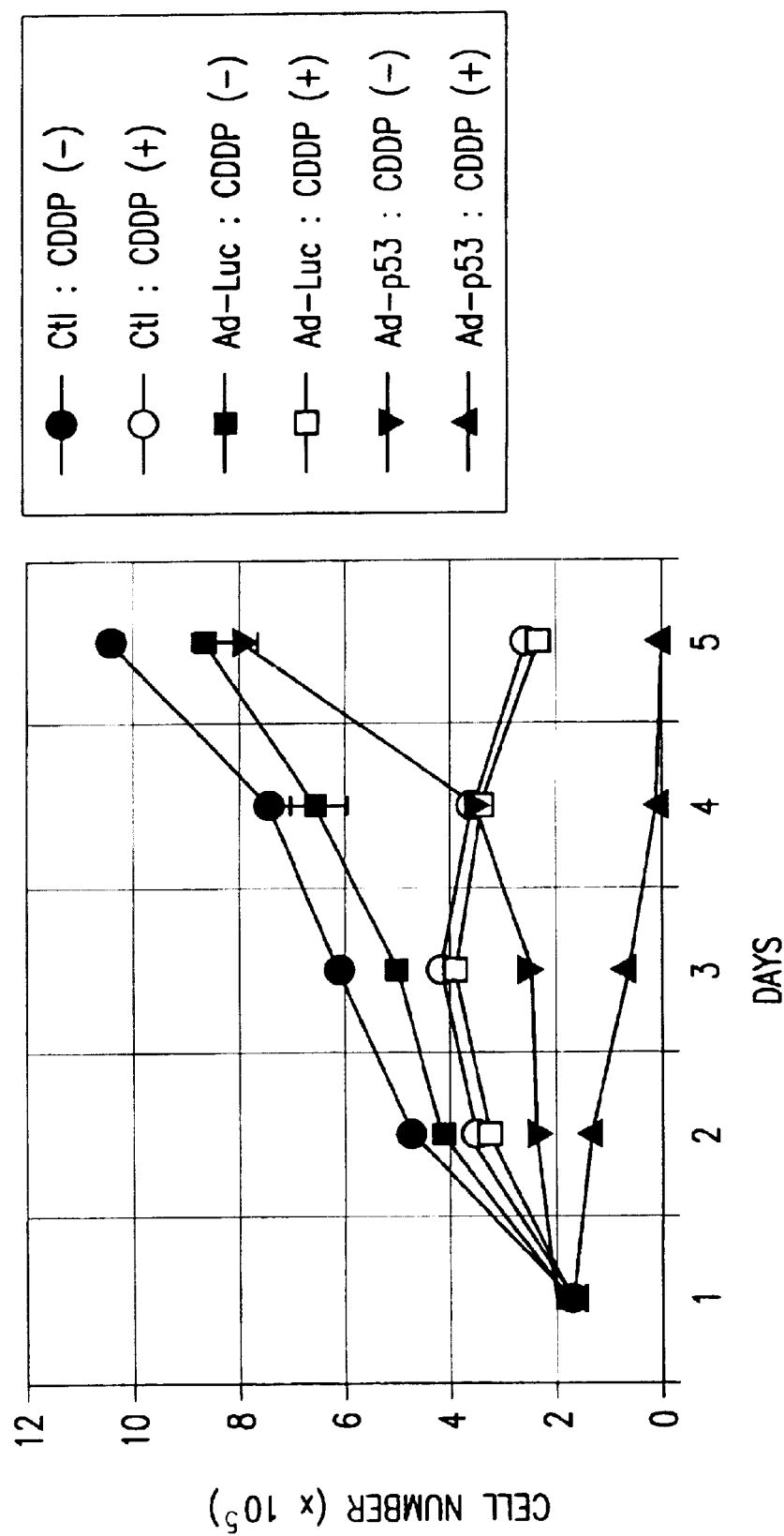
FIG. 10A. The effects of continuous exposure to CDDP on the growth rates of parental, Ad-Luc-infected, and Ad-p53-infected H358 cells. H358 cells ($1.5 \times 10^5$ cells/well) were seeded in duplicate on a 24-well plate. After 24 hours, 100 μl of medium, Ad-Luc viral stock ($10^8$ PFU/ml), or Ad-p53 viral stock ($10^8$ PFU/ml) was added. Following an additional 24-hour incubation, the medium that contained virus was replaced with fresh medium that contained 10 μg/ml of CDDP.
Figure 10C:
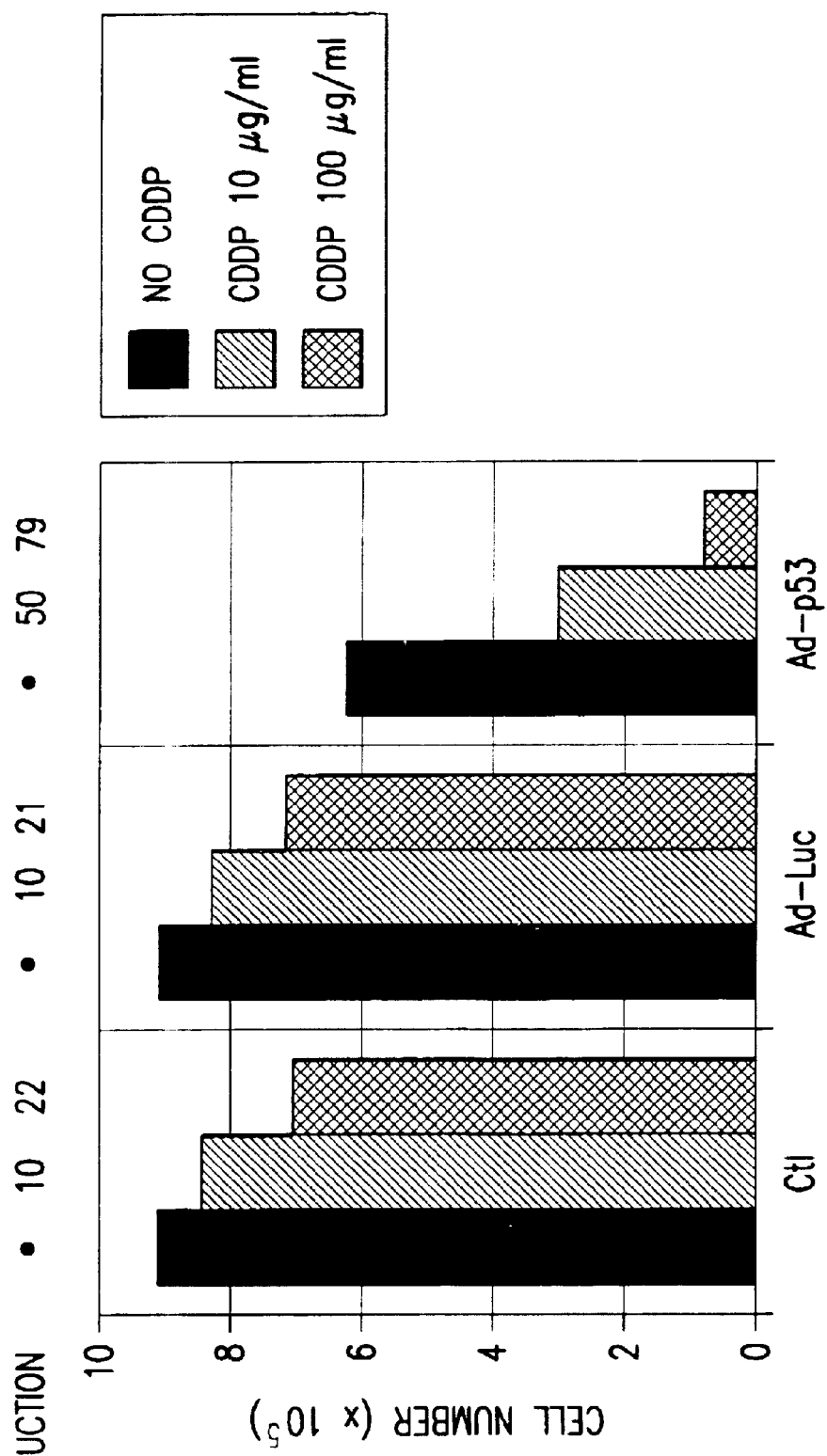
FIG. 10C. The effects of different concentrations of CDDP on the viability of Ad-p53-infected H358 cells. After 24-hour exposure to the Ad-Luc or Ad-p53 virus, cells were treated with 0, 10, or 100 μg/ml of CDDP for 24 hours and then assessed for viability.

Continuous exposure of Ad-p53-infected H358 cells to CDDP reduced their viability rapidly, whereas significant cell death for parental and Ad-Luc-infected cells occurred only after 72 hours of exposure to CDDP (FIG. 10A). Loss of viability was greatly enhanced in cells transduced with Ad-p53. Moreover, the reduction of viability could be observed even when cells were maintained in drug-free-medium after 24 hours of exposure, suggesting that lethal damage could be induced within 24 hours (FIG. 10B). The sensitivity of wt-p53-transduced H358 cells to CDDP was dose dependent (FIG. 10C).

Figure 11A:
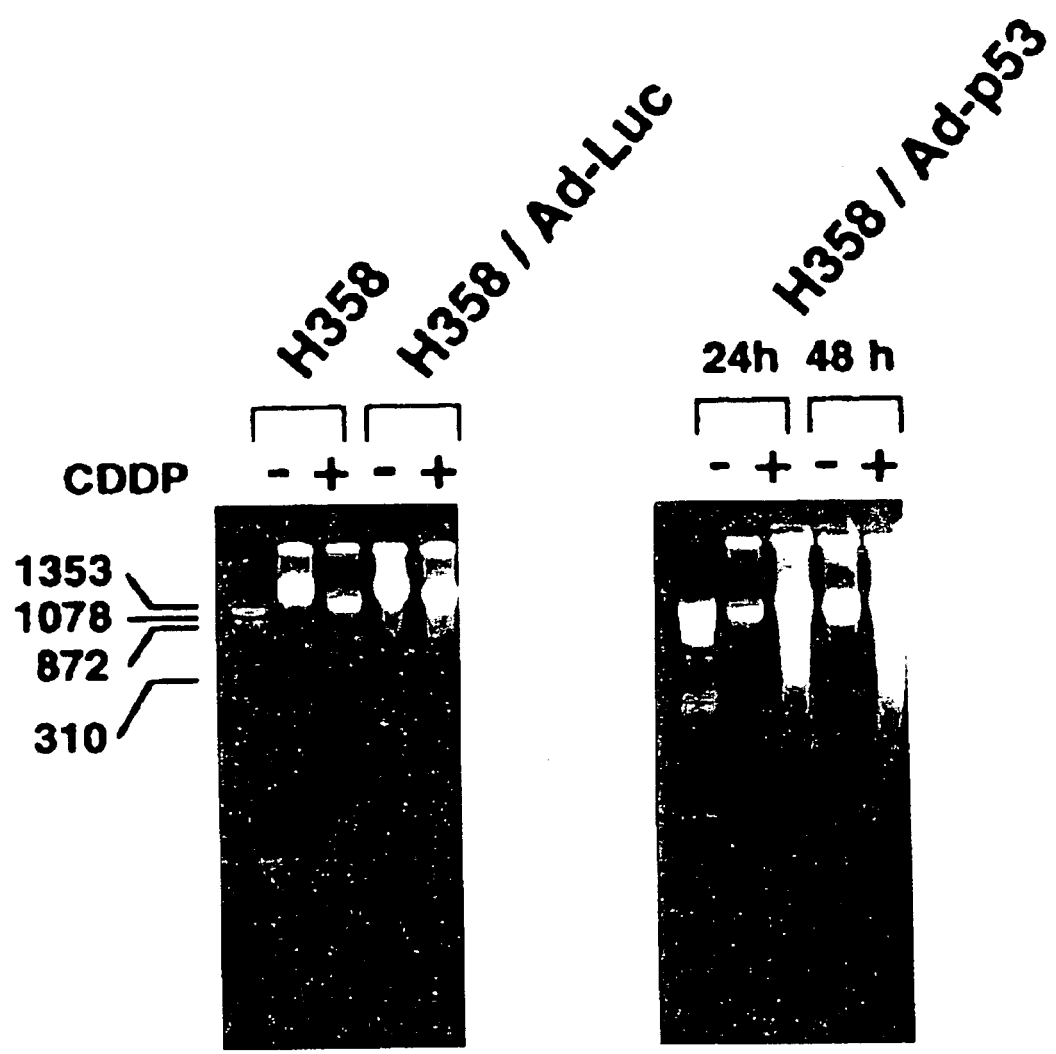
FIG. 11A. Nucleosomal DNA fragmentation in Ad-p53-infected H358 cells exposed to CDDP. Cells were infected and treated with CDDP for 24 hours as described in the legend to FIG. 10.
Figure 11B:
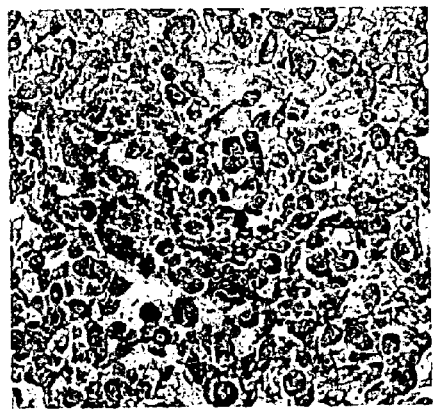
FIGS. 11B, 11C, 11D, 11E and 11G. H358 cells that were grown on chamber slides, infected with Ad-p53 for 24 hours, treated with CDDP for an additional 24 hours, and fixed for in situ labeling of DNA fragmentation. Pictured are parental. H358 cells (B) without or (C) with CDDP; Ad-Luc-infected cells (D) without or (E) with CDDP; and Ad-p53-infected cells (F) without or (G) with CDDP. The arrowhead shows an example of darkly stained nuclear fragments. Bar=100 μm.
Figure 11C:
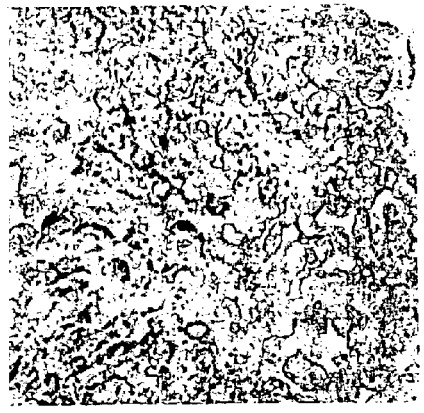
Figure 11D:
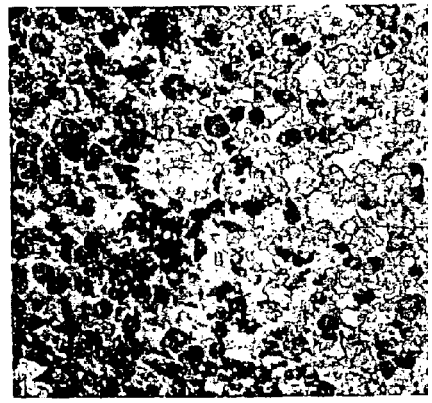
Figure 11E:
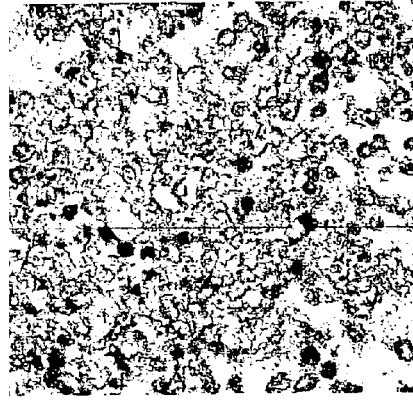
Figure 11F:
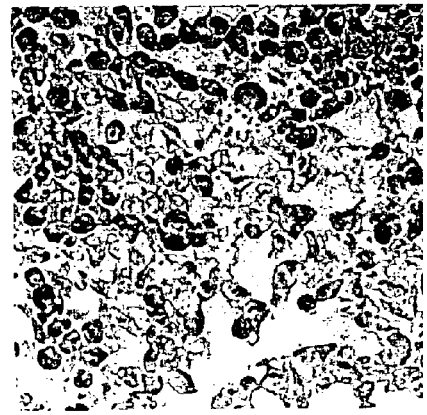
Figure 11G:
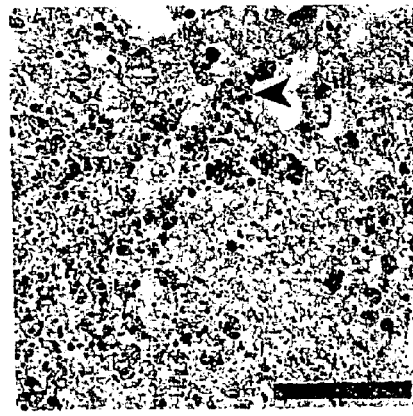

An internucleosomal DNA ladder indicative of DNA fragmentation was evident in cells expressing wt-p53 after 24 hours of exposure to CDDP; parental and Ad-Luc-infected cells, however, did not show DNA fragmentation (FIG. 11A). Terminal deoxynucleotidyl transferase (TdT)-mediated 2'-deoxyuridine-5'-triphosphate (dUTP)-biotin nick end labeling, which detects DNA fragmentation characteristic of apoptosis in situ, showed many apoptotic cells in Ad-p53-infected cells treated with CDDP for 24 hours as shown in FIG. 11G which demonstrates darkly staining nuclei and nuclear fragments not present in FIGS. 11B–F.

Introduction of wt-p53 is known to induce apoptosis in some types of tumor cell lines with deleted or mutated p53 (Yonish-Rouach, et al., 1991, Shaw, et al., 1992, Ramqvist, et al., 1993). However, overexpression of wt-p53 alone could not promote DNA fragmentation in the p53-negative H358 cell line (FIG. 11), although their growth was suppressed by Ad-p53 (FIG. 10). This is compatible with the inventors previous observations showing that stable H358 clones could be obtained after retrovirus-mediated wt-p53 transfer and that the clones grew more slowly than parental cells (Cai, et al., 1993).

Figure 12A:
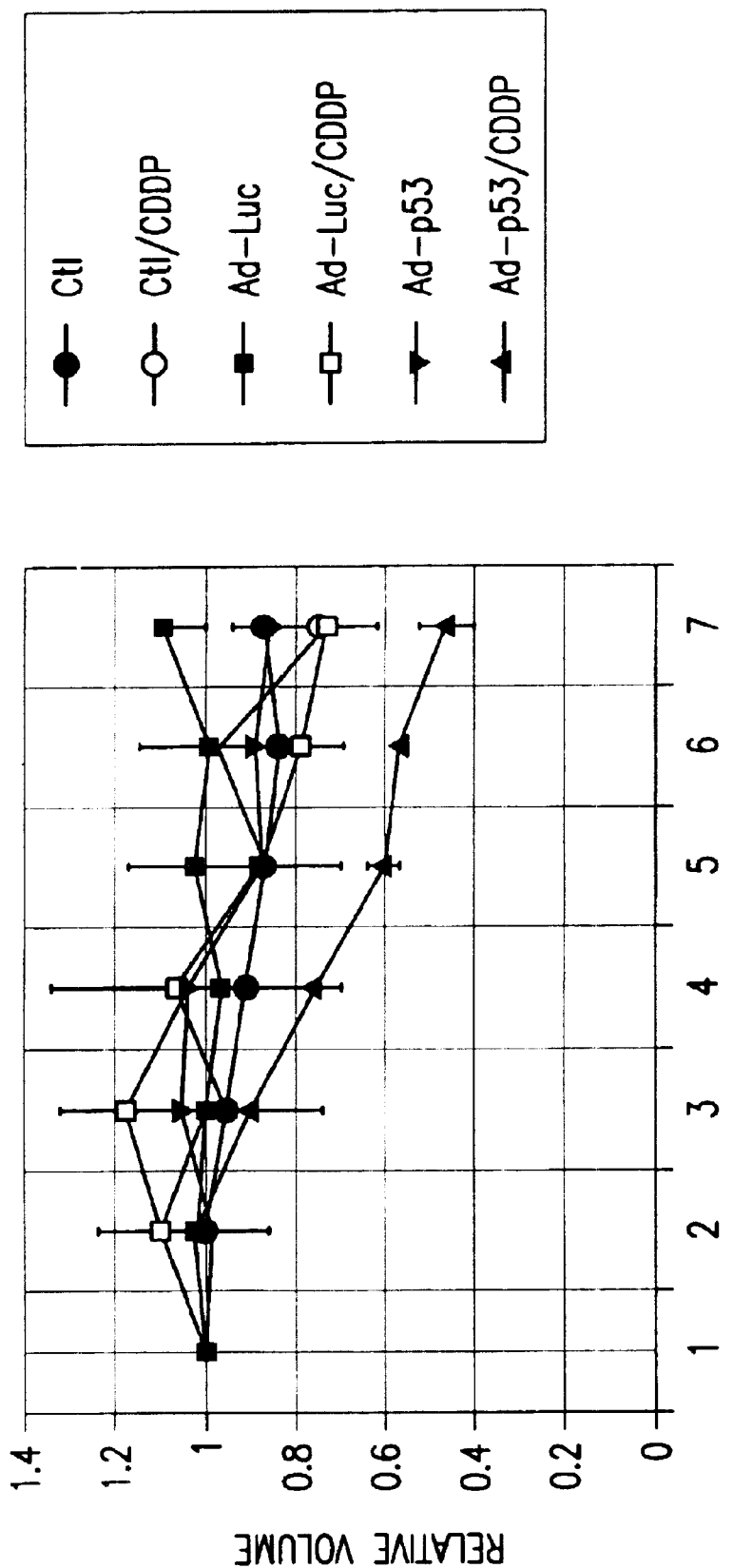
FIG. 12A. Effect of the combination of Ad-p53 infection with CDDP treatment on H358 tumor spheroids. Multicellular tumor spheroids of H358 cells were prepared as previously described (Takahashi, et al. (1989)). On day 0, spheroids with a diameter of 150 to 200 μm were placed in a 24-well agar coated plate and exposed to Ad-p53 or Ad-Luc for 24 hours. On day 1, medium with 10 μg/ml of CDDP was added following removal of virus-containing medium. On day 2, after a 24-hour incubation, the overlay was replaced with 1 ml of fresh drug-free medium. The perpendicular diameters were measured using an inverted microscope. The relative volume change was calculated according to the formula $a^2 \times b / a_1^2 \times b_1$, where a and b are the smallest and largest diameters of the spheroid, respectively, and $a_1$ and $b_1$ are the diameters on day 1. Only the relative volume of the Ad-p53/CDDP spheroids is significantly less ($p<0.05$ by Student's t-test) than the control group (Ctl).
Figure 12B:
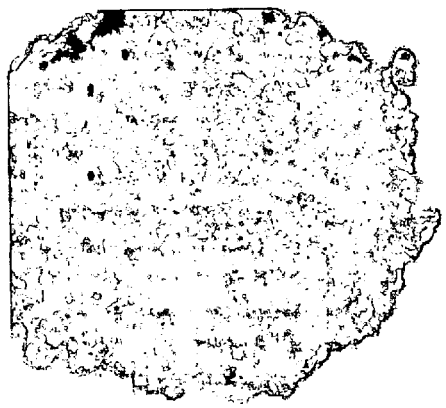
FIGS. 12B, 12C, 12D, and 12E. In situ dUTP labeling with TdT for detection of apoptosis. H358 spheroids were fixed on day 3 and stained as described in Materials and Methods of Example 7. (B) Control untreated spheroid, (C) spheroid treated with CDDP, (D) Ad-p53-infected spheroid, and (E) Ad-p53-infected spheroid treated with CDDP. Bar=100 μm.
Figure 12C:
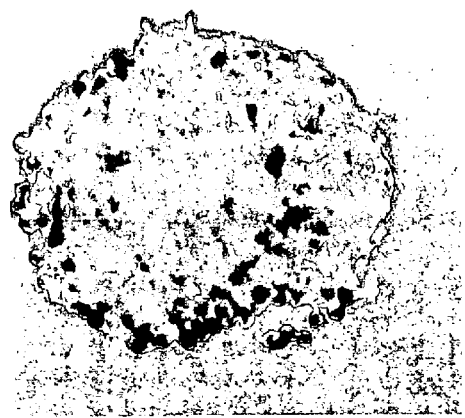
Figure 12D:
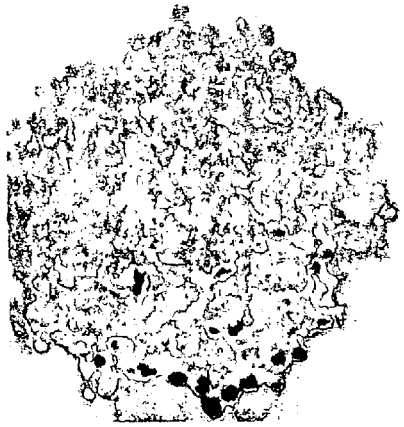
Figure 12E:
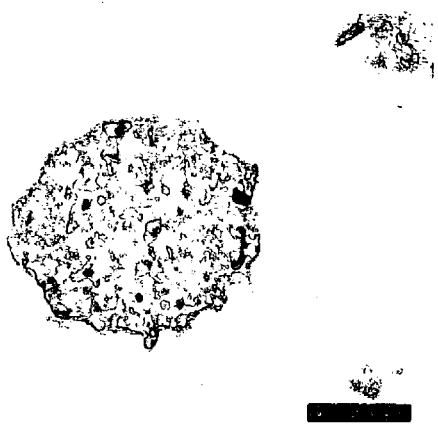

The potential therapeutic efficacy of the combination of Ad-p53 and CDDP was evaluated in terms of the relative change in volume of H358 spheroids. The multicellular tumor spheroid model exhibits in vitro a histologic structure similar to that of primary tumors and micrometastases. Treatment with CDDP caused a reduction of relative volume in Ad-p53-infected H358 spheroids, but had no significant effect on parental or Ad-Luc-infected spheroids (FIG. 12A). In situ TdT-mediated dUTP labeling showed many cells in the process of apoptosis on the surface of Ad-p53-infected spheroids, while no apoptotic cells were seen on spheroids not infected with Ad-p53 (FIGS. 12B–E). The inventors have previously reported that retroviral-mediated wt-p53 expression inhibited growth of H322a spheroids induced by transforming growth factor α (TGF-α) (Fujiwara, et al., 1993). The retroviral vector could not infect H358 spheroids, however, because cells in these spheroids did not proliferate rapidly in response to exogenous TGF-α. The finding that exposure to CDDP reduced the size of H358 spheroids infected with Ad-p53 by inducing apoptosis on the surface suggests that Ad-p53 infects nonproliferating cells and that CDDP initiates the apoptotic process in quiescent cells.

EXAMPLE 8

Using p53 and DNA Damaging Agents in Treatment Regimens

An animal models has been employed as part of pre-clinical trials, as described hereinbelow and in Examples 5, 6 and 7. Patients for whom the medical indication for adenovirus-mediated gene transfer treatment has been established may be tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation would be indicated.

For the treatment of cancer using Ad5CMV-p53, recombinant adenovirus expressing p53 under the control of suitable promoter/enhancer elements, such as the CMV promoter, would be prepared and purified according to a method that would be acceptable to the Food and Drug Administration (FDA) for administration to human subjects. Such methods include, but are not limited to, cesium chloride density gradient centrifugation, followed by testing for efficacy and purity.

Two basic methods are considered to be suitable for p53 adenovirus treatment methods, a direct or local administration and a more general administration. The present methods are suitable for treating any of the variety of different cancers known to be connected with p53 mutations. In regard to general administration, a simple intravenous injection of adenovirus has been shown to be sufficient to result in viral infection of tissues at sites distant from the injection (Stratford-Perricaudet et al., 1991b), and is thus suitable for the treatment of all p53-linked malignancies. The virus may be administered to patients by means of intravenous administration in any pharmacologically acceptable solution, or as an infusion over a period of time. Generally speaking, it is believed that the effective number of functional virus particles to be CBS administered would range from $1 \times 10^{10}$ to $5 \times 10^{12}$.

Also, particularly where lung cancer is concerned, more direct physical targeting of the recombinant adenovirus could be employed if desired, in an analogous manner to the intratracheal administration of the cystic fibrosis transmembrane conductance regulator (Rosenfeld et al., 1992). This would result in the delivery of recombinant p53 adenovirus closer to the site of the target cells.

Methods

In situ dUTP labeling with TdT for detection of apoptosis. H358 spheroids were fixed on day 3 and stained as described in Example 7. Briefly, labeled TdT probes were contacted to slides immersed in TdT buffer and incubated with biotinylated dUTP and TdT at 37° C. for 45 min. The slides were covered with 2% bovine serum albumin for 10 min and incubated with avidin-biotin complex for 30 min. The calorimetric detection was performed using diamino-benzidine.

Induction of apoptosis by CDDP after in vivo infection with Ad-p53. H358 cells ($5 \times 10^6$) in 0.1 ml Hank's balanced salt solution were injected subcutaneously into the right flank of BALB/c female nu/nu mice. Thirty days later, 200 µl of medium alone or medium containing Ad-Luc ($10^8$ PFU/ml) or Ad-p53 ($10^8$ PFU/ml) was injected into tumors with a diameter of 5 to 6 mm. Intratumoral injection (100 µl) and peritumoral injection in two opposite sites (50 µl each) were performed. CDDP (3 mg/kg) or control physiological saline was given intraperitoneally. (A) Tumor volume changes. The tumors were measured with calipers in two perpendicular diameters without the knowledge of the treatment groups, and a tumor volume was calculated by assuming a spherical shape with the average tumor diameter calculated as the square root of the product of cross-sectional diameters. Five mice were used for each treatment group and the mean +/− SE is shown. The data was analyzed using the Student's t-test. The arrow shows the day of treatment. Two independent determinations are shown. $p<0.05$ from day 5 in test 1; $p<0.05$ from day 7 in test 2. Histologic study using the TdT-mediated biotin-dUTP labeling technique. Tumors were harvested 5 days after the beginning of treatment and immediately embedded into O.C.T. compound. Frozen tissues were cut in a cryostat at 5-µm thicknesses. The sections were treated with 1 µg/ml proteinase K and stained as described above. All animal care was in accordance with the UT M.D. Anderson Institutional Animal Care and Use Committee.

Results

To demonstrate the in vivo efficacy of the methods and compositions efficacy of a combination of gene replacement therapy and chemotherapy in human cancer, the inventors examined, whether sequential administration of Ad-p53 and-CDDP could induce apoptosis in vivo. Following 3 days of direct intratumoral injection of Ad-p53 or intraperitoneal administration of CDDP, H358 tumors implanted subcutaneously in nu/nu mice showed a modest slowing of growth. However, if Ad-p53 and CDDP were simultaneously administered, tumors partially regressed and the tumor size remained statistically significantly smaller than those in any of the other treatment groups. The growth inhibitory effect was even more pronounced after two treatment cycles (FIG. 13A). Histologic examination revealed a massive destruction of tumor cells in the area where Ad-p53 was injected in mice treated with CDDP. In situ staining demonstrated many apoptotic cells around acellular spaces (FIGS. 13B–E). In contrast, tumors treated with CDDP alone or Ad-p53 alone showed neither acellularity nor apoptotic areas.

In more detail, preferred treatment protocols may be developed along the following lines. Patients may first undergo bronchoscopy to assess the degree of obstruction. As much gross tumor as possible should be resected endoscopically. Patients should preferably undergo bronchoscopy under topical or general anesthesia. A Stifcor™ transbronchial aspiration needle (21 g) will be passed through the biopsy channel of the bronchoscope. The residual tumor site would then be injected with the p53 adenovirus in a small volume such as about 10 ml or less.

In any event, since the adenovirus employed will be replication incompetent, no deleterious effect of the virus itself on subject health is anticipated. However, patients would remain hospitalized during the treatment for at least 48 hours to monitor acute and delayed adverse reactions. Safety-related concerns of the use of replication deficient adenovirus as a gene transfer vehicle in humans have been addressed in the past (Rosenfeld et al., 1992; Jaffe et al., 1992), but the dose of adenovirus to be administered should be appropriately monitored so as to further minimize the chance of untoward side effects.

There are various criteria that one should consider as presenting the existence of a need for response or the existence of toxicity. To assist in determining the existence of toxicity, the tumor bed should be photographed prior to a course of therapy. The longest diameter and its perpendicular will be measured. Size will be reported as the product of the diameters. From these data, one can calculate from these numbers the rate of regrowth of the tumor.

The time to progression can also be measured from the first observation with reduction in tumor bulk until there is evidence of progressive disease. Progressive Disease is defined as an increase of $\geq 25\%$ in the sum of the products of the diameters of the measured lesion. Patients must have received at least two courses of therapy before a designation of progression is made. The survival of patients will be measured from entry into protocol.

Follow-up examinations would include all those routinely employed in cancer therapy, including monitoring clinical signs and taking biopsies for standard and molecular biological analysis in which the pattern of expression of various p53 genes could be assessed. This would also supply information about the number of cells that have taken up the transferred gene and about the relative promoter strength in vivo. Based on the data obtained adjustments to the treatment may be desirable. These adjustments might include adenovirus constructs that use different promoters or a change in the number of pfu injected to ensure a infection of more, or all, tumor cells without unphysiological overexpression of the recombinant genes.

It is contemplated that the expression of exogenous genes transferred in vivo by adenovirus can persist for extended periods of time. Therapeutically effective long-term expression of virally transferred exogenous genes will have to be addressed on a case by case basis. Marker genes are limited in their usefulness to assess therapeutically relevant persistence of gene expression as the expression levels required for the amelioration of any given genetic disorder might differ considerably from the level required to completely cure another disease.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter and methods can be made and executed without undue experimentation.

REFERENCES

The following references to the extent that they provide exemplary procedural or other details supplementary to those set forth herein, are specifically incorporated herein by reference.

Bargonetti, et al. (1991) *Cell* 65:1083–1091.
Bishop (1987) *Science* 235:305–311.
Boeheringer Mannheim Biochemicals (1992). DOTAP for high efficiency transfections, *BMBiochemica* 9(1):17.
Boshart, M. et al. (1985). A very strong enhancer is located upstream of an immediate early gene of human cytomegalovirus. *Cell*, 41:521–530.

Cai, D. W., Mukhopadhyay, T., Liu, T., Fujiwara, T., and Roth, J. A. Stable expression of the wild-type p53 gene in human lung cancer cells after retrovirus-mediated gene transfer. *Human Gene Ther*, 4: 617–624, 1993.

Culver, K. W., Ram, Z., Wallbridge, S., Ishii, H., Oldfield, E. H., and Blaese, R. M. In vivo gene transfer with retroviral vector-producer cells for treatment of experimental brain tumors. *Science*, 256: 1550–1552, 1992.

Casey, G. Lo-Hueh, M., Lopez, M. E., Vogelstein, B., and Stanbridge, E. J. (1991). Growth suppression of human breast cancer cells by the introduction of a wild-type p53 gene. *Oncogene* 6:1791–1797.

Clarke, A. R., Purdie, C. A., Harrison, D. J., Morris, R. G., Bird, C. C., Hooper, M. L., and Wyllie, A. H. Thymocyte apoptosis induced by p53-dependent and independent pathways. *Nature*, 362: 849–852, 1993.

Dai, et al. (1992) *Proc. Natl. Acad. Sci.* 89:10892–10895.

Doyle, L. A. Mechanisms of drug resistance in human lung cancer cells. Semin Oncol, 20: 326–337, 1993.

El-Deiry, W. S., Tokino, T., Velculescu, V. E., Levy, D. B., Parsons, R., Trent, J. M., Lin, D., Mercer, E., Kinzler, K. W., and Vogelstein, B. WAF1, a potential mediator of p53 tumor suppression. *Cell*, 75: 817–825, 1993.

Fritsche, M., Haessler, C., and Brandner, G. Induction of nuclear accumulation of the tumor-suppressor protein p53 by DNA-damaging agents. *Oncogene*, 8: 307–318, 1993.

Fields et al. (1990) *Science* 249:1046–1049.

Fujiwara, T., Grimm, E. A., Mukhopadhyay, T., Cai, D. W., Owen-Schaub, L. B., and Roth, J. A. A retroviral wild-type p53 expression vector penetrates human lung cancer spheroids and inhibits growth by inducing apoptosis. *Cancer Res*, 53: 4129–4133, 1993.

Gavrieli, Y., Sherman, Y., and Ben-Sasson, S. A. Identification of programmed cell death in situ via specific labelling of nuclear DNA fragmentation. J Cell Biol, 119: 493–501, 1992.

Georges et al. (1993) *Cancer Res* 53:1743–1746.

Ghosh-Choudhury and Graham (1987) *Biochem. Biophys. Res. Comm.* 147:964–973.

Gluzman et al., (1982) in *Eukaryotic Viral Vectors* (Gluzman, Y., Ed.) pp. 187–192, Cold Spring Harbor Press, Cold Spring Harbor, N.Y.

Graham, F. L. and A. J. van der Eb. (1973). A new technique for the assay of infectivity of human adenovirus 5 DNA. *Virology* 52:456–467.

Graham, F. L. and Prevec, L. Manipulation of adenovirus vectors. In: Murray E. J. (ed.), Methods in Molecular Biology, Gene Transfer and Expression Protocols, pp. 109–128. New Jersey: The Humana Press Inc, 1991.

Graham, F. L., J. Smiley, W. C. Russell and R. Nairn (1977). Characteristics of a human cell line transformed by DNA from human adenovirus type 5. *J. Gen Virol.* 36:59–72.

Grunhaus, A. and Horwitx, M. S. (1992). Adenoviruses as cloning vectors. *Semin. Virology* 3:237–2542.

Harper, J. E., Adami, G. R., Wei, N., Keyomarsi, K., and Elledge, S. J. The p21 Cdk-interacting protein Cip1 is a potent inhibitor of G1 cyclin-dependent kinases. *Cell*, 75: 805–816, 1993.

Hollstein, M., Sidransky, D., Vogelstein, B., and Harris, C. (1991). p53 mutations in human cancers. *Science* 253:49–53.

Jaffe et al., (1992) *Nature Genetics* 1:372–378.

Le Gal et al., (1993) *Science* 259:988–990.

Ledley, J. (1987). *J. Pediatrics* 110, 1.

Levine, A. J., Momand, J., and Finlay, C. A. The p53 tumour suppressor gene. *Nature*, 351: 453–456, 1991.

Lowe, S. W., Ruley, H. E., Jacks, T., and Housman, D. E. p53-dependent apoptosis modulates the cytotoxicity of anticancer agents. *Cell*, 74: 957–967, 1993.

Lowe, S. W., Schmitt, E. M., Smith, S. W., Osborne, B. A., and Jacks, T. p53 is required for radiation-induced apoptosis in mouse thymocytes. *Nature*, 362: 847–849, 1993.

McGrory, W. J. et al. (1988). A simple technique for the rescue of early region I mutations into infectious human adenovirus type 5. *Virology* 163:614–617.

Mercer, W. E. (1992). Cell cycle regulation and the p53 tumor suppressor protein. *Critic. Rev. Eukar. Gene Express.* 2:251–263.

Mietz, et al. (1992) *EMBO* 11:5013–5020.

Miller. 1992, *Curr. Top. Microbiol. Immunol.* 158:1

Montenarh, M. (1992). Biochemical, immunological, and functional aspects of the growth-suppressor/oncoprotein p53. *Critic. Rev. Onco.* 3:233–256.

Mulligan, (1993), *Science* 260:926.

Nicolau, C., et al. (1983). *Proc. Natl. Acad. Sci. U.S.A.* 80, 1068.

Ragot et al., (1993) *Nature*, 361:647–650.

Ramqvist, T., Magnusson, K. P., Wang, Y., Szekeley, L., and Klein, G. wild-type p53 induces apoptosis in a Burkitt lymphoma (BL) line that carries mutant p53. *Oncogene*, 8: 1495–1500, 1993.

Rosenfeld et al., (1992) *Cell* 68:143–155.

Rosenfeld et al., (1991) *Science*, 232:431–434.

Roth, J., Ruckdeschel, Weisenburger, Editors, Thoracic Oncology, First Edition, Chapter 49, pgs 711–721, Sanders, N.Y., 1989.

Shaw, P., Bovey, R., Tardy, S., Sahli, R., Sordat, B., and Costa, J. Induction of apoptosis by wild-type 53 in a human colon tumor-derived cell line. *Proc Natl Acad Sci USA*, 89: 4495–4499, 1992.

Spandidos, et al. (1989), *J. Pathol.*, 157:1–10.

Stewart et al., 1992, *Hum. Gene Ther.* 3:267

Stratford-Perricaudet, L. and M. Perricaudet. (1991a). Gene transfer into animals: the promise of adenovirus. p. 51–61, In O. Cohen-Haguenauer and M. Boiron (Eds.), Human Gene Transfer, Editions John Libbey Eurotext, France.

Stratford-Perricaudet et al., (1991b) *Hum. Gene. Ther.* 1:241–256

Takahashi, T., Nau, M. M., Chiba, I., Birrer, M. J., Rosenberg, R. K., Vinocour, M., Levitt, M., Pass, H., Gazdar, A. F., and Minna, J. D. p53: a frequent target for genetic abnormalities in lung cancer. *Science*, 246: 491–494, 1989.

Takahashi, T., Carbone, D., Takahashi, T., Nau, M. M., Hida, T., Linnoila, I., Ueda, R., and Minna, J. D. (1992). Wild-type but not mutant p53 suppresses the growth of human lung cancer cells bearing multiple genetic lesions. 1992. *Cancer Res.* 52:2340–2342.

Tishler, R. B., Calderwood, S. K., Coleman, C. N., and Price, B. D. Increases in sequence specific DNA binding by p53 following treatment with chemotherapeutic and DNA damaging agents. *Cancer Res*, 53: 2212–2216, 1993.

Tooza, J. (1981). Molecular biology of DNA Tumor viruses, 2nd ed. Cold Spring Harbor Laboratory, Cold Spring Harbor, N.Y.

Torchilin et al., 1992, *Faseb J.* 6:2716

Travali, et al. (1990), *FASEB*, 4:3209–3214.

Weinberg, R. A. (1991). Tumor suppressor gene. *Science* 254:1138–1145.

Wilcock, et al. (1991) *Nature* 349:429–431.

Wolff, J. A., Malone, R. W., Williams, P., Chong, W., Acsadi, G., Jani, A., and Felgner, P. L. (1990) Direct gene transfer into mouse muscle in vivo. *Science* 247, 1465–1468.

Yonish-Rouach, E., Resnitzky, D., Rotem, J., Sachs, L., Kimchi, A., and Oren, M. wild-type p53 induces apoptosis of myeloid leukemic cells that is inhibited by interleukin-6. *Nature*, 352: 345–347, 1991.

Zakut-Houri et al. (1985), *EMBO J.*, 4:1251–1255.

Zhan, Q., Carrier, F., and Fornace Jr., A. J. Induction of cellular p53 activity by DNA-damaging agents and growth arrest. *Mol Cell Biol*, 13: 4242–4250, 1993.

Zhang, W. W., Fang, X., Branch, C. D., Mazur, W., French, B. A., and Roth, J. A. Generation and identification of recombinant adenovirus by lipsome-mediated transfection and PCR analysis. *BioTechniques*, 1993.

Zhang, W. W., Fang, X., Mazur, W., French, B. A., Georges, R. N., and Roth, J. A. High-efficiency gene transfer and high-level expression of wild-type p53 in human lung cancer cells mediated by recombinant adenovirus. Cancer Gene Therapy, 1993.

Zhu, et al., 1993, *Science* 261:209–211.

What is claimed is:

1. A method of reducing the growth rate of a tumor, comprising contacting a cell within said tumor with (a) a DNA segment encoding a functional p53 protein and (b) a DNA damaging agent in a combined amount effective to inhibit the growth of said tumor.

2. The method of claim 1, wherein the DNA damaging agent is X-ray radiation, UV-irradiation, -irradiation, microwaves, adriamycin, 5-fluorouracil, etoposide, camptothecin, actinomycin-D, mitomycin C, or cisplatin.

3. The method of claim 2, wherein said cell is contacted with the DNA segment in combination with cisplatin.

4. The method of claim 1, wherein the DNA segment is in a recombinant vector that expresses the functional p53 protein in said cell.

5. The method of claim 4, wherein said p53-expressing recombinant vector is a naked DNA plasmid, a plasmid within a liposome, a retroviral vector, an AAV vector, or a recombinant adenoviral vector.

6. The method of claim 5, wherein said p53-expressing recombinant vector is a recombinant adenoviral vector.

7. The method of claim 4, wherein said p53-expressing recombinant, non-viral vector comprises a p53 expression region positioned under the control of a promoter.

8. The method of claim 4, wherein said recombinant, non-viral vector comprises a p53 expression region, the cytomegalovirus IE promoter and the SV40 early polyadenylation signal.

9. The method of claim 6, wherein at least one gene essential for adenovirus replication is deleted from said adenovirus vector and a p53 expression region is introduced in its place.

10. The method of claim 9, wherein E1A and E1B regions of the adenovirus vector are deleted and the p53 expression region is introduced in their place.

11. The method of claim 1, wherein said cell is first contacted with the DNA segment and is subsequently contacted with said DNA damaging agent.

12. The method of claim 1, wherein said cell is first contacted with said DNA damaging agent and is subsequently contacted with the DNA segment.

13. The method of claim 1, wherein said cell is simultaneously contacted with the DNA segment and said DNA damaging agent.

14. The method of claim 1, wherein said cell is contacted with a first composition comprising the DNA segment and a second composition comprising said DNA damaging agent.

15. The method of claim 14, wherein said first or second composition is dispersed in a pharmacologically acceptable formulation.

16. The method of claim 1, wherein said cell is contacted with a single composition comprising the DNA segment in combination with said DNA damaging agent.

17. The method of claim 16, wherein said composition is dispersed in a pharmacologically acceptable formulation.

18. The method of claim 16, wherein said cell is contacted with a single composition comprising a recombinant vector that expresses p53 in said cell in combination with said DNA damaging agent.

19. The method of claim 18, wherein said cell is contacted with a single composition comprising a recombinant adenovirus containing a recombinant vector that expresses p53 in said cell in combination with said DNA damaging agent.

20. The method of claim 1, wherein said cell is a malignant cell.

21. The method of claim 20, wherein said malignant cell is a lung cancer cell.

22. The method of claim 20, wherein said malignant cell is a breast cancer cell.

23. The method of claim 20, wherein said malignant cell has a mutation in a p53 gene.

24. The method of claim 1, wherein said cell is located within an animal at a tumor site.

25. A composition comprising a) an exogenous DNA segment encoding a functional p53 polypeptide and b) compound comprising a DNA damaging agent.

26. The composition of claim 25, wherein the DNA damaging agent is adriamycin, 5-fluorouracil, etoposide, camptothecin, actinomycin-D, mitomycin C, or cisplatin.

27. The composition of claim 26, wherein the DNA damaging agent is cisplatin.

28. The composition of claim 25, wherein the exogenous DNA segment is in a recombinant vector that expresses a functional p53 protein in an animal cell.

29. The composition of claim 28, wherein said recombinant vector is a naked DNA plasmid or a plasmid within a liposome.

30. The composition of claim 29, wherein said recombinant vector is a recombinant adenoviral vector.

31. The composition of claim 30, wherein the recombinant vector is a recombinant adenoviral vector and the DNA damaging agent is cisplatin.

32. The composition of claim 25, dispersed in a pharmacologically acceptable formulation.

33. The composition of claim 32, formulated for intralesional administration.

34. A therapeutic kit comprising, in suitable container means, a pharmaceutical formulation of a recombinant vector that expresses a functional p53 protein in an animal cell and a pharmaceutical formulation of a DNA damaging agent.

35. The kit of claim 34, wherein said recombinant vector and said DNA damaging agent are present within a single container means.

36. The kit of claim 34, wherein said recombinant vector and said DNA damaging agent are present within distinct container means.

37. The kit of claim 34, wherein the recombinant vector is an adenovirus vector and the DNA damaging agent is cisplatin.

38. The method of claim 1, wherein the cell is contacted with a DNA damaging agent by irradiating the cell with X-ray radiation, UV-irradiation, γ-irradiation or microwaves.

39. The method of claim 38, wherein the cell is contacted with a DNA damaging agent by irradiating the cell with X-ray radiation.

40. The method of claim 38, wherein the cell is contacted with a DNA damaging agent by irradiating the cell with UV-irradiation.

41. The method of claim 38, wherein the cell is contacted with a DNA damaging agent by irradiating the cell with γ-irradiation.

42. The method of claim 38, wherein the cell is contacted with a DNA damaging agent by irradiating the cell with microwaves.

43. The method claim 1, wherein the cell is contacted with a pharmaceutical composition comprising the DNA damaging agent.

44. The method of claim 43, wherein the DNA damaging agent is cisplatin.

45. The method of claim 43, wherein the DNA damaging agent is doxorubicin.

46. The method of claim 43, wherein the DNA damaging agent is etoposide.

47. The method of claim 43, wherein the DNA damaging agent is verapamil.

48. The method of claim 43, wherein the DNA damaging agent is podophyllotoxin.

49. The method of claim 43, wherein the DNA damaging agent is 5-FU.

50. The method of claim 43, wherein the DNA damaging agent is adriamycin-D.

51. The method of claim 43, wherein the DNA damaging agent is adriamycin.

52. The method of claim 43, wherein the DNA damaging agent is camptothecin.

53. The method of claim 43, wherein the DNA damaging agent is mitomycin C.

54. The method of claim 4, wherein said DNA segment is administered prior to said DNA damaging agent.

55. The method of claim 4, wherein said DNA segment is administered after said DNA damaging agent.

56. The method of claim 4, wherein said DNA segment is administered at the same time as said DNA damaging agent.

57. The method of claim 24, wherein said DNA segment is delivered to said tumor endoscopically, intravenously, intratracheally, intralesionally, percutaneously or subcutaneously.

58. The method of claim 24, wherein said tumor site is a resected tumor bed.

59. The method of claim 24, wherein said administration is repeated.

60. The method of claim 12, wherein there is 12 to 24 hours between administration of the DNA damaging agent and administration of the DNA segment.

61. The method of claim 12, wherein there is 6 to 12 hours between administration of the DNA damaging agent and administration of the DNA segment.

62. The method of claim 12, wherein there is about 12 hours between administration of the DNA damaging agent and administration of the DNA segment.

63. The method of claim 11, wherein there is 12 to 24 hours between administration of the DNA segment and administration of the DNA damaging agent.

64. The method of claim 11, wherein there is 6 to 12 hours between administration of the DNA segment and administration of the DNA damaging agent.

65. The method of claim 11, wherein there is about 12 hours between administration of the DNA segment and administration of the DNA damaging agent.

66. The method of claim 1, wherein said tumor cell is an epithelial tumor cell.

67. The method of claim 21, wherein said lung cancer cell is non-small cell lung carcinoma cell.

68. The method of claim 67, herein said non-small cell lung carcinoma cell is a squamous carcinoma cell.

69. The method of claim 67, wherein said non-small cell lung carcinoma cell is an adenocarcinoma cell.

70. The method of claim 67, wherein said non-small cell lung carcinoma cell is a large-cell undifferentiated carcinoma cell.

71. The method of claim 21, wherein said lung cancer cell is a small cell lung carcinoma cell.

72. The method of claim 24, wherein said gene is administered in about 0.1 ml.

73. The method of claim 24, wherein said gene is administered in about 10 ml.

74. The method of claim 44, wherein said cisplatin is administered at 20 mg/m$^2$.

75. The method of claim 45, wherein said doxorubicin is administered at 25–75 mg/m$^2$.

76. The method of claim 46, wherein said etoposide is administered at 35–50 mg/m$^2$.

77. The method of claim 48, wherein said 5-FU is administered at 3–15 mg/kg.

78. The method of claim 39, wherein the cell is irradiated with about 2000 to 6000 roentgens.

79. The method of claim 39, wherein the cell is irradiated with about 50 to 200 roentgens.

80. The method of claim 7, wherein the promoter is selected from the group consisting of SV40, CMV and RSV.

81. The method of claim 80, wherein the promoter is the CMV IE promoter.

82. The method of claim 81, wherein the vector further comprises a polyadenylation signal.

\* \* \* \* \*

UNITED STATES PATENT AND TRADEMARK OFFICE
CERTIFICATE OF CORRECTION

PATENT NO.    : 6,797,702 B1
DATED         : September 28, 2004
INVENTOR(S)   : Roth et al.

It is certified that error appears in the above-identified patent and that said Letters Patent is hereby corrected as shown below:

Column 37,
Line 8, delete "UV-irradiation, -irradiation" and insert -- UV-irradiation, $\gamma$ -irradiation --.
Line 23, delete "non-viral" after "recombinant".
Line 24, insert -- constitutive -- before "promoter".
Line 26, delete "non-viral" before "vector".
Line 26, delete "the" and insert -- a --.
Line 27, delete "the SV40" and insert -- an SV40 --.
Lines 31 and 34, delete "adenovirus" and insert -- adenoviral --.
Lines 58 and 62, before "p53" insert -- the --.

Column 38,
Line 9, before "compound" insert -- a --.
Line 20, delete "claim 29" and insert -- claim 28 --.
Lines 22-23, delete "the recombinant vector is a recombinant adenoviral vector and".

Column 39,
Line 8, delete "adiamycin-D" and insert -- actinomycin-D --.
Line 27, delete "administration" and insert -- contacting --.

Column 40,
Line 4, delete "tumor".
Line 8, before "non-small" insert -- a --.
Lines 19 and 21, delete "gene" and insert -- DNA segment --.
Line 29, delete "claim 48" and insert -- claim 49 --.

Signed and Sealed this

Eighteenth Day of October, 2005

JON W. DUDAS
*Director of the United States Patent and Trademark Office*